United States Patent
Stojdl et al.

(10) Patent No.: US 10,646,557 B2
(45) Date of Patent: *May 12, 2020

(54) VACCINE COMPOSITION

(71) Applicant: TURNSTONE LIMITED PARTNERSHIP, Toronto (CA)

(72) Inventors: David F. Stojdl, Ottawa (CA); John Cameron Bell, Ottawa (CA); Brian Lichty, Brantford (CA)

(73) Assignee: TURNSTONE LIMITED PARTNERSHIP, Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/249,616

(22) Filed: Jan. 16, 2019

(65) Prior Publication Data

US 2019/0240301 A1 Aug. 8, 2019

Related U.S. Application Data

(63) Continuation of application No. 14/769,035, filed as application No. PCT/CA2014/050118 on Feb. 20, 2014, now Pat. No. 10,363,293.

(60) Provisional application No. 61/767,776, filed on Feb. 21, 2013.

(51) Int. Cl.
| | |
|---|---|
| *A61K 39/00* | (2006.01) |
| *C12N 15/86* | (2006.01) |
| *A61K 39/12* | (2006.01) |
| *A61K 35/766* | (2015.01) |
| *C12N 7/00* | (2006.01) |

(52) U.S. Cl.
CPC ........ *A61K 39/0005* (2013.01); *A61K 35/766* (2013.01); *A61K 39/0011* (2013.01); *A61K 39/12* (2013.01); *C12N 7/00* (2013.01); *C12N 15/86* (2013.01); *A61K 2039/5254* (2013.01); *A61K 2039/5256* (2013.01); *A61K 2039/545* (2013.01); *A61K 2039/55561* (2013.01); *A61K 2039/572* (2013.01); *A61K 2039/585* (2013.01); *C07K 2319/00* (2013.01); *C07K 2319/50* (2013.01); *C12N 2710/10343* (2013.01); *C12N 2710/16234* (2013.01); *C12N 2710/20034* (2013.01); *C12N 2740/15043* (2013.01); *C12N 2760/20223* (2013.01); *C12N 2760/20232* (2013.01); *C12N 2760/20242* (2013.01); *C12N 2760/20243* (2013.01)

(58) Field of Classification Search
None
See application file for complete search history.

(56) References Cited

U.S. PATENT DOCUMENTS

| | | |
|---|---|---|
| 4,554,101 A | 11/1985 | Hopp |
| 4,683,195 A | 7/1987 | Mullis et al. |
| 4,683,202 A | 7/1987 | Mullis |
| 4,684,611 A | 8/1987 | Schilperoort et al. |
| 4,800,159 A | 1/1989 | Mullis et al. |
| 4,879,236 A | 11/1989 | Smith et al. |
| 4,883,750 A | 11/1989 | Whitely et al. |
| 4,946,773 A | 8/1990 | Maniatis |
| 4,952,500 A | 8/1990 | Finnerty et al. |
| 5,220,007 A | 6/1993 | Pederson et al. |
| 5,279,721 A | 1/1994 | Schmid |
| 5,302,523 A | 1/1994 | Coffee et al. |
| 5,284,760 A | 2/1994 | Feinstone et al. |
| 5,322,783 A | 6/1994 | Tomes et al. |
| 5,354,670 A | 10/1994 | Nickoloff et al. |
| 5,366,878 A | 11/1994 | Pederson et al. |
| 5,384,253 A | 1/1995 | Krzyzek et al. |
| 5,389,514 A | 2/1995 | Taylor |
| 5,399,363 A | 3/1995 | Liversidge et al. |
| 5,464,765 A | 11/1995 | Coffee et al. |
| 5,466,468 A | 11/1995 | Schneider et al. |
| 5,538,877 A | 7/1996 | Lundquist et al. |
| 5,538,880 A | 7/1996 | Lundquist et al. |
| 5,543,158 A | 8/1996 | Gref et al. |
| 5,550,318 A | 8/1996 | Adams et al. |
| 5,563,055 A | 10/1996 | Townsend et al. |
| 5,580,859 A | 12/1996 | Feigner et al. |

(Continued)

FOREIGN PATENT DOCUMENTS

| | | |
|---|---|---|
| AU | 2010329551 B2 | 2/2016 |
| AU | 2014221143 B2 | 5/2019 |

(Continued)

OTHER PUBLICATIONS

Bridle et al. Molecular Therapy 2010, vol. 18, pp. 1430-1439 (Year: 2010).*
Wang et al. Cancer Letters 2010, vol. 291, pp. 67-75 (Year: 2010).*
Brun et al. Molecular Therapy 2010, vol. 18, pp. 1440-1448 (Year: 2010).*
van der Sluis et al. Current Opinion in Immunology 2015, vol. 35, pp. 9-14 (Year: 2015).*
Ikeda, Keiro, et al. "Oncolytic virus therapy of multiple tumors in the brain requires suppression of innate and elicited antiviral responses." Nature medicine vol. 5, No. 8, p. 881, Aug. 1999.

(Continued)

*Primary Examiner* — Shanon A. Foley
*Assistant Examiner* — Myron G Hill
(74) *Attorney, Agent, or Firm* — Jones Day

(57) ABSTRACT

There is described a kit for use in inducing an immune response in a mammal, the kit includes: a first virus that expresses MAGEA3, Human Papilloma Virus E6/E7 fusion protein, human Six-Transmembrane Epithelial Antigen of the Prostate protein, or Cancer Testis Antigen 1, or a variant thereof as an antigenic protein and that is formulated to generate an immunity to the protein or variant thereof in the mammal. The kit also includes a Maraba MG1 virus encoding the same antigen, or a variant of the same antigen. The Maraba MG1 virus is formulated to induce the immune response in the mammal. The first virus is immunologically distinct from the Maraba MG1 virus.

13 Claims, 8 Drawing Sheets

Specification includes a Sequence Listing.

(56) References Cited

U.S. PATENT DOCUMENTS

| | | |
|---|---|---|
| 5,585,461 A | 12/1996 | Townsend et al. |
| 5,589,466 A | 12/1996 | Feigner et al. |
| 5,591,616 A | 1/1997 | Hei et al. |
| 5,610,042 A | 3/1997 | Chang et al. |
| 5,635,377 A | 6/1997 | Pederson et al. |
| 5,641,515 A | 6/1997 | Ramtoola |
| 5,656,610 A | 8/1997 | Shuler et al. |
| 5,702,932 A | 12/1997 | Hoy et al. |
| 5,736,524 A | 4/1998 | Content et al. |
| 5,739,169 A | 4/1998 | Ocain et al. |
| 5,780,448 A | 7/1998 | Davis |
| 5,789,166 A | 8/1998 | Bauer et al. |
| 5,789,215 A | 8/1998 | Berns et al. |
| 5,798,208 A | 8/1998 | Crea |
| 5,801,005 A | 9/1998 | Cheever et al. |
| 5,824,311 A | 10/1998 | Greene et al. |
| 5,830,650 A | 11/1998 | Crea |
| 5,830,880 A | 11/1998 | Sedlacek et al. |
| 5,840,873 A | 11/1998 | Nelson et al. |
| 5,843,225 A | 12/1998 | Rosengart et al. |
| 5,843,233 A | 12/1998 | Lilley et al. |
| 5,843,640 A | 12/1998 | Patterson et al. |
| 5,843,650 A | 12/1998 | Segev |
| 5,843,651 A | 12/1998 | Stimpson et al. |
| 5,843,663 A | 12/1998 | Stanley et al. |
| 5,846,708 A | 12/1998 | Hollis et al. |
| 5,846,709 A | 12/1998 | Segev |
| 5,846,717 A | 12/1998 | Brow et al. |
| 5,846,726 A | 12/1998 | Nadeau et al. |
| 5,846,729 A | 12/1998 | Wu et al. |
| 5,846,783 A | 12/1998 | Wu et al. |
| 5,846,945 A | 12/1998 | McCormick |
| 5,849,481 A | 12/1998 | Urdea et al. |
| 5,849,483 A | 12/1998 | Shuber |
| 5,849,486 A | 12/1998 | Heller et al. |
| 5,849,487 A | 12/1998 | Hase et al. |
| 5,849,497 A | 12/1998 | Steinman |
| 5,849,546 A | 12/1998 | Sousa et al. |
| 5,849,547 A | 12/1998 | Cleuziat et al. |
| 5,851,770 A | 12/1998 | Babon et al. |
| 5,851,772 A | 12/1998 | Mirzabekov et al. |
| 5,853,990 A | 12/1998 | Winger et al. |
| 5,853,992 A | 12/1998 | Glazer et al. |
| 5,853,993 A | 12/1998 | Dellinger et al. |
| 5,856,092 A | 1/1999 | Dale et al. |
| 5,858,652 A | 1/1999 | Laffler et al. |
| 5,861,244 A | 1/1999 | Wang et al. |
| 5,863,732 A | 1/1999 | Richards |
| 5,863,753 A | 1/1999 | Haugland et al. |
| 5,866,331 A | 2/1999 | Singer et al. |
| 5,866,337 A | 2/1999 | Schon |
| 5,866,366 A | 2/1999 | Kallender |
| 5,871,986 A | 2/1999 | Boyce |
| 5,882,864 A | 3/1999 | An et al. |
| 5,900,481 A | 5/1999 | Lough et al. |
| 5,905,024 A | 5/1999 | Mirzabekov et al. |
| 5,910,407 A | 6/1999 | Vogelstein et al. |
| 5,912,124 A | 6/1999 | Kumar |
| 5,912,145 A | 6/1999 | Stanley |
| 5,912,148 A | 6/1999 | Eggerding |
| 5,916,776 A | 6/1999 | Kumar |
| 5,916,779 A | 6/1999 | Pearson et al. |
| 5,919,626 A | 7/1999 | Shi et al. |
| 5,919,630 A | 7/1999 | Nadeau et al. |
| 5,922,574 A | 7/1999 | Minter |
| 5,925,517 A | 7/1999 | Tyagi et al. |
| 5,925,525 A | 7/1999 | Fodor et al. |
| 5,925,565 A | 7/1999 | Berlioz et al. |
| 5,928,862 A | 7/1999 | Morrison |
| 5,928,869 A | 7/1999 | Nadeau et al. |
| 5,928,870 A | 7/1999 | Lapidus et al. |
| 5,928,905 A | 7/1999 | Stemmer et al. |
| 5,928,906 A | 7/1999 | Koester et al. |
| 5,929,227 A | 7/1999 | Glazer et al. |
| 5,932,413 A | 8/1999 | Celebuski |
| 5,932,451 A | 8/1999 | Wang et al. |
| 5,935,791 A | 8/1999 | Nadeau et al. |
| 5,935,819 A | 8/1999 | Eichner et al. |
| 5,935,825 A | 8/1999 | Nishimura et al. |
| 5,939,291 A | 8/1999 | Loewy et al. |
| 5,942,391 A | 8/1999 | Zhang et al. |
| 5,945,100 A | 8/1999 | Fick |
| 5,965,535 A | 10/1999 | Chaux et al. |
| 5,981,274 A | 11/1999 | Tyrrell et al. |
| 5,994,624 A | 11/1999 | Trolinder et al. |
| 7,452,723 B2 | 11/2008 | Coffey et al. |
| 9,045,729 B2 | 6/2015 | Bell et al. |
| 9,707,285 B2 * | 7/2017 | Lichty .............. A61K 39/0011 |
| 10,363,293 B2 | 7/2019 | Stojdl et al. |
| 2003/0157135 A1 | 8/2003 | Tsuji et al. |
| 2004/0170607 A1 | 9/2004 | Bell et al. |
| 2011/0250188 A1 | 10/2011 | Von Laer et al. |
| 2012/0014990 A1 | 1/2012 | Lichty et al. |
| 2015/0275185 A1 | 10/2015 | Bell et al. |
| 2015/0307559 A1 | 10/2015 | Stojdl et al. |

FOREIGN PATENT DOCUMENTS

| | | |
|---|---|---|
| CA | 2663034 A1 | 2/2009 |
| CA | 2921063 A1 | 2/2009 |
| CA | 2739963 A1 | 4/2010 |
| CN | 1962911 A | 5/2007 |
| CN | 102026645 A | 4/2011 |
| DE | 60026554 T2 | 9/2006 |
| DE | 1716858 A2 | 11/2006 |
| EP | 0320308 A2 | 6/1989 |
| EP | 0329822 A2 | 8/1989 |
| EP | 2958994 B1 | 5/2019 |
| GB | 2202328 A | 9/1988 |
| JP | 2004-525855 A | 8/2004 |
| JP | 2005-509404 A | 4/2005 |
| JP | 2006-518331 A | 8/2006 |
| JP | 2008-514203 A | 5/2008 |
| JP | 2010-526547 A | 8/2010 |
| RU | 2301260 C2 | 6/2007 |
| RU | 2011130511 A | 1/2013 |
| RU | 2684211 C2 | 4/2019 |
| WO | 1987006270 A1 | 10/1987 |
| WO | 1988010315 A1 | 12/1988 |
| WO | 1989006700 A1 | 7/1989 |
| WO | 1989009284 A1 | 10/1989 |
| WO | 1990007641 A1 | 7/1990 |
| WO | 1991009944 A2 | 7/1991 |
| WO | 1994009699 A1 | 5/1994 |
| WO | 1995006128 A2 | 3/1995 |
| WO | 2001019380 A2 | 3/2001 |
| WO | 2002067861 A2 | 9/2002 |
| WO | 2006061643 A1 | 6/2006 |
| WO | 2007025365 A1 | 3/2007 |
| WO | 2008009115 A1 | 1/2008 |
| WO | 2008011726 A1 | 1/2008 |
| WO | 2008094188 A2 | 8/2008 |
| WO | 2008140621 A2 | 11/2008 |
| WO | 2009016433 A2 | 2/2009 |
| WO | 2009036137 A1 | 3/2009 |
| WO | 2010105347 A1 | 9/2010 |
| WO | WO 2010129339 A2 | 11/2010 |
| WO | WO 2010129339 A3 | 11/2010 |
| WO | 2011070440 A2 | 6/2011 |
| WO | 2014127478 A1 | 8/2014 |

OTHER PUBLICATIONS

Imagawa et al., "Transcription Factor Ap-2 Mediates Induction by Two Different Signal-transduction Pathways: Protein Kinase C and Camp," Cell, vol. 51(2), Oct. 1987, pp. 251-260.

Imbra et al., "Phorbol Ester Induces the Transcriptional Stimulatory Activity of the SV40 Enhancer," Nature, vol. 323 (6088), Oct. 1986, pp. 555-558.

Imler et al., "Negative Regulation Contributes to Tissue Specificity of the Immunoglobulin Heavy-chain Enhancer," Molecular and Cellular Biology, vol. 7(7), Jul. 1987, pp. 2558-2567.

Imperiale et al., "Adenovirus 5 E2 Transcription Unit: an E1A-inducible Promoter With an Essential Element That Functions

(56) References Cited

OTHER PUBLICATIONS

Independently of Position or Orientation," Molecular and Cellular Biology, vol. 4(5), May 1984, pp. 875-882.
Innis et al., "DNA Sequencing With Thermus Aquaticus DNA Polymerase and Direct Sequencing of Polymerase Chain Reaction-amplified DNA," Proceedings of the National Academy of Sciences of the United States of America, vol. 85(24), Dec. 1988, pp. 9436-9440.
Inouye et al., "Up-promoter Mutations in the Ipp Gene of *Escherichia coli*," Nucleic Acids Research, vol. 13(9), Mar.-Apr. 1985, pp. 3101-3109.
Intention to Grant dated Apr. 13, 2016 in European Patent Application No. 10835567 .8.
Intention to Grant dated Aug. 9, 2016 in European Patent Application No. 12796050.8.
Intention to Grant dated Sep. 8, 2016, issued on the European Patent Application No. 10835567.8.
International Preliminary Report on Patentability for Application No. PCT/IB2010/003396, dated Jun. 21, 2012, 8 pages.
International Preliminary Report on Patentability for Application No. PCT/CA2012/050893, dated Jun. 25, 2015, 9 pages.
International Preliminary Report on Patentability for Application No. PCT/CA2014/050118, dated Sep. 3, 2015, 10 pages.
International preliminary report on patentability dated Dec. 23, 2015 in PCT/CA2014/050563.
International preliminary report on patentability dated Dec. 27, 2013 in PCT/CA2012/050385.
International Search Report and Written Opinion dated Jun. 28, 2010 in PCT Application No. PCT/CA2010/000379.
International Search Report and Written Opinion dated Aug. 24, 2012 in PCT Application No. PCT/CA2012/050385.
International Search Report and Written Opinion for Application No. PCT/CA2012/050893, dated Aug. 28, 2013, 13 pages.
International Search Report and Written Opinion for Application No. PCT/CA2014/050118, dated Jun. 11, 2014, 16 pages.
International Search Report and Written Opinion for Application No. PCT/IB2010/003396, dated Jul. 12, 2011, 11 pages.
International Search Report and Written Opinion dated Aug. 28, 2014 in PCT Application No. PCT/CA2014/050534.
International Search Report and Written Opinion dated Aug. 29, 2014 in PCT Application No. PCT/CA2014/050563.
International Search Report and Written Opinion dated Dec. 13, 2018 in PCT Application No. PCTCA2018/051329.
International Search Report and Written Opinion dated Sep. 5, 2017 in PCT Application No. PCTIB2017/000622.
Irie et al., "Human Monoclonal Antibody to Ganglioside GM2 for Melanoma Treatment", The Lancet, vol. 333, Issue 8641, Apr. 1989, 2 pages.
Irie et al., "Modifications of the PSAP Region of the Matrix Protein Lead to Attenuation of Vesicular Stomatitis Virus in Vitro and in Vivo," Journal of General Virology, vol. 88 (Pt. 9), Sep. 2007, pp. 2559-2567.
Irie et al., "Regression of Cutaneous Metastatic Melanoma by Intralesional Injection With Human Monoclonal Antibody to Ganglioside GD2," Proceedings of the National Academy of Sciences of the United States of America, vol. 83(22), Nov. 1986, pp. 8694-8698.
Israel Patent Application No. 240723, Office Action dated May 16, 2018—English Translation.
Jakobovits et al., "A Discrete Element 3' of Human Immunodeficiency Virus 1 (HIV-1) and HIV-2 mRNA Initiation Sites Mediates Transcriptional Activation by an HIV Trans Activator," Molecular and Cellular Biology, vol. 8(6), Jun. 1988, pp. 2555-2561.
Jameel et al., "The Human Hepatitis B Virus Enhancer Requires Trans-acting Cellular Factor{S} for Activity," Molecular and Cellular Biology, vol. 6(2), Feb. 1986, pp. 710-715.
Japanese Patent Application No. 2015-546782, Office Action and English Translation dated Nov. 8, 2016.
Japanese Patent Application No. 2015-558314, Notice of Reasons for Rejection and English Translation dated Nov. 21, 2017.
Jaynes et al., "The Muscle Creatine Kinase Gene is Regulated by Multiple Upstream Elements, Including a Muscle-Specific Enhancer," Molecular and Cellular Biology, vol. 8(1), Jan. 1988, pp. 62-70.
Jia, Bin, et al. "Immunization with single-cycle SIV significantly reduces viral loads after an intravenous challenge with SIVmac239." PLoS pathogens 5, No. 1 (2009): e1000272.
Johnson et al., "Protein Kinase Inhibitor Prevents Pulmonary Edema in Response to H2O2," American Journal of Physiology, vol. 256 (4 Pt 2), Apr. 1989, pp. H1012-H1022.
Ju et al., "Interleukin-18 Gene Transfer Increases Antitumor Effects of Suicide Gene Therapy Through Efficient Induction of Antitumor Immunity," Gene Therapy, vol. 7(19), Oct. 2002, pp. 1672-1679.
Kadesch et al., "Effects of the Position of the Simian Virus 40 Enhancer on Expression of Multiple Transcription Units in a Single Plasmid," Molecular and Cellular Biology, vol. 6(7), Jul. 1986, pp. 2593-2601.
Kaeppler et al., "Silicon Carbide Fiber-Mediated DNA Delivery Into Plant Cells," Plant cell reports, vol. 9(8), Dec. 1990, pp. 415-418.
Kaneda et al., "Increased expression of DNA cointroduced with nuclear protein in adult rat liver.," Science, vol. 243 (4889), Jan. 1989, pp. 375-378.
Karin et al., Metal-Responsive Elements Act as Positive Modulators of Human Metallothionein-IIa Enhancer Activity, Molecular and Cellular Biology, vol. 7(2), Feb. 1987, pp. 606-613.
Katinka et al., "Expression of Polyoma Early Functions in Mouse Embryonal Carcinoma Cells Depends on Sequence Rearrangements in the Beginning of the Late Region," Cell, vol. 20(2), Jun. 1980, pp. 393-399.
Katinka et al., "Polyoma DNA Sequences Involved in Control of Viral Gene Expression in Murine Embryonal Carcinoma Cells," Nature, vol. 290(5808), Apr. 1981, pp. 720-722.
Kato et al., "Expression of hepatitis B virus surface antigen in adult rat liver," The Journal of biological chemistry, vol. 266(6), Feb. 1991, pp. 3361-3364.
Kaufman, Howard L., et al. "Oncolytic viruses: a new class of immunotherapy drugs." Nature reviews, Drug discovery vol. 14, No. 9, pp. 642-664, Sep. 2015.
Kaufman, Howard L., et al. "Phase II randomized study of vaccine treatment of advanced prostate cancer (E7897): a trial of the Eastern Cooperative Oncology Group." Journal of Clinical Oncology 22, No. 11 (2004): 2122-2132.
Kaufmann et al., "Safety and Immunogenicity of TA-HPV, A Recombinant Vaccinia Virus Expressing Modified Human Papillomavirus (HPV)-16 and HPV-18 E6 and E7 Gene in Women with Progressive Cervical Cancer," Clinical Cancer Research, Dec. 2002, vol. 8(12), pp. 3676-3685.
Kawamoto et al., "Identification of the Human Beta-Actin Enhancer and its Binding Factor," Molecular and Cellular Biology, vol. 8(1), Jan. 1988, pp. 267-272.
Kenter et al., Vaccination Against HPV-16 Oncoproteins for Vulvar Intraepithelial Neoplasia, The New England Journal of Medicine, Nov. 2009, vol. 361(19), pp. 1838-1847.
Kerr et al., "Apoptosis: A Basic Biological Phenomenon With Wide-ranging Implications in Tissue Kinetics.," British Journal of Cancer, vol. 26(4), Apr. 1972, pp. 239-257.
Kerschner et al., "Identification and Characterization of Bahia Grande, Reed Ranch and Muir Springs Viruses, Related Members of the Family Rhabdoviridae with Widespread Distribution in the United States," Journal of General Virology, vol. 67(6), Jun. 1986, pp. 1081-1089.
Palmiter et al., "Differential Regulation of Metallothionein-Thymidine Kinase Fusion Genes in Transgenic Mice and their Offspring," Cell, vol. 29(2), Jun. 1982, pp. 701-710.
Palmiter et al., "Dramatic Growth of Mice that Develop from Eggs Microinjected with Metallothionein-Growth Hormone Fusion Genes," Nature, vol. 300(5893), Dec. 1982, pp. 611-615.
Parato, Kelley A., et al. "Recent progress in the battle between oncolytic viruses and tumours." Nature Reviews Cancer 5, No. 12 (2005): 965.
Partial Supplementary European Search Report for Application No. EP14754562, dated Aug. 30, 2016, 9 pages.
Pearson "Silent Mutatations Speak Up" Nature News, Dec. 2006.

(56) References Cited

OTHER PUBLICATIONS

Pech et al., "Functional Identification of Regulatory Elements within the Promoter Region of Platelet-Derived Growth Faction 2," Molecular and Cellular Biology, vol. 9(2), Feb. 1989, pp. 396-405.
Pelletier et al., "Internal Initiation of Translation of Eukaryotic mRNA Directed by a Sequence Derived From Poliovirus RNA," Nature, vol. 334(6180), Jul. 1988, pp. 320-325.
Peng et al., "Development of a DNA Vaccine Targeting Human Papillomavirus Type 16 Oncoprotein E6," Journal of Virology, Aug. 2004, vol. 78(16), pp. 8468-8476.
Perez-Stable et al., "Roles of Fetal G-Gamma-Globin Promoter Elements and the Adult beta-Globin 3' Enhancer in the Stage-Specific Expression of Globin Genes," Molecular and Cellular Biology, vol. 10(3), Mar. 1990, pp. 1116-1125.
Phoung, Loi K., et al. "Use of a vaccine strain of measles virus genetically engineered to produce carcinoembryonic antigen as a novel therapeutic agent against glioblastoma multiforme." Cancer research 63, No. 1O (2003): 2462-2469.
Picard et al., "A Lymphocyte-Specific Enhancer in the Mouse Immunoglobulin k Gene," Nature, vol. 307, Jan. 1984, pp. 80-82.
Pietras et al., "Remission of Human Breast Cancer Xenografls on Therapy With Humanized Monoclonal Antibody to HER-2 Receptor and Dna-Reactive Drugs," Oncogene, vol. 17(17), Oct. 1998, pp. 2235-2249.
Pinkert et al., "An Albumin Enhancer Localed 10kb Upstream Functions Along With Its Promoter to Direct Efficient, Liver-specific Expression in Transgenic Mice," Genes and Development, vol. 1(3), May 1987, pp. 268-276.
Pinschewer et al., "Kinetics of Protective Antibodies are Determined by the Viral Surface Antigen," The Journal of Clinical Investigation, Oct. 2004, vol. 114(7), pp. 988-993.
Pinto, Arguinaldo R., et al. "Induction of CD8+ T cells to an HIV-1 antigen through a prime boost regimen with heterologous E1-deleted adenoviral vaccine carriers." The Journal of Immunology 171, No. 12 (2003): 6774-6779.
Pol et al., "Oncolytic Viruses: A Step Into Cancer Immunotherapy," Virus Adaptation and Treatment, vol. 4(1), 2012, pp. 1-21.
Pol et al., "Use of oncolytic rhabdoviruses as potent tumour vaccine boosters," Abstract 145, Association for Cancer mmunotherapy {CIMT) 10th Annual Meeting, Mainz, CIMT, vol. 10, May 23-25, 2012, p. 199, XP00818042.
Pol et al., "Maraba Virus as a Potent Oncolytic Vaccine Vector," Molecular Therapy, vol. 22(2), Oct. 2013, pp. 420-429.
Pol, Jonathan G. "Maraba Virus as a Potent Oncolytic Vaccine Vector" The American Society of Gene and Cell Therapy, vol. 22, No. 2, pp. 420-429, Feb. 2014.
Ponta et al., "Hormonal Response Region in the Mouse Mammary Tumor Virus Along Terminal Repeat Can Be Dissociated From the Proviral Promoter and Has Enhancer Properties," Proceedings of the National Academy of Sciences of the United States of America, vol. 82(4), Feb. 1985, pp. 1020-1024.
Porton et al., "Immunoglobulin Heavy-Chain Enhancer is Required to Maintain Transfecled y2A Gene Expression in a Pre-B-Cell Line," Molecular and Cellular Biology, vol. 10(3), Mar. 1990, pp. 1076-1083.
Power et al., "Carrier Cell-Based Delivery of an Oncolylic Virus Circumvents Antiviral Immunity," Molecular Therapy, vol. 15(1), Jan. 2007, pp. 123-130.
Purcell et al., "More Than One Reason to Rethink the Use of Peptides in Vaccine Design," Nature Reviews Drug Discovery, May 2007, vol. 6(5), pp. 404-414.
Qin et al., "Interferon-Beta Gene Therapy Inhibits Tumor Formation and Causes Regression of Established Tumors in Immune-Deficient Mice," Proceedings of the National Academy of Sciences of the United States of America, vol. 95 (24), Nov. 1998, pp. 14411-14416.
Queen et al., "Immunoglobulin Gene Transcription is Activated by Downstream Sequence Elements," Cell, vol. 3(3), Jul. 1983, pp. 741-748.
Quinn et al., "Multiple Components Are Required for Sequence Recognition of the AP1 Site in the Gibbon Ape Leukemia Virus Enhancer," Molecular and Cellular Biology, vol. 9(11), Nov. 1989, pp. 4713-4721.
Quispe-Tintaya et al., "Nontoxic Radioactive Listeria(at) is a Highly Effective Therapy Against Metastatic Pancreatic cancer," Proceedings of the National Academy of Sciences U.S.A, May 2013, vol. 110(21), pp. 8668-8673.
Rauschhuber et al., "New Insights into Stability of Recombinant Adenovirus Vector Genomes in Mammalian Cells," European Journal of Cell Biology, Jan. 2012, vol. 91(1 ), pp. 2-9.
Ravindranath et al., "Role of Gangliosides in Active Immunotherapy with Melanoma Vaccine," International Reviews of Immunology, vol. 7(4), Apr. 1991, pp. 303-329.
Redondo et al., "A T Cell-Specific Transcriptional Enhancer Within the Human T Cell Receptor delta Locus," Science, vol. 247(4947), Mar. 1990, pp. 1225-1229.
Reisman et al., "Induced Expression from the Moloney Murine Leukemia Virus Long Terminal Repeat during Differentiation of Human Myeloid Cells Is Mediated Through Its Transcriptional Enhancer," Molecular and Cellular Biology, vol. 9(8), Aug. 1989, pp. 3571-3575.
Resendez et al., "Identification of Highly Conserved Regulatory Domains and Protein-Binding Sites in the Promoters of the Rat and Human Genes Encoding the Stress-Inducible 78-Kilodalton Glucose-Regulated Protein," Molecular and Cellular Biology, vol. 8(10), Oct. 1988, pp. 4579-4584.
Restriction Requirement dated Jan. 14, 2014 in U.S. Appl. No. 13/514,837.
Restriction Requirement issued in U.S. Appl. No. 14/651,761 dated Sep. 9, 2016.
Riezebos-Brilman, A., et al. "A comparative study on the immunotherapeutic efficacy of recombinant Semliki Forest virus and adenovirus vector systems in a murine model for cervical cancer." Gene therapy 14, No. 24 (2007): 1695.
Rippe et al., "Regulatory Elements in the 5'-Flanking Region and the First Intron Contribute to Transcriptional Control of the Mouse Alpha 1 Type I Collagen Gene," Molecular and Cellular Biology, vol. 9(5), Molecular and Cellular Biology, pp. 2224-2227.
Ritchie, D. S., et al. "B-Lymphocytes Activated by CD40 Ligand Induce an Antigen-Specific Anti-Tumour Immune Response by Direct and Indirect Activation of CD8+ T-cells." Scandinavian journal of immunology 60, No. 6 (2004): 543-551.
Rittling et al., "AP-1/jun Binding Sites Mediate Serum Inducibility of the Human Vimentin Promoter," Nucleic Acids Research, vol. 17(4), Feb. 1989, pp. 1619-1633.
Rodriguez et al., "Regulated Expression of Nuclear Genes by T3 RNA Polymerase and lac Repressor, Using Recombinant Vaccinia Virus Vectors," Journal of Virology, vol. 64(10), Oct. 1990, pp. 4851-4857.
Roediger, Elizabeth K., et al. "Heterologous Boosting of Recombinant Adenoviral Prime Immunization With a Novel Vesicular Stomatitis Virus-vectored Tuberculosis Vaccine." Molecular Therapy 16, No. 6 (2008): 1161-1169.
Rose, Nina F., et al. "Glycoprotein exchange vectors based on vesicular stomatitis virus allow effective boosting and generation of neutralizing antibodies to a primary isolate of human immunodeficiency virus type 1." Journal of virology 74, No. 23 (2000): 10903-10910.
Rosen et al., "The Location of Cis-Acting Regulatory Sequences in the Human T Cell Lymphotropic Virus Type III (HTLV-111/LAV) Long Terminal Repeat," Cell, vol. 41(3), Jul. 1985, pp. 813-823.
Rosenberg et al., "Experience with the Use of High-Dose Interleukin-2 in the Treatment of 652 Cancer Patients", 109th Annual Meeting of the American Surgical Association, Colorado Springs, Colorado, Apr. 10-12, 1989, pp. 174-484.
Rosenberg et al., "Use of Tumor-Infiltrating Lymphocytes and Interleukin-2 in the Immunotherapy of Patients with Metastatic Melanoma," The New England Journal of Medicine, vol. 319, Dec. 1988, pp. 1676-1680.
Rudikoff, Stuart, et al. "Single amino acid substitution altering antigen-binding specificity." Proceedings of the National Academy of Sciences 79, No. 6 ( 1982): 1979-1983.

(56) References Cited

OTHER PUBLICATIONS

Russell et al., "Oncolytic Virotherapy," Nature Biotechnology, vol. 30(7), Jul. 2012, pp. 1-13.
Russian Patent Application No. 2015135890, Office Action dated Jun. 30, 2017—With English Translation.
Russian Patent Application No. 2015135890, Office Action and English Translation dated Nov. 17, 2017.
Sakai et al., "Hormone-Mediated Repression: A Negative Glucocorticoid Response Element From the Bovine Prolactin Gene," Genes and Development, vol. 2(9), Sep. 1988, pp. 1144-1154.
Sanjuan et al., "The Contribution of Epistasis to the Architecture of Fitness in an RNA Virus," Proceedings of the National Academy of Science USA, vol. 101(43), Oct. 2004, pp. 15376-15379.
Ferguson, Mark S., et al. "Systemic delivery of oncolytic viruses: hopes and hurdles." Advances in Virology 2012 (2012).
Ferran et al., "The Vesicular Stomatitis Virus Matrix Protein Inhibits Transcription From the Human Beta Interferon Promoter," The Vesicular Stomatitis Virus Matrix Protein Inhibits Transcription From the Human Beta Interferon Promoter, vol. 71(1), Jan. 1997, pp. 371-377.
Firak et al., "Minimal Transcriptional Enhancer of Simian Virus 40 Use a 74-Base-Pair Sequence That Has Interacting Domains," Molecular and Cellular Biology, vol. 6(11), Nov. 1986, pp. 3667-3676.
Foecking et al., "Powerful and Versatile Enhancer-promoter Unit for Mammalian Expression Vectors," Gene, vol. 45 (1), Feb. 1986, pp. 101-105.
Fourth Office Action issued on corresponding Chinese Patent Application No. 201080063490.X dated Jan. 22, 2015, with English translation.
Fraley et al., "The Sev System: a New Disarmed TI Plasmid Vector System for Plant Transformation," Bio Technology, vol. 3, Jul. 1985, pp. 629-635.
Frohman et al., "Rapid Production of Full-length CDNAs From Rare Transcripts: Amplification Using a Single Gene-specific Oligonucleolide Primer," Proceedings of the National Academy of Sciences of the United States of America, vol. 85(23), Dec. 1988, pp. 8998-9002.
Fu, Xinping, et al. "Incorporation of the B18R gene of vaccinia virus into an oncolytic herpes simplex virus improves antitumor activity." Molecular Therapy vol. 20, No. 10 (2012): 1871-1881.
Fuerst et al., "Eukaryotic Transient-expression System Based on Recombinant Vaccinia Virus That Synthesizes Bacteriophage T7 RNA Polymerase," Proceedings of the National Academy of Sciences of the United States of America, vol. 83(21), Nov. 1986, pp. 8122-8126.
Fujita et al., "Interferon-beta Gene Regulation: Tandemly Repealed Sequences of a Synthetic 6 bp Oligomer Function as a Virus-inducible Enhancer," Cell, vol. 49(3), May 1987, pp. 357-369.
Gilles et al., "A Tissue-specific Transcription Enhancer Element Is Located in the Major Intron of a Rearranged mmunoglobulin Heavy Chain Gene," Cell, vol. 33(3), Jul. 1983, pp. 717-728.
Gloss et al., "The Upstream Regulator Region of the Human Papilloma Virus-16 Contains an E2 Protein-independen Enhancer Which Is Specific for Cervical Carcinoma Cells and Regulated by Glucocorticoid Hormones," The EMBO Journal, vol. 6(12), Dec. 1987, pp. 3735-3743.
Godbout et al., "Fine-structure Mapping of the Three Mouse Alpha-fetoprotein Gene Enhancers," Molecular and Cellular Biology, vol. 8(3), Mar. 1988, pp. 1169-1178.
Gomes et al., "Steap Proteins: from structure to applications in Cancer Therapy," Molecular Cancer Research, May 2012, vol. 10 (5), pp. 573-587.
Goodbourn et al., "The Human Beta-interferon Gene Enhancer Is Under Negative Control," Cell, vol. 45(4), May 1986, pp. 601-610.
Goodbourn et al., "Overlapping Positive and Negative Regulatory Domains of the Human Beta-interferon Gene," Proceedings of the National Academy of Sciences of the United States of America, vol. 85(5), Mar. 1988, pp. 1447-1451.

Gopal et al., "Gene Transfer Method for Transient Gene Expression, Stable Transformation, and Cotransformation of Suspension Cell Cultures," Molecular and Cellular Biology, vol. 5(5), May 1985, pp. 1188-1190.
Graham et al., "A New Technique for the Assay of Infectivity of Human Adenovirus 5 DNA," Virology, vol. 52(2), Apr. 1973, pp. 456-467.
Greene et al., "HIV-1, HTLV-1 and Normal T-cell Growth: Transcriptional Strategies and Surprises," Immunology Today, vol. 10(8), Aug. 1989, pp. 272-278.
Gromeier et al., "Intergenenc Poliovirus Recombinants for the Treatment of Malignant Glioma," Proceedings of the National Academy of Sciences of the United States of America, vol. 97(12), Jun. 2000, pp. 6803-6808.
Grosschedl et al., "Cell-Type Specificity of Immunoglobulin Gene Expression Is Regulated by at Least Three DNA Sequence Elements," Cell, vol. 41(3), Jul. 1985, pp. 885-897.
Grote et al., "Live Attenuated Measles Virus Induces Regression of Human Lymphoma Xenografts in Immunodeficient Mice," Blood, vol. 97(12), Jun. 2001, pp. 3746-3754.
Guruprasad et al., "Correlation Between Stability of a Protein and Its Dipeptide Composition: A Novel Approach for Predicting in Vivo Stability of a Protein From Its Primary Sequence," Protein Engineering, Dec. 1990, vol. 4(2), pp. 155-161.
Hanibuchi et al., "Therapeutic Efficacy of Mouse-Human Chimeric Anti-ganglioside GM2 Monoclonal Antibody Against Multiple Organ Micrometastases of Human Lung Cancer in NK Cell-Depleted Scid Mice," International Journal of Cancer, vol. 78(4), Nov. 1998, pp. 480-485.
Harland et al., "Translation of mRNA Injected Into Xenopus Oocytes Is Specifically Inhibited by Antisense RNA," The Journal of Cell Biology, vol. 101(3), Sep. 1985, pp. 1094-1099.
Hasegawa, Kosei, et al. "Dual therapy of ovarian cancer using measles viruses expressing carcinoembryonic antigen and sodium iodide symporter." Clinical Cancer Research 12, No. 6 (2006): 1868-1875.
Haslinger et al., "Upstream Promoter Element of the Human Metalltlhionein-iia Gene Can Act Like an Enhancer Element," Proceedings of the National Academy of Sciences of the United States of America, vol. 82(24 ), Dec. 1985, pp. 8572-8576.
Hauber et al., "Mutational Analysis of the Trans-activation-responsive Region of the Human Immunodeficiency Virus Type I Long Terminal Repeat," Journal of Virology, vol. 62(3), Mar. 1988, pp. 673-679.
Heiber, Joshua F. "Characterization and Development of Vesicular Stomatitis Virus for Use as an Oncolytic Vector." Open Access Dissertations, Paper 600 (2011 ).
Heideman et al., "Oncolytic Adenovirus Expressing a p53 variant Resistant to Degradation by HPV E6 Protein Exhibits Potent and Selective Replication in Cervical Cancer," Molecular Therapy, Dec. 2005, vol. 12(6), pp. 1083-1090.
Heise et al., "An Adenovirus E1A Mutant That Demonstrates Potent and Selective Systemic Anti-Tumoral Efficacy," Nature Medicine, vol. 6(10), Oct. 2000, pp. 1134-1139.
Hellstrand et al., "Histamine and Cytokine Therapy," Acta Oncologica, vol. 37(4), 1998, pp. 347-353.
Hen et al., "A Mutated Polyoma Virus Enhancer Which Is Active in Undifferentiated Embryonal Carcinoma Cells Is Not Repressed by Adenovirus-2 E1A Products," Nature, vol. 321(6067), May 1986, pp. 249-251.
Hensel et al., "PMA-responsive 5' Flanking Sequences of the Human TNF Gene," Lymphokine Research, vol. 8(3), Feb. 1989, pp. 347-351.
Herr et al., "The SV40 Enhancer Is Composed of Multiple Functional Elements That Can Compensate for One Another," Cell, vol. 45(3), May 1986, pp. 461-470.
Hilton et al., "Saturation Mutagenesis of the WSxWs Motif of the Erythropoietin Receptor," The Journal of Biological Chemistry, vol. 271(9), Mar. 1996, pp. 4699-4708.
Hirochika et al., "Enhancers and Trans-Acting E2 Transcriptional Factors of Papillomaviruses," Journal of Virology, vol. 61(8), Aug. 1987, pp. 2599-2606.

(56) References Cited

OTHER PUBLICATIONS

Hirsch et al., "Identification of Positive and Negative Regulatory Elements Governing Cell-Type-Specific Expression of the Neural Cell Adhesion Molecule Gene," Molecular and Cellular Biology, vol. 10(5), May 1990, pp. 1959-1968.
Hoffmann et al., "Fusion-active Glycoprotein G Mediates the Cytotoxicity of Vesicular Stomatitis Virus M Mutants Lacking Host Shut-off Activity," The Journal of General Virology, vol. 91 (PI 11), Nov. 2010, pp. 2782-2793.
Holbrook et al., "cis-Acling Transcriptional Regulatory Sequences in the Gibbon Ape Leukemia Virus (GALV) Long Terminal Repeat," Virology, vol. 157(1), Mar. 1987, pp. 211-219.
Holden et al., "The Molecular Structure of Insecticyanin From the Tobacco Hornworm Manduca Sexta L. At 2.6 A Resolution," The Embo Journal, vol. 6(6), Jun. 1987, pp. 1565-1570.
Horlick et al., "The Upstream Muscle-specific Enhancer of the Rat Muscle Creatine Kinase Gene Is Composed of Multiple Elements," Molecular and Cellular Biology, vol. 9(6), Jun. 1989, pp. 2396-2413.
Hu, Wenxian, et al. "Redirecting adaptive immunity against foreign antigens to tumors for cancer therapy." Cancer Biology & Therapy, vol. 6, No. 11, pp. 1773-1779, Nov. 2007.
Huang et al., "Glucocorticoid Regulation of the HA-MuSV P21 Gene Conferred by Sequences From Mouse Mammary, Tumorvirus," Cell, vol. 27 (2 PI 1), Dec. 1981, pp. 245-255.
Hubert et al., "Steap: A Prostate-specific Cell-surface Antigen Highly Expressed in Human Prostate Tumors," Proceedings of the National Academy of Sciences of the United States of America, vol. 96(25), Dec. 1999, pp. 14523-14528.
Hug et al., "Organization of the Murine Mx Gene and Characterization of Its Interferon-and Virus-inducible Promoter," Molecular and Cellular Biology, vol. 8(8), Aug. 1988, pp. 3065-3079.
Hui et al., "Pathways for Potentiation of Immunogenicity During Adjuvant-assisled Immunizations With Plasmodium Falciparum Major Merozoite Surface Protein 1," Infection and Immunity, vol. 6 (11), Nov. 1998, pp. 5329-5536.
Humme et al., "The Ebv Nuclear Antigen 1 (EBNA1) Enhances B Cell Immortalization Several Thousandfold," Proceedings of the National Academy of Sciences of the United States of America, vol. 100(19), Sep. 2003, pp. 10989-10994.
Hung, Chien-Fu, et al. "Antigen-specific immunotherapy of cervical and ovarian cancer." Immunological reviews 222, No. 1 (2008): 43-69.
Hwang et al., "Characterization of the S-phase-specific Transcription Regulatory Elements in a DNA Replication-Independent Testis-specific H2B (TH2B) Histone Gene," Molecular and Cellular Biology, vol. 10(2), Feb. 1990, pp. 585-592.
Abschuetz et al., "Oncolytic Murine Autonomous Parvovirus, a Candidate Vector for Glioma Gene Therapy, Is Innocuous to Normal and Immunocompetent Mouse Glial Cells," Cell and Tissue Research, vol. 325(3), May 2006, pp. 423-426.
Alcami et al., Vaccinia Virus Encodes a Soluble Type I Interferon Receptor of Novel Structure and Broad Species Specificity, Cell, vol. 61, May 1995, pp. 551-560.
Alcami, Antonio, et al. "The vaccinia virus soluble alpha/beta interferon (IFN) receptor binds to the cell surface and protects cells from the antiviral effects of IFN." Journal of Virology, vol. 74, No. 23, pp. 11230-11239, Dec. 2000.
Almendro et al., "Cloning of the Human Platelet Endothelial Cell Adhesion Molecule-1 Promoter and its Tissue-Specific Expression", The Journal of Immunology, vol. 157(12), Dec. 1996, pp. 5411-5421.
Altomonte et al., "Enhanced Oncolytic Potency of Vesicular Stomatitis Virus Through Vector-mediated Inhibition of Nk and Nkt Cells", Cancer Gene Therapy, vol. 16(3), Mar. 2009, pp. 266-278.
Angel et al., "12-0-Tetradecanoyi-Phorboi-13-Acetate Induction of the Human Collagenase Gene Is Mediated by an Inducible Enhancer Element Located in the 5'-Fianking Region," Molecular and Cellular Biology, vol. 7(6), Jun. 1987, pp. 2256-2266.

Angel et al., "Phorbol Ester-Inducible Genes Contain a Common Cis Element Recognized by a TPA-Modulaled Trans-Action Factor," Cell, vol. 49(6), Jun. 1987, pp. 729-739.
Atherton et al., "Evolution of Oncolytic Viruses: Novel Strategies for Cancer Treatment," Immunotherapy, Nov. 2013, vol. 5(11), pp. 1191-1206.
Attwood et al., "The Babel of Bioinforrnatics", Science, 2000, vol. 290, No. 5491, pp. 471-473.
Austin-Ward et al., "Gene Therapy and Its Applications," Revista Medica De Chile, vol. 126(7), Jul. 1998, pp. 838-845.
Australian Patent Application No. AU2014221143, Office Action dated Jan. 25, 2018.
Bachmann, Martin F., et al. "Immunization with recombinant protein: conditions for cytotoxic T cell and/or antibody induction." Medical microbiology and immunology vol. 183, No. 6 (1994): 315-324.
Bajorin et al, "Comparison of Criteria for Assigning Germ Cell Tumor Patients to "Good Risk" and "Poor Risk" Studies," Journal of Clinical Oncology, vol. 6(5), May 1988, pp. 786-792.
Baker et al., "Protein structure and structural genomics", Science, 2001, vol. 294, No. 5540, pp. 93-96.
Bakhshi et al, "Cloning the Chromosomal Breakpoint of T{14;18} Human Lymphomas: Clustering Around Jh on Chromosome 14 and Near a Transcriptional Unit on 18," Cell, vol. 41(3), Jul. 1985, pp. 899-906.
Banerjee, Amiya K. "Transcription and replication of rhabdoviruses." Microbiological reviews.vol. 51, No. 1, pp. 66-87, Mar. 1987.
Banerji et al., "Expression of a Beta-Globin Gene Is Enhanced by Remote Sv40 DNA Sequences," Cell, vol. 27(2 Pt 1), Dec. 1981, pp. 299-308.
Barber, Glen N. "Vesicular stomatitis virus as an oncolytic vector." Viral immunology, vol. 17, No. 4 (2004): 516-527.
Barrios et al., "TriVax-HPV: An Improved Peptide-Based Therapeutic Vaccination Strategy Against Human Papillomavirus-Induced Cancers," Cancer Immunol Immunother, Apr. 2012, vol. 61(8), pp. 1307-1317.
Beglin et al., "Human papillomaviruses and the interferon response," Journal of Interferon & Cytokine Research, Sep. 2009, vol. 29 (9), pp. 629-635.
Bellone et al., "Relevance of the Tumor Antigen in the Validation of Three Vaccination Strategies for Melanoma," The Journal of Immunology, Sep. 2000, vol. 165(5), pp. 2651-2656.
Bergmann et al., "A Genetically Engineered Influenza A Virus with ras-Dependent Oncolytic Properties," Cancer Research, vol. 61(22), Nov. 2001, pp. 8188-8193.
Berkhout et al., "Tat Trans-Activates the Human Immunodeficiency Virus Through a Nascent RNA Target," Cell, vol. 59(2), Oct. 1989, pp. 273-282.
Beyer et al., "Glycoprotein C [Lymphocytic choriomeningitis mammarenavirus]—Protein—NCBI," Genbank Accession #CAC01231. 1,Jan. 2001, 1 page.
Beyer et al., "Oncoretrovirus and Lentivirus Vectors Pseudotyped with Lymphocytic Choriomeningitis Virus Glycoprotein: Generation, Concentration, and Broad Host Range," Journal of Virology, vol. 76(3), Feb. 2002, pp. 1488-1495.
Blanar et al., "A Gamma-interferon-induced Factor That Binds the Interferon Response Sequence of the MHC Class Gene, H-2kb," The EMBO Journal, vol. 8(4), Apr. 1989, pp. 1139-1144.
Blechacz, Boris, and Stephen J. Russell. "Measles virus as an oncolytic vector platform." Current gene therapy, vol. 8, No. 3 (2008): 162-175.
Bodine et al., "An Enhancer Element Lies 3' to the Human a Gamma Globin Gene," The EMBO Journal, vol. 6(10), Oct. 1987, pp. 2997-3004.
Boritz, Eli, et al. "Replication-competent rhabdoviruses with human immunodeficiency virus type 1 coats and green fluorescent protein: entry by a pH-independent pathway." Journal of virology, vol. 73, No. 8 (1999): 6937-6945.
Boshart et al., "A Very Strong Enhancer is Localed Upstream of an Immediate Early Gene of Human Cytomegalovirus," Cell, vol. 41(2), Jun. 1985, pp. 521-530.

(56) References Cited

OTHER PUBLICATIONS

Bosze et al., "A Transcriptional Enhancer With Specificity for Erythroid Cells Is Localed in the Long Terminal Repeat of the Friend Murine Leukemia Virus," The EMBO Journal, vol. 5(7), Jul. 1986, pp. 1615-1623.

Botstein et al, "Strategies and Applications of in Vitro Mutagenesis," Science, vol. 229(4719), Sep. 1985, pp. 1193-1201.

Braddock et al., "HIV-1 TAT "Activates" Presynthesized RNA in the Nucleus," Cell, vol. 58(2), Jul. 1989, pp. 269-279.

Braisted et al., "Minimizing a Binding Domain From Protein A," Proceedings of the National Academy of Sciences of the United States of America, vol. 93(12), Jun. 1996, pp. 5688-5692.

Bridle et al. "Potentiating cancer immunotherapy using an oncolytic virus," Molecular Therapy 2010, vol. 18, No. 8, pp. 1430-1439.

Bridle et al., "Oncolytic Vesicular Stomatitis Virus Quantitatively and Qualitatively Improves Primary CD8+ T-Cell Responses to Anticancer Vaccines," Oncoimmunology, Aug. 2013, vol. 2(8), pp. 1-12.

Bridle et al., "Immunotherapy Can Reject Intracranial Tumor Cells Without Damaging the Brain Despite Sharing the Target Antigen," Journal of Immunology, vol. 184(8), Apr. 2010, pp. 4269-4275.

Bridle et al., Vesicular Stomatitis Virus as a Novel Cancer Vaccine Vector to Prime Antitumor Immunity Amenable le Rapid Boosting With Adenovirus, Molecular Therapy, vol. 17(10), Oct. 2009, pp. 1814-1821.

Bruggen et al., "Database of T Cell-Defined Human Tumor Antigens: The 2013 Update," Cancer Immunity, vol. 13, Jul. 2013, pp. 15.

Brun et al., "Identification of Genetically Modified Maraba Virus as an Oncolytic Rhabdovirus," Molecular Therapy, vol. 18(8), Jun. 2010, pp. 1440-1449.

Bukowski et al., "Signal Transduction Abnormalities in T Lymphocytes From Patients With Advanced Renal Carcinoma: Clinical Relevant and Effects of Cytokine Therapy," Clinical Cancer Research, vol. 4 (10), Oct. 1998, pp. 2337-2347.

Bulla et al., "The Hepatitis B Virus Enhancer Modulates Transcription of the Hepatitis B Virus Surface Antigen Gene From an Internal Location," Journal of Virology, vol. 62(4), Apr. 1988, pp. 1437-1441.

Burke, "Virus therapy for bladder cancer," Cytokine & Growth Factor Reviews, vol. 21, No. 2-3 pp. 99-102 (2010).

Burton et al., "Human Antibodies from Combinatorial Libraries," Advances in Immunology, vol. 57, 1994, pp. 191-280.

Campbell et al., "Functional Analysis of the Individual Enhancer Core Sequences of Polyomavirus: Cell-specific Uncoupling of Ona Replication From Transcription," Molecular and Cellular Biology, vol. 8(5), May 1988, pp. 1993-2004.

Campere et al., "Postnatal Repression of the Alpha-Fetoprotein Gene Is Enhancer Independent," Genes and Development, vol. 3(4), Feb. 1989, pp. 537-546.

Campo et al., "Transcriptional Control Signals in the Genome of Bovine Papillomavirus Type 1," Nature, vol. 303 (5912), May 1983, pp. 77-80.

Carbonelli et al., "A Plasmid Vector for Isolation of Strong Promoters in *Escherichia coli*," FEMS Microbiology Letters, vol. 177(1), Aug. 1999, pp. 75-82.

Cary et al., "Oncolytic Vesicular Stomatitis Virus Induces Apoptosis in U87 Glioblastoma Cells by a Type II Death Receptor Mechanism and Induces Cell Death and Tumor Clearance In Vivo," Journal of Virology, vol. 85(12), Jun. 2011, pp. 5708-5717.

Celander et al., "Glucocorticoid Regulation of Murine Leukemia Virus Transcription Elements Is Specified by Determinants Within the Viral Enhancer Region," Journal of Virology, vol. 6(2), Feb. 1987, pp. 269-275.

Tsujimoto et al., "Analysis of the Structure, Transcripts, and Protein Products of bcl-2, the Gene Involved in Human Follicular Lymphoma," Proceedings of the National Academy of Sciences of the United States of America, vol. 83(14), Jul. 1986, pp. 5214-5218.

Tsujimoto et al., "Clustering of Breakpoints on Chromosome 11 in Human B-Cell Neoplasms With the T(11 ;14) Chromosome Translocation," Nature, vol. 315(6017), May 1985, pp. 340-343.

Tsumaki et al., "Modular Arrangement of Cartilage- and Neural Tissue-specific Cis-elements in the Mouse Alpha2(XI) Collagen Promoter," vol. 273(36), Sep. 1998, pp. 22861-22864.

Tyler et al., "Neural Stem Cells Target Intracranial Glioma to Deliver an Oncolytic Adenovirus in Vivo," Gene Therapy, vol. 16(2), Feb. 2009, pp. 262-278.

U.S. Appl. No. 13/257,115, Declaration under 37 C.F.R. 1.132 dated Aug. 12, 2013.

U.S. Appl. No. 14/651,761, Restriction Requirement dated Sep. 9, 2016.

U.S. Appl. No. 14/651,761 Non-Final Office Action, dated Jan. 30, 2017.

Unno et al., "Oncolytic Viral Therapy for Cervical and Ovarian Cancer Cells by Sindbis Virus AR339 Strain," Clinical Cancer Research, vol. 11(12), Jun. 2005, pp. 4553-4560.

Usdin et al., "SP6 RNA Polymerase Containing Vaccinia Virus for Rapid Expression of Cloned Genes in Tissue Culture," Biotechniques, vol. 14(2), Feb. 1993, pp. 222-224.

Vaccari, Monica, et al. "Reduced protection from simian immunodeficiency virus SIVmac251 infection afforded by memory CD8+ T cells induced by vaccination during CD4+ T-cell deficiency." Journal of virology 82, No. 19 (2008): 9629-9638.

Van Der Burg, et al. "Pre-clinical safety and efficacy of TA-CIN, a recombinant HPV16 L2E6E7 fusion protein vaccine, in homologous and heterologous prime-boost regimens." Vaccine, vol. 19, No. 27, pp. 3652-3660, Jun. 2001.

Van Duikeren et al., Vaccine-Induced Effector-Memory CD8+ T Cell Responses Predict Therapeutic Efficacy Against Tumors, The Journal of Immunology, Oct. 2012, vol. 189(7), pp. 3397-3403.

Van Poelgeest et al., "HPV16 Synthetic Long Peptide (HPV16-SLP) Vaccination Therapy of Patients with Advanced or Recurrent HPV16-Induced Gynecological Carcinoma, A Phase II Trial," Journal of Translational Medicine, Apr. 2013, vol. 11, pp. 1-14.

Vannice et al., "Properties of the Human Hepatitis B Virus Enhancer: Position Effects and Cell-type Nonspecificity," Journal of Virology, vol. 62(4), Apr. 1988, pp. 1305-1313.

Vasseur et al., "Isolation and Characterization of Polyoma Virus Mutants Able to Develop in Embryonal Carcinoma Cells," Proceedings of the National Academy of Sciences of the United States of America, vol. 77(2), Feb. 1980, pp. 1068-1072.

Vigil, Adam, et al. "Recombinant Newcastle disease virus as a vaccine vector for cancer therapy." Molecular Therapy 16, No. 11 (2008): 1883-1890.

Vigneron, Nathalie, et al. "Database of T cell-defined human tumor antigens: the 2013 update." Cancer Immunity Archive, vol. 13, No. 3, p. 15, Jul. 2013.

Vile, Richard, et al. "The oncolytic virotherapy treatment platform for cancer: unique biological and biosafety points to consider." Cancer gene therapy 9, No. 12 (2002): 1062.

Walboomers et al., "Human Papillomavirus Is a Necessary Cause of Invasive Cervical Cancer Worldwide," The Journal of pathology, vol. 189(1), 1999, pp. 12-19.

Walker et al., "Strand Displacement Amplification-An Isothermal, in Vitro DNA Amplification Technique," Nucleic Acids Research, vol. 20(7), Apr. 1992, pp. 1691-1696.

Wall et al., "Targeting Tumors with Salmonella Typhimurium—Potential for Therapy," Oncotarget, Dec. 2010, vol. 1(8), pp. 721-728.

Wang et al., "SV40 Enhancer-Binding Factors Are Required at the Establishment but Not the Maintenance Step of the Enhancer-Dependent Transcriptional Activation," Cell, vol. 47(2), Oct. 1986, pp. 241-247.

Wang et al., "Selective Targeting of HPV-16 E6/E7 in Cervical Cancer Cells with a Potent Oncolytic Adenovirus and its Enhanced Effect with Radiotherapy in Vitro and Vivo," Cancer Letters, May 2010, vol. 291(1), pp. 67-75.

Warren et al., "A Rapid Screen of Active Site Mutants in Glycinamide Ribonucleotide Transformylase," Biochemistry vol. 35(27), Jul. 1996, pp. 8855-8862.

(56) References Cited

OTHER PUBLICATIONS

Watson et al., "Targeted Transduction Patterns in the Mouse Brain by Lentivirus Vectors Pseudotyped with VSV, Ebola, Mokola, LCMV, or MuLV Envelope Proteins," Molecular Therapy, vol. 5(5), May 2002, pp. 528-537.
Watson et al., "Transduction of the Choroid Plexus and Ependyma in Neonatal Mouse Brain by Vesicular Stomatitis Virus Glycoprotein-pseudotyped Lentivirus and Adena-associated Virus Type 5 Vectors," Human Gene Therapy, vol. 16(1), Jan. 2005, pp. 49-56.
Weber et al., "An SV40 "Enhancer Trap" Incorporates Exogenous Enhancers or Generates Enhancers From Its Own Sequences," Cell, vol. 36(4), Apr. 1984, pp. 983-992.
Weinberger et al., "Localization of a Repressive Sequence Contributing to B-Cell Specificity in the Immunoglobulin Heavy-Chain Enhancer," Molecular and Cellular Biology, vol. 8(2), Feb. 1988, pp. 988-992.
Wells et al., "Selectivity and Antagonism of Chemokine Receptors," Journal of Leukocyte Biology, vol. 59(1), Jan. 1996, pp. 53-60.
Whelan et al., "Efficient Recovery of Infectious Vesicular Stomatitis Virus Entirely From cDNA Clones," Proceedings of the National Academy of Sciences of the United States of America, vol. 92(18), Aug. 1995, pp. 8388-8392.
Wick et al., "A Novel, Broad Spectrum Therapeutic HPV Vaccine Targeting the E7 Proteins of HPV16, 18, 31, 45 and 52 that Elicits Potent E7-Specific CD8T Cell Immunity and Regression of Large, Established, E7-Expressing TC-1 Tumors," Vaccine, Oct. 2011, vol. 29(44), pp. 7857-7866.
Wieking et al., "A Non-Oncogenic HPV 16 E6/E7 Vaccine Enhances Treatment of HPV Expressing Tumors," Cancer Gene Therapy, Oct. 2012, vol. 19(10), pp. 667-674.
Winoto et al., "Alpha Beta Lineage-Specific Expression of the Alpha T Cell Receptor Gene by Nearby Silencers," Cell, vol. 59(4), Nov. 1989, pp. 649-655.
Wollmann et al., "Some Attenuated Variants of Vesicular Stomatitis Virus Show Enhanced Oncolytic Activity against Human Glioblastoma Cells relative to Normal Brain Cells," Journal of Virology, vol. 84(3), Feb. 2010, pp. 1563-1573.
Wollmann et al., "Oncolytic Virus Therapy for Glioblastoma Multiforme," The Cancer Journal, vol. 18(1), Jan. 2012, pp. 69-81.
Wong et al., "Appearance of Beta-Lactamase Activity in Animal Cells Upon Liposome-mediated Gene Transfer," Gene, vol. 10(2), 1980, pp. 87-94.
Wood et al., "Cancer Immunotherapy using Listeria Monocytogenes and Listerial Virulence Factors," Immunologic Research, Oct. 2008, vol. 42(1), pp. 233-245.
Wu et al., "CCR5 Levels and Expression Pattern Correlate With Infectability by Macrophage-tropic HIV-1, in Vitro," The Journal of Experimental Medicine, vol. 185(9), May 1997, pp. 1681-1691.
Yan et al., "Induction of Antitumor Immunity in Vivo Following Delivery of a Novel HPV-16 DNA Vaccine Encoding an E6/E7 Fusion Antigen," Vaccine, Jan. 2009, vol. 27(3), pp. 431-440.
Yelton et al., "Affinity Maturation of the Br96 Anti-Carcinoma Antibody by Codon-based Mutagenesis," Journal of Immunology, vol. 155(4), Aug. 1995, pp. 1994-2004.
Young et al., "Epstein-Barr Virus: 40 Years on," Nature Reviews-Cancer, vol. 4(10), Oct. 2004, pp. 757-768.
Yu, Yong A., Qian Zhang, and Aladar A. Szalay. "Establishment and characterization of conditions required for tumor colonization by intravenously delivered bacteria." Biotechnology and bioengineering 100, No. 3 (2008): 567-578.
Yutzey et al., "An Internal Regulatory Element Controls Troponin I Gene Expression," Molecular and Cellular Biology, vol. 9(4), Apr. 1989, pp. 1397-1405.
Zhang et al., "Oncolytic Therapeutic Potency of Farmington and Modified Maraba Virus in Immunocompetent Intracranial Glioma Models and in Mice Bearing Human Brain Tumor Initiating Cells Models," Neuro-Oncology, vol. 13 (Suppl 3), Oct. 2011, pp. iii107-iii120.

Zhao-Emonet et al., "Deletional and Mutational Analyses of the Human CD4 Gene Promoter: Characterization of a Minimal Tissue-Specific Promoter," Biochimica Et Biophysica Acta, vol. 1442 (2-3), Nov. 1998, pp. 109-119.
Zheng et al., "ATP-Binding Site of Human Brain Hexokinase as Studied by Molecular Modeling and Site-Directed Mutagenesis," Biochemistry, vol. 35(40), Oct. 1996, pp. 13157-13164.
Zur Hausen et al., "Papillomavirus Infections-A Major Cause of Human Cancers," Biochimica El Biophysica Acta, vol. 1288(2), Oct. 1996, pp. F55-F78.
Zwaveling et al., "Established Human Papillomavirus Type 16-Expressing Tumors Are Effectively Eradicated Following Vaccination With Long Peptides," The Journal of Immunology, Jul. 2002, vol. 169(1), pp. 350-358.
Office Action issued on Mexican Patent Application No. MX/a/2012/006508 dated Feb. 27, 2015, with English summary.
Office Action dated May 28, 2015 in Chinese Patent Application No. 201080022270.2 (English translation).
Office Action issued against corresponding European Patent Application No. 10835567.8 dated Jun. 16, 2015.
Office Action dated Jun. 25, 2015 in U.S. Appl. No. 13/257,115.
Office Action issued on the corresponding Russian Patent Application No. 2015128078 dated Oct. 13, 2015, with English summary.
Office Action dated Oct. 30, 2015 in U.S. Appl. No. 14/123,057.
Office Action dated Jan. 13, 2016 in U.S. Appl. No. 13/257,115.
Office Action issued on the corresponding Japanese Patent Application No. P2012-542635 dated Jan. 26, 2016, with English translation.
Office Action dated Mar. 2, 2016 in Canadian Patent Application No. 2,755,790.
Office Action dated Aug. 24, 2016 in U.S. Appl. No. 13/257,115.
Office Action issued on the corresponding Japanese Patent Application No. P2015-546782 dated Nov. 8, 2016, with English translation.
Office Action issued on corresponding Israeli Patent Application No. 220221 dated Nov. 16, 2016, along with an English translation.
Office Action dated Dec. 16, 2016 in U.S. Appl. No. 14/696,028.
Office Action dated Dec. 22, 2016 in Australian Patent Application No. 2016202789.
Office Action dated Mar. 13, 2017 in Chinese Patent Application No. 201280077698.6 (English translation).
Office Action dated Mar. 14, 2017 in European Patent Application No. 12889818.6.
Office Action dated May 19, 2017 in Mexican Patent Application No. MX/a/2016/001812, with English translation.
Office Action dated May 31, 2017 in Canadian Patent Application No. 2,755,790.
Office Action dated Jun. 6, 2017 in Japanese Patent Application No. 2016-105211 (English translation).
Office Action dated Aug. 30, 2017 in Mexican Patent Application No. MX/a/2015/007093, and English translation thereof.
Office Action dated Nov. 1, 2017 in U.S. Appl. No. 14/651,761.
Office Action dated Nov. 12, 2017 in Israeli Patent Application No. 251307 (English translation).
Office Action dated Nov. 20, 2017 in Australian Patent Application No. 2016202789.
Office Action dated Dec. 15, 2017 in Russian Patent Application No. 2015128078 (English translation).
Office Action dated Jan. 16, 2018 in Mexican Patent Application No. MX/a/2016/001812, with English translation.
Office Action dated Jan. 29, 2018 in Indian Patent Application No. 6009/DELNP/2012.
Office Action dated Feb. 13, 2018 in Chinese Patent Application No. 201280077698.6 (English translation).
Office Action dated Mar. 5, 2018 in Mexican Patent Application No. MX/a/2015/007093, and English translation thereof.
Office Action dated Apr. 26, 2018 in Mexican Patent Application No. MX/a/2016/001812, with English translation.
Office Action dated May 15, 2018 in Israeli Patent Application No. 239374 (English translation).
Office Action dated Jul. 2, 2018 in U.S. Appl. No. 14/651,761.
Office Action dated Jul. 4, 2018 in Chinese Patent Application No. 201480020723.6, and English translation thereof (13 pages).

(56) References Cited

OTHER PUBLICATIONS

Office Action dated Jul. 6, 2018 in Canadian Patent Application No. 2,755,790.
Office Action dated Jul. 6, 2018 in European Patent Application No. 14754562.8 (6 pages).
Office Action dated Jul. 23, 2018 in U.S. Appl. No. 15/630,454.
Office Action dated Aug. 20, 2018 in Canadian Patent Application No. 2,894,618 (3 pages).
Office Action dated Aug. 29, 2018 in Chinese Patent Application No. 201280077698.6, and partial English translation thereof (14 pages).
Office Action dated Sep. 5, 2018 in Japanese Patent Application No. P2015-558314, and English translation thereof (8 pages).
Office Action dated Oct. 10, 2018 in Mexican Patent Application No. MX/a/2015/007093, and English translation thereof.
Office Action dated Nov. 23, 2018 in Australian Patent Application No. 2012396787.
Office Action dated Feb. 11, 2019 in Mexican Patent Application No. MX/a/2015/010783, and English translation thereof.
Office Action dated Mar. 12, 2019 in U.S. Appl. No. 15/630,454.
Office Action dated Mar. 21, 2019 in U.S. Appl. No. 14/769,035.
Ohara et al., "One-sided Polymerase Chain Reaction: the Amplification of cDNA," Proceedings of the National Academy of Sciences of the United States of America, vol. 86(15), Aug. 1989, pp. 5673-5677.
Omirulleh et al., "Activity of a Chimeric Promoter With the Doubled CaMV 35S Enhancer Element in Protoplast-Derived Cells and Transgenic Plants in Maize," Plant Molecular Biology, vol. 21(3), Feb. 1993, pp. 415-428.
Ondek et al., "Discrete Elements Within the SV40 Enhancer Region Display Different Cell-Specific Enhancer Activities," The EMBO Journal, vol. 6(4), Apr. 1987, pp. 1017-1025.
Ornitz et al., "Promoter and Enhancer Elements from the Rat Elastase I Gene Function Independently of Each other and of Heterologous Enhancers," Molecular and Cellular Biology, vol. 7(10), Oct. 1987, pp. 3466-3472.
Ozduman et al., "Systemic Vesicular Stomatitis Virus Selectively Destroys Multifocal Glioma and Metastatic Carcinoma in Brain", The Journal of Neuroscience, Feb. 2008, vol. 28(8), pp. 1882-1893.
Palacios et al., "Farmington Virus, Complete Genome", Genbank Accession #HM627182.
Palacios, Gustavo, et al. "Characterization of Farmington virus, a novel virus from birds that is distantly related to members of the family Rhabdoviridae." Virology journal, vol. 10, No. 1 (2013): 219.
McNeall et al., "Hyperinducible Gene Expression From a Metallothionein Promoter Containing Additional Metal-responsive Elements," Gene, vol. 76(1), Mar. 1989, pp. 81-88.
Medina et al., "Development of a Manufacturing Process for an Oncolytic Vaccine", European Society of Gene and cell Therapy French Society of Cell and Gene Therapy, Selected Oral Presentations, A49, OR052, Collaborative Congress Oct. 25-29, 2012.
Melcher et al. "Thunder and Lightning: Immunotherapy and Oncolytic Viruses Collide" Molecular Therapy, vol. 19, No. 6, pp. 1008-1016, Jun. 2001.
Meng, Wilson S., et al. "α-Fetoprotein-specific tumor immunity induced by plasmid prime-adenovirus boost genetic vaccination." Cancer research 61, No. 24 (2001 ): 8782-8786.
Mexican Patent Application No. MX/a/2015/010783, Office Action dated May 28, 2018—English Translation Available.
Miksicek et al., "Glucocorticoid Responsiveness of the Transcriptional Enhancer of Moloney Murine Sarcoma Virus," Cell, vol. 46(2), Jul. 1986, pp. 283-290.
Mineta et al., "Attenuated Multi-Mutated Herpes Simplex Virus-1 for the Treatment of Malignant Gliomas," Nature Medicine, vol. 1(9), Sep. 1995, pp. 938-943.
Mitchell et al., "Active Specific Immunotherapy of Melanoma With Allogeneic Cell Lysates," New York Academy of Sciences, vol. 690(1), 1993, pp. 153-166.

Mitchell et al., "Active-Specific Immunotherapy for Melanoma," Journal of Clinical Oncology, vol. 8(5), May 1990, pp. 856-869.
Mordacq et al., "Co-Localization of Elements Required for Phorbol Ester Stimulation and Glucocorticoid Repression of Proliferin Gene Expression," Genes Development, vol. 3(6), Jun. 1989, pp. 760-769.
Moreau et al., "The SV40 72 Base Repair Repeat Has a Striking Effect on Gene Expression Both in SV40 and Other Chimeric Recombinants," Nucleic Acids Research, vol. 9(22), Nov. 1981, pp. 6047-6088.
Morris, "Epitope Mapping: B-cell Epitopes", Encyclopedia of Life Sciences, 2007, doi: 0.1 002/9780470015902. a0002624.pub2, pp. 1-3.
Morrissey, David, Gerald C. O'Sullivan, and Mark Tangney. "Tumour targeting with systemically administered bacteria." Current gene therapy 10, No. 1 (2010): 3-14.
Morton et al., "Technical Details of Intraoperative Lymphatic Mapping for Early Stage Melanoma," Archives of Surgery, vol. 127(4), Apr. 1992, pp. 392-399.
Mouras et al., "Localization by in Situ Hybridization of a Low Copy Chimaeric Resistance Gene Introduced Into Plants by Direct Gene Transfer," Molecular and General Genetics, vol. 207(2), May 1987, pp. 204-209.
Muesing et al., "Regulation of mRNA Accumulation by a Human Immunodeficiency Virus Trans-Activator Protein," Cell, vol. 48(4), Feb. 1987, pp. 691-701.
Muik et al., "Pseudotyping Vesicular Stomatitis Virus with Lymphocytic Choriomeningitis Virus Glycoproteins Enhances Infectivity for Glioma Cells and Minimizes Neurotropism," Journal of Virology, vol. 85(11 ), Jun. 2011, pp. 5679-5684.
Munger et al., "Mechanisms of Human Papillomavirus-Induced Oncogenesis," Journal of Virology, Nov. 2004, vol. 78(21), pp. 11451-11460.
Nakaya et al., "Recombinant Newcastle Disease Virus as a Vaccine Vector," Journal of Virology, vol. 75(23), Dec. 2001, pp. 11868-11873.
Narisawa-Saito et al., "Basic Mechanisms of High-Risk Human Papillomavirus-Induced Carcinogenesis: Roles of E6 and E7 Proteins," Cancer Science, Oct. 2007, vol. 98(10), pp. 1505-1511.
Needleman et al., "A general method applicable to the search for similarities in the amino acid sequence of two proteins", J. Mol. Biol. vol. 48, pp. 443-453, 1970.
Nicholaou et al., "Directions in the Immune Targeting of Cancer: Lessons Learned From the Cancer-testis Ag NYS0- ESO-1," Immunology and Cell Biology, vol. 84(4), Jun. 2006, pp. 303-317.
Nicolau et al., "Liposome-Medialed DNA Transfer in Eukaryotic Cells, Dependence of the transfer Efficiency Upon the Type of Liposomes Used and the Host Cell Cycle Stage," Biochimica Et Biophysica Acta, vol. 721 (2), Oct. 1982, pp. 185-190.
Nicolau et al., "Liposomes as Carriers for in Vivo Gene Transfer and Expression," Methods in Enzymology, vol. 149, 1987, pp. 157-176.
Ng et al., "Development of a FLP/frt System for Generating Helper-Dependent Adenoviral Vectors," Molecular Therapy, vol. 3(5), May 2001, pp. 809-815.
Ng et al., "Regulation of the Human Beta-Actin Promoter by Upstream and Intron Domains," Nucleic Acids Research, vol. 17(2), Jan. 1989, pp. 601-615.
Nomoto et al., "Cloning and Characterization of the Alternative Promoter Regions of the Human LIMK2 Gene Responsible for Alternative Transcripts With Tissue-Specific Expression," Gene, vol. 236(2), Aug. 1999, pp. 259-271.
Non-Final Office Action No. 1 issued on the corresponding U.S. Appl. No. 14/696,028, dated Dec. 16, 2016.
Notice of Acceptance dated Jan. 30, 2016, issued on the Australian Patent Application No. 2010329551.
Notice of Allowance dated Feb. 16, 2016 in U.S. Appl. No. 14/123,057.
Notice of Allowance dated Feb. 2, 2015 in U.S. Appl. No. 13/514,837.
Notice of Allowance dated Mar. 17, 2017 in U.S. Appl. No. 13/257,115.
Notice of Allowance dated Oct. 6, 2017 in U.S. Appl. No. 14/696,028.

(56) References Cited

OTHER PUBLICATIONS

Notice of Reasons for Rejection issued on corresponding Japanese Patent Application No. 2012-542635 dated Mar. 3, 2015, with an English translation.
Office Action dated Dec. 19, 2014 in U.S. Appl. No. 14/123,057.
Office Action dated May 5, 2016, issued on the Canadian Patent Application No. 2,836,117.
Office Action dated Oct. 26, 2012 in U.S. Appl. No. 13/257, 115.
Office Action issued against corresponding Chinese Application No. 201080063490.X dated May 13, 2013, along with an English translation.
Office Action dated Mar. 15, 2013 in U.S. Appl. No. 13/257,115.
Office Action dated Apr. 11, 2013 in Chinese Patent Application No. 201080022270.2 (English translation).
Office Action dated Oct. 9, 2013 in U.S. Appl. No. 13/257,115.
Office Action issued against corresponding Chinese Application No. 201080063490.X dated Dec. 23, 2013, along with an English translation.
Office Action dated Jan. 6, 2014 in Chinese Patent Application No. 201080022270.2 (English translation).
Office Action dated Jan. 14, 2014 in U.S. Appl. No. 13/514,837.
Office Action dated Jun. 6, 2014 in European Patent Application No. 10753031.3.
Office Action dated Jul. 16, 2014 in U.S. Appl. No. 13/257,115.
Office Action issued on corresponding U.S. Appl. No. 13/514,837 dated Aug. 1, 2014.
Office Action dated Oct. 10, 2014 in Chinese Patent Application No. 201080022270.2 (English translation).
Office Action dated Nov. 20, 2014 in U.S. Appl. No. 13/257,115.
Office Action issued on corresponding Israeli Patent Application No. 220221 dated Feb. 25, 2015, along with an English translation.
Celander et al., "Regulatory Elements with in the Murine Leukemia Virus Enhancer Regions Mediate Clucocorticoid Responsiveness," Journal of Virology, vol. 62(4), Apr. 1988, pp. 1314-1322.
Chandler et al., "RNA Splicing Specificity Determined by the Coordinated Action of RNA Recognition Motifs in SR Proteins," Proceedings of the National Academy of Sciences of the United States of America, vol. 94(8), Apr. 1997, pp. 3596-3601.
Chang et al., "Glucose-Regulated Protein {GRP94 and GRP78) Genes Share Common Regulatory Domains and are Coordinately Regulated by Common Trans-Acting Factors," Molecular and Cellular Biology, vol. 9(5), May 1989, pp. 2153-2162.
Chatterjee et al., "Negative Regulation of the Thyroid-Stimulating Hormone Alpha Gene by Thyroid Hormone: Receptor Interaction Adjacent to the Tata Box," Proceedings of the National Academy of Sciences of the United States of America, vol. 86(23), Dec. 1989, pp. 9114-9118.
Chen et al., "High-efficiency Transformation of Mammalian Cells by Plasmid DNA," Molecular and Cellular Biology, vol. 7(8), Aug. 1987, pp. 2745-2752.
Chen et al., "Oncology Meets Immunology: The Cancer-Immunity Cycle," Immunity, Jul. 2013, vol. 39(1), pp. 1-10.
Chiocca, "The Host Response to Cancer Virotherapy," Current Opinion in Molecular Therapeutics, vol. 10(1 ), Feb. 2008, pp. 38-45.
Cho et al., "BiVax: A Peptide/Poly-IC Subunit Vaccine that Mimics an Acute Infection Elicits Vast and Effective Anti-Tumor CD8 T-Cell Responses," Cancer Immunology, Immunotherapy, Apr. 2013, vol. 62(4), pp. 787-799.
Choi et al., "An Altered Pattern of Cross-Resistance in Multidrug-Resistant Human Cells Results From Spontaneous Mutations in the mdr1 (P-Glycoprotein) Gene," Cell, vol. 53(4), May 1988, pp. 519-529.
Christodoulides et al., "Immunization With Recombinant Class I Outermembrane Protein From Neisseria Meningitidis: Influence of Liposomes and Adjuvants on Antibody Avidity, Recognition of Native Protein and the Induction of a Bactericidal Immune Response Against Meningococci," Microbiology, vol. 144(11), Nov. 1998, pp. 3027-3037.
Chuang, Chi-Mu, et al. "Combination of viral oncolysis and tumor-specific immunity to control established tumors." Clinical Cancer Research, vol. 15, No. 14 (2009): 4581-4588.
Cleary et al., "Detection of a Second T(14;18) Breakpoint Cluster Region in Human Follicular Lymphomas," The Journal of Experimental Medicine, vol. 164(1), Jul. 1986, pp. 315-320.
Cleary et al., "Nucleotide Sequence of a T(14;18) Chromosomal Breakpoint in Follicular Lymphoma and Demonstration of a Breakpoint-cluster Region Near a Transcriptionally Active Locus of Chromosome 18," Proceedings of the National Academy of Sciences of the United States of America, vol. 82(21), Nov. 1985, pp. 7439-7443.
Cocea, "Duplication of a Region in the Multiple Cloning Site of a Plasmid Vector to Enhance Cloning-mediated Addition of Restriction Sites to a DNA Fragment," Biotechniques, vol. 23(5), Nov. 1997, pp. 814-816.
Coffey et al., "Reovirus Therapy of Tumors With Activated Ras Pathway," Science, vol. 282 (5392), Nov. 1998, pp. 1332-1334.
Cohen et al., "Serotonin Receptor Activation of Phosphoinositide Turnover in Uterine, Fundal, Vascular, and Tracheal Smooth Muscle," Journal of Cardiovascular Pharmacology, vol. 10(2), Aug. 1987, pp. 176-181.
Connor et al., "Role of Residues 121 to 124 Vesicular Stomatitis Virus Matrix Protein in Virus Assembly and Virus-Host Interaction," Journal of Virology, vol. 80(8), Apr. 2006, pp. 3701-3711.
Costa et al., "The Cell-specific Enhancer of the Mouse Transthyretin (Prealbumin) Gene Binds a Common Factor at One Site and a Liver-specific Factor(s) at Two other Sites," Molecular and Cellular Biology, vol. 8(1), Jan. 1988, pp. 81-90.
Cripe et al., "Transcriptional Regulation of the Human Papillomavirus-16 E6-E7 Promoter by a Keratinocyte-dependent Enhancer, and by Viral E2 Trans-activator and Repressor Gene Products: Implications for Cervical Carcinogenesis," The EMBO Journal, vol. 6(12), Dec. 1987, pp. 3745-3753.
Culotta et al., "Fine Mapping of a Mouse Metallothionein Gene Metal Response Element," Molecular and Cellular Biology, vol. 9(3), Mar. 1989, pp. 1376-1380.
Culver et al., "In Vivo Gene Transfer With Retroviral Vector-producer Cells for Treatment of Experimental Brain Tumors," Science, vol. 256(5063), Jun. 1992, pp. 1550-1552.
Cunningham et al., "High-resolution Epitope Mapping of hGH-Receptor Interactions by Alanine-scanning Mutagenesis," Science, vol. 244(4908), Jun. 1989, pp. 1081-1085.
Cybinski et al., "Isolation of Tibrogargan Virus, a New Australian Rhabdovirus, From Culicoides Brevitarsis," Veterinary Microbiology, vol. 5, Jun. 1980, pp. 301-308.
Dandolo et al., "Regulation of Polyoma Virus Transcription in Murine Embryonal Carcinoma Cells," Journal of Virology, vol. 47(1), Jul. 1983, pp. 55-64.
Davidson et al., "Intralesional Cytokine Therapy in Cancer: a Pilot Study of GM-CSF Infusion in Mesothelioma," Journal of Immunotherapy, vol. 21(5), Sep. 1998, pp. 389-398.
De Mare, A., et al. "Viral vector-based prime-boost immunization regimens: a possible involvement of T-cell competition." Gene therapy, vol. 15, No. 6 (2008): 393.
De Martel et al., "Global Burden of Cancers Attributable to Infections in 2008: A Review and Synthetic Analysis," The Lancet Oncology, Jun. 2012, vol. 13(6), pp. 607-615.
De Plaen et al., "Structure, Chromosomal Localization, and Expression of 12 Genes of the Mage Family," Immunogenetics, vol. 40(5), Sep. 1994, pp. 360-369.
De Villiers et al., "Polyoma Virus DNA Replication Requires an Enhancer," Nature, vol. 312 (5991), Nov. 1984, pp. 242-246.
Decision to Grant issued on the corresponding European patent application No. 10835567 .8 dated Sep. 8, 2016.
Deschamps et al., "Identification of a Transcriptional Enhancer Element Upstream From the Proto-Oncogene Fos," Science, vol. 230(4730), Dec. 1985, pp. 1174-1177.
Dhar et al., "Effect of Preexisting Immunity on Oncolytic Adenovirus Vector INGN 007 Antitumor Efficacy in Immunocompetent and Immunosuppressed Syrian Hamsters," Journal of Virology, vol. 83(5), Mar. 2009, pp. 2130-2139.

(56) References Cited

OTHER PUBLICATIONS

Diallo et al., "Propagation, Purification, and in Vivo Testing of Oncolytic Vesicular Stomatitis Virus Strains," Methods in Molecular Biology, vol. 797, Jan. 2012, pp. 127-140.
Diaz, Rosa Maria, et al. "Oncolytic immunovirotherapy for melanoma using vesicular stomatitis virus." Cancer research 67, No. 6 (2007): 2840-2848.
Dilman, "Perceptions of Herceptin: A Monoclonal Antibody for the Treatment of Breast Cancer," Cancer Biotherapy & Radiopharmaceuticals, vol. 14(1), Feb. 1999, pp. 5-10.
Doherty et al., "Isolation of Arboviruses From Mosquitoes, Biting Midges, Sandflies and Vertebrates Collected in Queensland, 1969 and 1970," Transactions of the Royal Society of Tropical Medicine and Hygiene, vol. 67(4), Feb. 1973, pp. 536-543.
Dudani et al., "Multiple Mechanisms Compensate to Enhance Tumor-Protective CD8(+) T Cell Response in the Long Term Despite Poor CD8(+) T Cell Priming Initially: Comparison Between an Acute Versus a Chronic Intracellular Bacterium Expressing a Model Antigen," The Journal of Immunology, Jun. 2002, vol. 168(11), pp. 5737-5745.
Ebert, Oliver, et al. "Systemic therapy of experimental breast cancer metastases by mutant vesicular stomatitis virus in immune-competent mice." Cancer gene therapy 12, No. 4 (2005): 350.
Edbrooke et al., "Identification of cis-acting Sequences Responsible for Phorbol Ester Induction of Human Serum Amyloid a Gene Expression via a Nuclear Factor kB-like Transcription Factor," Molecular and Cellular Biology, vol. 9 (5), May 1989, pp. 1908-1916.
Edlund et al., "Cell-specific Expression of the Rat Insulin Gene: Evidence for Role of Two Distinct 5' Flanking Elements," Science, vol. 230(4728), Nov. 1985, pp. 912-916.
Endo et al., "Virus-Mediated Oncolysis Induces Danger Signal and Stimulates Cytotoxic T-lymphocyte Activity via Proteasome Activator Upregulation," Oncogene, vol. 27(17), Apr. 2008, pp. 2375-2381.
Examination Report No. 1 issued against corresponding Australian Patent Application No. 2010329551, dated May 15, 2014.
Examination Report No. 1 issued on the corresponding Australian patent application No. 2016202789, dated Dec. 22, 2016.
Extended European Search Report dated Jan. 11, 2013 in European Patent Application No. 10753031.3.
Extended European Search Report dated Nov. 21, 2014 in European Patent Application No. 12796050.8.
Extended European Search Report for Application No. EP12889818, dated Apr. 15, 2016, 8 Pages.
European Patent Application No. 14754562.8, Office Action dated Jul. 21, 2017.
European Search Report issued on corresponding European Application No. 10835567.8 dated Aug. 19, 2013.
Fechheimer et al., "Transfection of Mammalian Cells With Plasmid DNA by Scrape Loading and Sonication Loading," Proceedings of the National Academy of Sciences of the United States of America, vol. 84(23), Dec. 1987, pp. 8463-8467.
Feng et al., "Hiv-1 Tat Trans-activation Requires the Loop Sequence Within Tar," Nature, vol. 334(6178), Jul. 1988, pp. 165-167.
Kiledjian et al., "Identification and Characterization of Two Functional Domains within the Murine Heavy-Chain Enhancer," Molecular and Cellular Biology, vol. 8(1), Jan. 1988, pp. 145-152.
Kinoh et al., "Generation of a Recombinant Sendai Virus That is Selectively Activated and Lyses Human Tumor Cells Expressing Matrix Metalloproteinases," Gene Therapy, vol. 11(4), Jul. 2004, pp. 1137-1145.
Kirn, David H., et al. "Targeted and armed oncolytic poxviruses: a novel multi-mechanistic therapeutic class for cancer." Nature Reviews Cancer 9, No. 1 (2009): 64.
Klamut et al., "Molecular and Functional Analysis of the Muscle-Specific Promoter Region of the Duchenne Muscular Dystrophy Gene," Molecular and Cellular Biology, vol. 10(1), Jan. 1990, pp. 193-205.

Klebanoff et al., "CD8+ T-Cell Memory in Tumor Immunology and Immunotherapy," Immunological Reviews, Jun. 2006, vol. 211(1), pp. 214-224.
Koch et al., "Anatomy of a New B-Cell-Specific Enhancer," Molecular and Cellular Biology, vol. 9(1), Jan. 1989, pp. 303-311.
Kraus et al., "Alternative Promoter Usage and Tissue Specific Expression of the Mouse Somatostatin Receptor 2 Gene," FEBS Letters, vol. 428(3), May 1998, pp. 165-170.
Kriegler et al., "Enhanced Transformation by a Simian Virus 40 Recombinant Virus Containing a Harvey Murine Sarcoma Virus Long Terminal Repeat," Molecular and Cellular Biology, vol. 3(3), Mar. 1983, pp. 325-339.
Kriegler et al., "Transformation Mediated by the SV40 T Antigens: Separation of the Overlapping SV40 Early Genes with a Retroviral Vector," Cell, vol. 38(2), Sep. 1984, pp. 483-491.
Kriegler et al., "A Novel Form of TNF/Cachectin is a Cell Surface Cytotoxic Transmembrane Protein: Ramifications or the Complex Physiology of TNF," Cell, vol. 53(1), Apr. 1988, pp. 45-53.
Kruisbeek et al., "Mechanisms Underlying T-Cell Tolerance," Current Opinion in Immunology, vol. 8(2), Apr. 1996, pp. 233-44.
Kuhl et al., "Reversible Silencing of Enhancers by Sequences Derived From the Human IFN-Alpha Promoter," Cell, vol. 50(7), Sep. 1987, pp. 1057-1069.
Kunz et al., "Identifications of the Promoter Sequences Involved in the Inlerleukin-6 Dependent Expression of the Rat Alpha2-macroglobulin Gene," Nucleic Acids Research, vol. 17(3), Feb. 1989, pp. 1121-1138.
Kwoh et al., "Transcription-based Amplification System and Detection of Amplified Human Immunodeficiency Virus Type 1 With a Bead-based Sandwich Hybridization Formal," Proceedings of the National Academy of Sciences of the United States of America, vol. 86(4), Feb. 1989, pp. 1173-1177.
Kyte et al., "A Simple Method for Displaying the Hydropathic Character of a Protein," Journal Molecular Biology, vol. 157(1), May 1982, pp. 105-132.
Lai et al., "Using G-Deleted Vesicular Stomatitis Virus to Probe the Innate Anti-Viral Response," Journal of Virological Methods, Nov. 2008, vol. 153(2), pp. 276-279.
Lane et al., Vaccination-Induced Autoimmune Vitiligo Is a Consequence of Secondary Trauma to the Skin, Cancer Research, vol. 64(4), Feb. 2004, pp. 1509-1515.
Lareyre et al., "A 5-Kilbase pair Promoter Fragment of the Murine Epididymal Relinoic Acid-binding Protein Gene Drives the Tissue-specific, Cell-specific, and Androgen-regulated Expression of a Foreign Gene in the Epididymis of Transgenic Mice," The Journal of Biological Chemistry, vol. 274(12), Mar. 1999, pp. 8282-8290.
Larsen et al., "Repression Mediates Cell-type-specific Expression of the Rat Growth Hormone Gene," Proceedings of the National Academy of Sciences of the United States of America, vol. 83(21), Nov. 1986, pp. 8283-8287.
Laspia et al., "HIV-1 Tat Protein Increases Transcriptional Initiation and Stabilizes Elongation.," Cell, vol. 59(2), Oct. 1989, pp. 283-292.
Latimer et al., "Highly Conserved Upstream Regions of the alphal-Antitrypsin Gene in Two Mouse Species Govern Liver-Specific Expression by Different Mechanisms," Molecular and Cellular Biology, vol. 10(2), Feb. 1990, pp. 760-769.
Lawson et al., "Recombinant Vesicular Stomatitis Viruses From DNA," Proceedings of the National Academy of Sciences of the United States of America, vol. 92(10), May 1995, pp. 4477-4481.
Le Boeuf et al., "Sensitivity of cervical carcinoma cells to vesicular stomatitis virus-induced oncolysis: potential role of human papilloma virus infection," International Journal of Cancer, Jan. 2012, vol. 131(3), pp. E204-E215.
Le Boeuf, Fabrice, et al. "Model-based rational design of an oncolytic virus with improved therapeutic potential." Nature communications vol. 4, p. 1974, Jun. 2013.
Le Boeuf, Fabrice, et al. "Synergistic interaction between oncolytic viruses augments tumor killing." Molecular Therapy vol. 18, No. 5, pp. 888-895, May 2010.
Lee et al., "Functional Analysis of the Steroid Hormone Control Region of Mouse Mammary Tumour Virus," Nucleic Acids Research, vol. 12(10), May 1984, pp. 4191-4206.

(56) References Cited

OTHER PUBLICATIONS

Lee et al., "Glucocorticoids Regulate Expression of Dihydrofolate Reductase cDNA in Mouse Mammary Tumour Virus Chimaeric Plasmids," Nature, vol. 294(5838), Nov. 1981, pp. 228-232.

Lee et al., "The Highly Basic Ribosomal Protein L41 Interacts with the beta Subunit of Protein Kinase CKII and Stimulates Phosphorylation of DNA Topoisomerase IIalpha by CKII," Biochemical and Biophysical Research Communications, vol. 238(2), Sep. 1997, pp. 462-467.

Levenson et al., "Internal Ribosomal Entry Site-Containing Retroviral Vectors with Green Fluorescent Protein and Drug Resistance Markers," Human Gene Therapy, vol. 9(8), May 1998, pp. 1233-1236.

Levinson et al., "Activation of SV40 Genome by 72-base Pair Tandem Repeats of Moloney Sarcoma Virus.," Nature,vol. 295(5850), Feb. 1982, pp. 568-572.

Levitskaya et al., "Inhibition of Antigen Processing by the Internal Repeat Region of the Epstein-barr Virus Nuclear Antigen-1.," Nature, vol. 375(6533), Jun. 1995, pp. 685-688.

Lewis et al., "Inlerleukin-1 and Cancer Progression: The Emerging Role of Inlerleukin-1 Receptor Antagonist as a Novel Therapeutic Agent in Cancer Treatment," Journal of Translational Medicine, Nov. 2006, vol. 4(1), pp. 18-59.

Li, Qi-Xiang, et al. "Oncolytic virotherapy as a personalized cancer vaccine." International journal of cancer 123, No. 3 (2008): 493-499.

Liao, John B., et al. "Single-dose, therapeutic vaccination of mice with vesicular stomatitis virus expressing human papillomavirus type 16 E7 protein." Clin. Vaccine lmmunol. 15, No. 5 (2008): 817-824.

Lichty, Brian D., Anthony T. Power, David F. Stojdl, and John C. Bell. "Vesicular stomatitis virus: re-inventing the bullet." Trends in molecular medicine 10, No. 5 (2004): 210-216.

Lin et al., "Chromosome Localization of Two Human Serine Protease Genes to Region 14q11.2-q12 by in Situ Hybridization.," Cytogenetics and Cell Genetics, vol. 53(2-3), Feb. 1990, pp. 169-171.

Liu, Ta-Chiang, et al. "The targeted oncolytic poxvirus JX-594 demonstrates antitumoral, antivascular, and anti-HBV activities in patients with hepatocellular carcinoma." Molecular Therapy, vol. 16, No. 9, pp. 1637-1642, Sep. 2008.

Liu, Y., et al. "Adenovirus-mediated intratumoral expression of immunostimulatory proteins in combination with systemic Treg inactivation induces tumor-destructive immune responses in mouse models." Cancer Gene Therapy, vol. 18, No. 6, pp. 407-418, Jun. 2011.

Logg et al., "A Uniquely Stable Replication-Competent Retrovirus Vector Achieves Efficient Gene Delivery in Vitro and in Solid Tumors," Human Gene Therapy, vol. 12(8), May 2001, pp. 921-932.

Lowy et al., "Reducing HPV-Associated Cancer Globally," Cancer Prevention Research, Jan. 2012, vol. 5(1), pp. 18-23.

Lun et al., "Effects of Intravenously Administered Recombinant Vesicular Stomatitis Virus (VSV -M51) on Multifocal and Invasive Gliomas," Journal of the National Cancer Institute, vol. 98(21), 2006, pp. 1546-1547.

Luria et al., "Promoter and Enhancer Elements in the Rearranged Alpha Chain Gene of the Human T Cell Receptor," The EMBO Journal, vol. 6(11), Nov. 1987, pp. 3307-3312.

Lusky et al., "Bovine Papilloma Virus Contains an Activator of Gene Expression at the Distal End of the Early Transcription Unit.," Molecular and Cellular Biology, vol. 3(6), Jun. 1983, pp. 1108-1122.

Lusky et al., "Transient Replication of Bovine Papilloma Virus Type 1 Plasmids: Cis and Trans Requirements," Proceedings of the National Academy of Sciences of the United States of America, vol. 83(11), Jun. 1986, pp. 3609-3613.

Macejak et al., "Internal Initiation of Translation Mediated by the 5' Leader of a Cellular mRNA," Nature, vol. 353 (6339), Sep. 1991, pp. 90-94.

Mahoney et al., Virus-tumor Interactome Screen Reveals Er Stress Response Can Reprogram Resistant Cancers or Ocolytic Virus-triggered Caspase-2 Cell Death, Cancer Cell, vol. 20(4), Oct. 2011, pp. 443-456.

Mahoney et al., "Molecular Pathways: Multimodal Cancer-Killing Mechanisms Employed by Oncolytic Vesiculoviruses," Clinical Cancer Research, Feb. 2013, vol. 19(4), pp. 758-763.

Majid, Ayaz M., et al. "Recombinant vesicular stomatitis virus (VSV) and other strategies in HCV vaccine designs and immunotherapy." Hepatitis C Viruses: Genomes and Molecular Biology (2006): 423-450.

Majors et al., "A Small Region of the Mouse Mammary Tumor Virus Long Terminal Repeat Confers Glucocorticoid Hormone Regulation on a Linked Heterologous Gene," Proceedings of the National Academy of Sciences of the United States of America, vol. 80(19), Oct. 1983, pp. 5866-5870.

Marshall, John L., et al. "Phase I study in advanced cancer patients of a diversified prime-and-boost vaccination protocol using recombinant vaccinia virus and recombinant nonreplicating avipox virus to elicit anti-carcinoembryonic antigen immune responses." Journal of Clinical Oncology 18, No. 23 (2000): 3964-3973.

Satake et al., "Biological Activities of Oligonucleotides Spanning the F9 Point Mutation within the Enhancer Region of Dolyomavirus DNA," Journal of Virology, vol. 62(3), Mar. 1988, pp. 970-977.

Sawyer et al., "Carboxyl-Carboxylate Interactions in Proteins," Nature, vol. 295(5844), Jan. 1982, pp. 79-80.

Schaffner et al., "Redundancy of Information in Enhancers as a Principle of Mammalian Transcription Control," Journal of Molecular Biology, vol. 201(1), May 1988, pp. 81-90.

Schnell et al., "Infectious Rabies Viruses From Cloned cDNA," The EMBO Journal, vol. 13(18), Sep. 1994, pp. 4195-4203.

Searle et al., "Building a Metal-Responsive Promoter with Synthetic Regulatory Elements," Molecular and Cellular Biology, vol. 5(6), Jun. 1985, pp. 1480-1489.

Second Office Action issued against corresponding Mexican Patent Application No. MX/a/2012/006508 dated Jul. 28, J015.

Seder et al., "T-Cell Quality in Memory and Protection: Implications for Vaccine Design," Nature Reviews Immunology, Apr. 2008, vol. 8(4), pp. 247-258.

Shafren et al., "Systemic Therapy of Malignant Human Melanoma Tumors by a Common Cold-Producing Enterovirus, Coxsackievirus A21," Clinical Cancer Research, vol. 10(1 Pt 1 ), Jan. 2004, pp. 53-60.

Sharp et al., "HIV TAR: An RNA Enhancer," Cell, vol. 59(2), Oct. 1989, pp. 229-230.

Shaul et al., "Multiple Nuclear Proteins in Liver Cells Are Bound to Hepatitis B Virus Enhancer Element and Its Upstream Sequences," The EMBO Journal, vol. 6(7), Jul. 1987, pp. 1913-1920.

Sherman et al., "Class II Box Consensus Sequences in the HLA-DR Alpha Gene: Transcriptional Function and Interaction with Nuclear Proteins," Molecular and Cellular Biology, vol. 9(1), Jan. 1989, pp. 50-56.

Shizaki et al., "Heterologous Prime/Boost Immunization with p53-Based Vaccines Combined with Toll-Like Receptor Stimulation Enhances Tumor Regression," Journal of Immunotherapy, Jul. 2010, vol. 33(6), pp. 609-617.

Silva et al., "PLAC1, A Trophoblast-specific Cell Surface Protein, Is Expressed in a Range of Human Tumors and Elicits Spontaneous Antibody Responses," Cancer Immunity, vol. 7, Nov. 2007, pp. 18.

Sleigh et al., "SV40 Enhancer Activation During Retinoic Acid-induced Differentiation of F9 Embryonal Carcinoma Cells," The EMBO Journal, vol. 4(13B), Dec. 1985, pp. 3831-3837.

Spalholz et al., "Transactivation of a Bovine Papilloma Virus Transcriptional Regulatory Element by the E2 Gene Product," Cell, vol. 42(1), Aug. 1985, pp. 183-191.

Spandau et al., "Trans-Activation of Viral Enhancers by the Hepatitis B Virus X Protein," Journal of Virology, vol. 62 (2), Feb. 1988, pp. 427-434.

Spandidos et al., "Host-Specificities of Papillomavirus, Moloney Murine Sarcoma Virus and Simian Virus 40 Enhancer Sequences," The EMBO Journal, vol. 2 (7), 1983, pp. 1193-1199.

(56) References Cited

OTHER PUBLICATIONS

Stemmer et al., "DNA Shuffling by Random Fragmentation and Reassembly: In Vitro Recombination for Molecular Evolution," Proceedings of the National Academy of Science USA, vol. 91(22), Oct. 1994, pp. 10747-10751.
Stephens et al., "The Bovine Papillomavirus Genome and Its Uses as a Eukaryotic Vector," The Biochemical Journal, vol. 248(1), Nov. 1987, pp. 1-11.
Stillman et al., "Replication and Amplification of Novel Vesicular Stomatitis Virus Minigenomes Encoding Viral Structural Proteins," Journal of Virology, vol. 69(5), May 1995, pp.
Stockinger, "T Lymphocyte Tolerance: From Thymic Deletion to Peripheral Control Mechanisms," Advances in Immunology, vol. 71, 1999, pp. 229-265.
Stojdl et al., "Exploiting Tumor-specific Defects in the Interferon Pathway With a Previously Unknown Oncolytic Virus," Nature Medicine, vol. 6(7), Jul. 2000, pp. 821-825.
Stojdl et al., VSV Strains With Defects in Their Ability to Shutdown Innate Immunity Are Potent Systemic Anti Cancer Agents, Cancer Cell, vol. 4(4), Oct. 2003, pp. 263-275.
Stuart et al., "Identification of Multiple Metal Regulatory Elements in Mouse Metallothionein-i Promoter by Assaying Synthetic Sequences," Nature, vol. 317(6040), Oct. 1985, pp. 828-831.
Stylli, Stanley S., et al. "Mouse models of glioma." Journal of Clinical Neuroscience vol. 22, No. 4, pp. 619-626, Apr. 2015.
Sullivan et al., "Transcriptional Enhancers in the HLA-DQ Subregion," Molecular and Cellular Biology, vol. 7(9), Sep. 1987, pp. 3315-3319.
Supplementary European Search Report for Application No. EP14754562.8, dated Oct. 24 2016, 11 pages.
Sur et al., "Vesicular Stomatitis Virus Infection and Neuropathogenesis in the Murine Model are Associated with Apoptosis," Veterinary Pathology, vol. 40(5), Sep. 2003, pp. 512-520.
Swartzendruber et al., "Neoplastic Differentiation: Interaction of Simian Virus 40 and Polyoma Virus with Murine Teratocarcinoma Cells in Vitro," Journal of Cellular Physiology, vol. 85(2 Pt 1), Apr. 1975, pp. 179-188.
Takada et al., "A System for Functional Analysis of Ebola Virus Glycoprotein," Proceedings of the National Academy of Science USA, vol. 94(26), Dec. 1997, pp. 14764-14769.
Takebe et al., "Sr alpha Promoter: An Efficient and Versatile Mammalian eDNA Expression System Composed of the Simian Virus 40 Early Promoter and the R-U5 Segment of Human T-Cell Leukemia Virus Type 1 Long Terminal Repeat," Molecular and Cellular Biology, vol. 8(1), Jan. 1988, pp. 466-472.
Tangney et al., "Listeria Monocytogenes as a Vector for Anti-cancer Therapies," Current Gene Therapy, Feb. 2010, vol. 10(1), pp. 46-55.
Tavernier et al., "Deletion Mapping of the Inducible Promoter of Human IFN-beta Gene," Nature, vol. 301(5901 ), Feb. 1983, pp. 634-636.
Taylor et al., "E1a Transactivation of Human HSP70 Gene Promoter Substitution Mutants is Independent of the Composition of Upstream and TATA Elements," Molecular and Cellular Biology, vol. 10(1), Jan. 1990, pp. 176-183.
Taylor et al., "Factor Substitution in a Human HSP70 Gene Promoter: TATA-dependent and TATA-independent Interactions," Molecular and cellular biology, vol. 10(1), Jan. 1990, pp. 165-175.
Taylor et al., "Stimulation of the Human Heat Shock Protein 70 Promoter in Vitro by Simian Virus 40 Large T Antigen," The Journal of biological chemistry, vol. 264(27), Sep. 1989, pp. 16160-16164.
Terstegen et al., "The Vesicular Stomatitis Virus Matrix Protein Inhibits Glycoprotein 130-Dependent STAT Activation.," Journal of Immunology, vol. 167(9), Nov. 2001, pp. 5209-5216.
Tesh, Robert B., et al. "Efficacy of killed virus vaccine, live attenuated chimeric virus vaccine, and passive immunization for prevention of West Nile virus encephalitis in hamster model." Emerging infectious diseases 8, No. 12 (2002): 1392.
Tesh, Robert B., et al. "Immunization with heterologous flaviviruses protective against fatal West Nile encephalitis." Emerging infectious diseases 8, No. 3 (2002): 245.

Thiesen et al., "A DNA Element Responsible for the Different Tissue Specificities of Friend and Moloney Retroviral Enhancers.," Journal of Virology, vol. 62(2), Feb. 1988, pp. 614-618.
Third Office Action issued on corresponding Chinese Patent Application No. 201080063490.X dated Aug. 13, 2014, with English translation of text.
Thomas et al., "The Role of the E6-p53 Interaction in the Molecular Pathogenesis of HPV," Oncogene, Dec. 1999, vol. 18(53), pp. 7690-7700.
Thompson et al., "CLUSTAL W: Improving the Sensitivity of Progressive Multiple Sequence Alignment Through Sequence Weighting, Position-Specific Gap Penalties and Weight Matrix Choice," Nucleic Acids Research, vol. 22 (22), Nov. 1994, pp. 4673-4680.
Toussaint et al., "Live-Attenuated Bacteria as a Cancer Vaccine Vector," Expert Review Vaccines, Oct. 2013, vol. 12(10), pp. 1139-1154.
Travassos Da Rosa et al., "Carajas and Maraba Viruses, Two New Vesiculoviruses Isolated from Phlebotomine Sand Flies in Brazil," The American Journal of Tropical Medicine and Hygiene, vol. 33(5), Sep. 1984, pp. 999-1006.
Travassos Da Rosa et al., "Two New Rhabdoviruses (Rhabdoviridae) Isolated from Birds During Surveillance for Arboviral Encephalitis, Northeastern United States," Emerging Infectious Diseases, vol. 8(6), Jun. 2002, pp. 614-618.
Treisman, "Identification of a Protein-Binding Site That Mediates Transcriptional Response of the C-fos Gene to Serum Factors," Cell, vol. 46(4), Aug. 1986, pp. 567-574.
Tronche et al., "Anatomy of the Rat Albumin Promoter," Molecular biology & medicine, vol. 7(2), Apr. 1990, pp. 173-185.
Tronche et al., "The Rat Albumin Promoter: Cooperation with Upstream Elements Is Required when Binding of APF HNF1 to the Proximal Element Is Partially Impaired by Mutation or Bacterial Methylation," Molecular and Cellular Biology, vol. 9(11), Nov. 1989, pp. 4759-4766.
Trudel et al., "A 3' Enhancer Contributes to the Stage-Specific Expression of the Human Beta-Globin Gene," Genes and Development, vol. 1(9), Sep. 1987, pp. 954-961.
Decision to Grant dated Jan. 21, 2019 in Russian Application No. 2015135890.
Intention to Grant dated Feb. 12, 2019 in European Application No. 14754562.8 (including text intended for grant).
Certificate of Patent dated Apr. 4, 2019 for Russian Patent No. 2,684,211 with translation of bibliographic data in English.
Decision to Grant dated May 3, 2019 in European Application No. 14754562.8.
Pre-examination Office Action dated May 9, 2019 in Brazilian Application No. BR112012013664-0 with machine translation.
Second Office Action dated May 24, 2019 in Chinese Patent Application No. 201480020723.6.
Notice of Allowance dated May 24, 2019 in U.S. Appl. No. 14/769,035.
Corrected Notice of Allowance dated Jun. 12, 2019 in in U.S. Appl. No. 14/769,035.
Office Action dated Jun. 19, 2019 in Israeli Application No. 240723.
Issue Notification dated Jul. 10, 2019 in U.S. Appl. No. 14/769,035.
Office Action dated Aug. 12, 2019 in Canadian Application No. 2,755,790.
Notice of Acceptance dated Jan. 23, 2019 in Australian Patent Application No. 2014221143.
Notice of Grant dated May 23, 2019 for Australian Australian Patent No. 2014221143.
Certificate of Grant dated May 23, 2019 for Australian Australian Patent No. 2014221143.
Chen, et al. "The Development of Cancer Biotherapy", Journal of Practical Oncology, vol. 27, No. 5, Dec. 2012, pp. 547-551.
Tan, "Oncolytic Adenoviruses for Targeted Cancer Therapy: From the Laboratory to the Clinic", Chinese Journal of Cancer Biotherapy, vol. 19, No. 6, Dec. 2012, pp. 569-576.
Hongming, Li, et al. "Research development on treating tumor by oncolytic virus" Medicine World, No. 9, pp. 121-122, Sep. 30, 2006, and English translation thereof.
Office Action dated Mar. 14, 2019 in Russian Patent Application No. 2015128078, and English translation thereof.

(56) References Cited

OTHER PUBLICATIONS

Office Action dated Apr. 5, 2019 in Canadian Patent Application No. 2,872,045.

Mexican Patent Application No. MX/a/2015/010783, Office Action dated Sep. 18, 2019.

Chen et al., 2000, "Boosting with recombinant vaccinia increases HPV-16 E7-specific T cell precursor frequencies of HPV-16 E7-expressing DNA vaccines," Vaccine, 18(19):2015-2022.

Fiander et al., 2006, "Prime-boost vaccination strategy in women with high-grade, noncervical anogenital intraepithelial neoplasia: clinical results from a multicenter phase II trial," Int J Gynecol Cancer, 16(3):1075-1081, abstract only.

Goldberg et al., 2005, "Comparison of two cancer vaccines targeting tyrosinase: plasmid DNA and recombinant alphavirus replicon particles," Clin Cancer Res., 11(22):8114-8121.

Hung et al 2008, "Therapeutic human papillomavirus vaccines: current clinical trials and future directions," Expert Opin Biol Ther., 8(4):421-439.

Kast, 2008, "VEEV Replicon-Based Vaccines Used in Heterologous Prime Boost Strategies Induce Lifelong Protection Against Prostate Cancer and Therapy of Cervical Cancer in Mice and Robust Cell-Mediated Immunity in Rhesus macaques" in "Vaccine Technology II" (26 pages).

Lin et al., 2003, "Boosting with recombinant vaccinia increases HPV-16 E7-Specific T cell precursor frequencies and antitumor effects of HPV-16 E7-expressing Sindbis virus replicon particles," Mol Ther., 8(4):559-566.

Mackova et al., 2006, "Prime/boost immunotherapy of HPV16-induced tumors with E7 protein delivered by Bordetella adenylate cyclase and modified vaccinia virus Ankara," Cancer Immunol. Immunother, 55(1):39-46.

Rittich et al., 2005, "Combined immunization with DNA and transduced tumor cells expressing mouse GM-CSF or IL-2," Oncol Rep., 13(2):311-317.

Smyth et al., 2004, "Immunological responses in women with human papillomavirus type 16 (HPV-16)-associated anogenital intraepithelial neoplasia induced by heterologous prime-boost HPV-16 oncogene vaccination," Clin Cancer Res., 10(9):2954-2961.

Suksanpaisan et al., 2018, "Preclinical Development of Oncolytic Immunovirotherapy for Treatment of HPVPOS Cancers," Mol Ther Oncolytics., 10:1-13.

Tanaka et al., 2002, "Induction of a systemic immune response by a polyvalent melanoma-associated antigen DNA vaccine for prevention and treatment of malignant melanoma," Mol Ther., 5(3):291-299.

Wlazlo et al., 2004, "DNA vaccines against the human papillomavirus type 16 E6 or E7 oncoproteins," Cancer Gene Ther., 11(6):457-464.

\* cited by examiner

VACCINE COMPOSITION

CROSS REFERENCE TO RELATED APPLICATIONS

This application is a continuation of U.S. patent application Ser. No. 14/769,035, filed on Aug. 19, 2015, which is a U.S. National Stage Entry of PCT Patent Application No. PCT/CA2014/050118, filed Feb. 20, 2014, which claims the benefit of and priority to U.S. Provisional Patent Application No. 61/767,776 filed Feb. 21, 2013, all of which are hereby incorporated by reference in their entirety for all purposes.

FIELD

The present disclosure relates to oncolytic viruses for inducing an immune response.

BACKGROUND

Oncolytic viruses (OVs) specifically infect, replicate in and kill malignant cells, leaving normal tissues unaffected. Several OVs have reached advanced stages of clinical evaluation for the treatment of various neoplasms (Russell S J. et al., (2012) Nat Biotechnol 30:658-670). Once approved, such viral agents could substitute or combine with standard cancer therapies and allow for reduced toxicity and improved therapeutic efficacy.

In addition to the vesicular stomatitis virus (VSV) (Stojdl D F. et al., (2000) Nat Med 6:821-825; Stojdl D F. et al., (2003) Cancer Cell 4:263-275), other rhabdoviruses displaying oncolytic activity have been described recently (Brun J. et al., (2010) Mol Ther 18: 1440-1449; Mahoney D J. et al., (2011) Cancer Cell 20:443-456). Among them, the non-VSV Maraba virus showed the broadest oncotropism in vitro (WO 2009/016433). A mutant Maraba virus with improved tumor selectivity and reduced virulence in normal cells was engineered. The attenuated strain is a double mutant strain containing both G protein (Q242R) and M protein (L123W) mutations. In vivo, this attenuated strain, called MG1 or Maraba MG1, demonstrated potent anti-tumor activity in xenograft and syngeneic tumor models in mice, with superior therapeutic efficacy than the attenuated VSV, VSV.6M51 (WO 2011/070440).

Data accumulated over the past several years has revealed that anti-tumor efficacy of oncolytic viruses not only depends on their direct oncolysis but may also depend on their ability to stimulate anti-tumor immunity (Bridle S W. et al., (2010) Mol Ther 184:4269-4275). This immune-mediated tumor control seems to play a critical role in the overall efficacy of OV therapy. Indeed, tumor-specific adaptive immune cells can patrol the tissues and destroy tumor cells that have been missed by the OV. Moreover, their memory compartment can prevent tumor recurrence.

Various strategies have been developed to improve OV-induced anti-tumor immunity (Pol J. et al., (2012) Virus Adaptation and Treatment 4:1-21). Some groups have genetically engineered OV expressing immunomostimulatory cytokines. A herpes simplex and a vaccinia virus expressing Granulocyte-Macrophage Colony-Stimulating Factor (GM-CSF) have respectively reached phase III and IIB of the clinical evaluation for cancer therapy while a VSV expressing IFN-β has just entered phase I.

Another strategy, defined as an oncolytic vaccine, consists of expressing a tumor antigen from the OV (Russell S J. et al., (2012) Nat Biotechnol 30:658-670). Previously, it has been demonstrated that VSV could also be used as a cancer vaccine vector (Bridle B W. et al., (2010) Mol Ther 184: 4269-4275). When applied in a heterologous prime-boost setting to treat a murine melanoma model, a VSV-human dopachrome tautomerase (hDCT) oncolytic vaccine not only induced an increased tumor-specific immunity to DCT but also a concomitant reduction in antiviral adaptive immunity. As a result, the therapeutic efficacy was dramatically improved with an increase of both median and tong term survivals (WO 2010/105347). Although VSV was shown to be effective using hDCT as a tumor associated antigen, there is no way to predict what tumor associated antigens will be effective in a heterologous prime-boost setting.

It is desirable to provide a vaccine vector that can be used to activate the patient's immune system to kill tumor cells with reduced toxicity to normal tissues, for example by activating antibodies and/or lymphocytes against a tumor associated antigen on the tumor. It is desirable if such a vaccine vector displays both oncolytic activity and an ability to boost adaptive cell immunity.

SUMMARY

The following summary is intended to introduce the reader to one or more inventions described herein but not to define any one of them.

It is an object of the present disclosure to obviate or mitigate at least one disadvantage of previous anti-cancer vaccines.

The authors of the present disclosure have surprisingly determined that MAGEA3, Human Papilloma Virus E6/E7 fusion protein, human Six-Transmembrane Epithelial Antigen of the Prostate protein, and Cancer Testis Antigen 1, are all able to be used in a heterologous prime-boost setting to induce an immune response in a mammal. These results are unexpected and not predictable since not all tumor associated antigens are able to induce an immune response via a heterologous prime-boost. For example, the authors of the present disclosure also determined that Placenta-specific protein 1 (PLAC-1) and Epstein-Barr Nuclear Antigen 1 were unable to stimulate an immune response via a heterologous prime-boost.

In a first aspect, there is provided a kit for use in inducing an immune response in a mammal. The kit includes: a first virus that expresses a protein comprising an amino acid sequence of SEQ ID NO: 1, or a variant thereof, as an antigenic protein and that is formulated to generate an immunity to the protein or variant thereof in the mammal. The kit also includes a Maraba MG1 virus encoding a protein comprising an amino acid sequence SEQ ID NO: 1, or a variant thereof, as an antigenic protein, the Maraba MG1 virus formulated to induce the immune response in the mammal; the first virus being immunologically distinct from the Maraba MG1 virus. The antigenic protein expressed by the first virus and the antigenic protein expressed by the Maraba MG1 virus may be identical.

The first virus, the Maraba MG1 virus, or both, may be formulated for administration as isolated viruses.

The Maraba MG1 virus may include a reverse complement and RNA version of a transgene comprising a nucleotide sequence of SEQ ID NO: 2. The Maraba MG1 virus may include a reverse complement and RNA version of a codon optimized transgene comprising a nucleotide sequence of SEQ ID NO: 3.

The first virus may include a transgene comprising a nucleotide sequence of SEQ ID NO: 2 or 3, or may include a reverse complement and RNA version of a transgene comprising a nucleotide sequence of SEQ ID NO: 2 or 3, depending on whether the first virus is a positive sense RNA virus, a DNA virus, or a negative sense RNA virus.

The two viruses may be capable of expressing different variants of the protein that comprises the sequence of SEQ ID NO: 1. The variant of the protein comprising an amino acid sequence of SEQ ID NO: 1 that is expressed by the first virus, the Maraba MG1 virus, or both, may include at least one tumor associated epitope selected from the group consisting of: FLWGPRALV (SEQ ID NO: 27), KVAELVHFL (SEQ ID NO: 28), EGDCAPEEK (SEQ ID NO: 35), KKLLTQHFVQENYLEY (SEQ ID NO: 36), and RKVAELVHFLLLKYR (SEQ ID NO: 37), and be at least 70% identical to SEQ ID NO: 1. Preferably, the variant will be at least 80% identical to SEQ ID NO: 1. More preferably, the variant will be at least 90% identical to SEQ ID NO: 1. Even more preferably, the variant will be at least 95% identical to SEQ ID NO: 1.

The variant of the protein comprising an amino acid sequence of SEQ ID NO: 1 that is expressed by the first virus, the Maraba MG1 virus, or both, may have an amino acid sequence of SEQ ID NO: 4. The nucleotide sequence that encodes the variant may include a nucleotide sequence of SEQ ID NO: 5.

The Maraba MG1 virus may include a reverse complement and RNA version of a nucleotide sequence of SEQ ID NO: 5. The first virus may include a transgene comprising a nucleotide sequence of SEQ ID NO: 5, or may include a reverse complement and RNA version of a transgene comprising a nucleotide sequence of SEQ ID NO: 5, depending on whether the first virus is a positive sense RNA virus, a DNA virus, or a negative sense RNA virus.

If the first virus is a negative sense RNA virus, one of either the Maraba MG1 virus or the first virus may include a reverse complement and RNA version of a nucleotide sequence of SEQ ID NO: 2 or 3, and the other of the Maraba MG1 virus and the first virus may include a reverse complement and RNA version of SEQ ID NO: 5.

If the first virus is a positive sense RNA virus or a DNA virus, the Maraba MG1 virus may include a reverse complement and RNA version of a nucleotide sequence of SEQ ID NO: 2 or 3, and the first virus may include a nucleotide sequence of SEQ ID NO: 5. Alternatively, the Maraba MG1 virus may include a reverse complement and RNA version of a nucleotide sequence of SEQ ID NO: 5, and the first virus may include a nucleotide sequence of SEQ ID NO: 2 or 3.

One of either the Maraba MG1 virus or the first virus may be capable of expressing a protein that comprises the sequence of SEQ ID NO: 1 or 4, and the other of the Maraba MG1 virus and the first virus may be capable of expressing a protein that comprises the other sequence.

The first virus may be an adenovirus.

According to another aspect, there is provided an isolated Maraba MG1 viral particle having a genome that encodes a protein comprising an amino acid sequence of SEQ ID NO: 1, or a variant thereof.

The variant of the protein comprising an amino acid sequence of SEQ ID NO: 1 may have an amino acid sequence of SEQ ID NO: 4.

The genome may include a reverse complement and RNA version of a nucleotide sequence of SEQ ID NO: 2 or 3.

The genome may include a reverse complement and RNA version of a nucleotide sequence of SEQ ID NO: 5.

The genome may include a reverse complement and RNA version of a nucleotide sequence of SEQ ID NO: 6.

In another aspect, there is provided a kit for use in inducing an immune response in a mammal. The kit includes: a first virus that expresses a protein comprising an amino acid sequence of SEQ ID NO: 7, or a variant thereof, as an antigenic protein and that is formulated to generate an immunity to the protein or variant thereof in the mammal. The kit also includes a Maraba MG1 virus encoding a protein comprising an amino acid sequence of SEQ ID NO: 7, or a variant thereof, as an antigenic protein, the Maraba MG1 virus formulated to induce the immune response in the mammal; the first virus being immunologically distinct from the Maraba MG1 virus. The antigenic protein expressed by the first virus and the antigenic protein expressed by the Maraba MG1 virus may be identical.

The first virus, the Maraba MG1 virus, or both, may be formulated for administration as isolated viruses.

If the first virus is a negative sense RNA virus, the Maraba MG1 virus, the first virus, or both may include a reverse complement and RNA version of a codon optimized transgene comprising a nucleotide sequence of SEQ ID NO: 8. If the first virus is a DNA virus or a positive sense RNA virus, the first virus may include a codon optimized transgene comprising a nucleotide sequence of SEQ ID NO: 8.

The variant of the protein comprising an amino acid sequence of SEQ ID NO: 7 that is expressed by the first virus, the Maraba MG1 virus, or both, may include at least one tumor associated epitope and be at least 70% identical to SEQ ID NO: 7. Preferably, the variant will be at least 80% identical to SEQ ID NO: 7. More preferably, the variant will be at least 90% identical to SEQ ID NO: 7. Even more preferably, the variant will be at least 95% identical to SEQ ID NO: 7.

One of either the Maraba MG1 virus or the first virus may be capable of expressing a protein that comprises the sequence of SEQ ID NO: 7, and the other of the Maraba MG1 virus and the first virus may be capable of expressing a variant of a protein that comprises the sequence of SEQ ID NO: 7. The two viruses may be capable of expressing different variants of the protein that comprises the sequence of SEQ ID NO: 7.

The first virus may be a lentivirus.

According to another aspect, there is provided an isolated Maraba MG1 viral particle having a genome that encodes a protein comprising an amino acid sequence of SEQ ID NO: 7, or a variant thereof.

The genome may include a reverse complement and RNA version of a nucleotide sequence of SEQ ID NO: 8.

The genome may include a nucleotide sequence that is the reverse complement and RNA version of SEQ ID NO: 9.

In another aspect, there is provided a kit for use in inducing an immune response in a mammal. The kit includes: a first virus that expresses a protein comprising an amino acid sequence of SEQ ID NO: 10, or a variant thereof, as an antigenic protein and that is formulated to generate an immunity to the protein or variant thereof in the mammal. The kit also includes a Maraba MG1 virus encoding a protein comprising an amino acid sequence of SEQ ID NO: 10, or a variant thereof, as an antigenic protein, the Maraba MG1 virus formulated to induce the immune response in the mammal; the first virus being immunologically distinct from the Maraba MG1 virus. The antigenic protein expressed by the first virus and the antigenic protein expressed by the Maraba MG1 virus may be identical.

The first virus, the Maraba MG1 virus, or both, may be formulated for administration as isolated viruses.

If the first virus is a negative sense RNA virus, the Maraba MG1 virus, the first virus, or both may include a reverse complement and RNA version of a codon optimized transgene comprising a nucleotide sequence of SEQ ID NO: 11. If the first virus is a DNA virus or a positive sense RNA virus, the first virus may include a codon optimized transgene comprising a nucleotide sequence of SEQ ID NO: 11.

The variant of the protein comprising an amino acid sequence of SEQ ID NO: 10 that is expressed by the first virus, the Maraba MG1 virus, or both, may include at least one tumor associated epitope and be at least 70% identical to SEQ ID NO: 10. Preferably, the variant will be at least 80% identical to SEQ ID NO: 10. More preferably, the variant will be at least 90% identical to SEQ ID NO: 10. Even more preferably, the variant will be at least 30 95% identical to SEQ ID NO: 10.

One of either the Maraba MG1 virus or the first virus may be capable of expressing a protein that comprises the sequence of SEQ ID NO: 10, and the other of the Maraba MG1 virus and the first virus may be capable of expressing a variant of a protein that comprises the sequence of SEQ ID NO: 10. The two viruses may be capable of expressing different variants of the protein that comprises the sequence of SEQ ID NO: 10.

The first virus may be a lentivirus.

According to another aspect, there is provided an isolated Maraba MG1 viral particle having a genome that encodes a protein comprising an amino acid sequence of SEQ ID NO: 10, or a variant thereof.

The genome may include a reverse complement and RNA version of a nucleotide sequence of SEQ ID NO: 11.

The genome may include a nucleotide sequence that is the reverse complement and RNA version of SEQ ID NO: 12.

In another aspect, there is provided a kit for use in inducing an immune response in a mammal. The kit includes: a first virus that expresses a protein comprising an amino acid sequence of SEQ ID NO: 13, or a variant thereof, as an antigenic protein and that is formulated to generate an immunity to the protein or variant thereof in the mammal. The kit also includes a Maraba MG1 virus encoding a protein comprising an amino acid sequence of SEQ ID NO: 13, or a variant thereof, as an antigenic protein, the Maraba MG1 virus formulated to induce the immune response in the mammal; the first virus being immunologically distinct from the Maraba MG1 virus. The antigenic protein expressed by the first virus and the antigenic protein expressed by the Maraba MG1 virus may be identical.

The first virus, the Maraba MG1 virus, or both, may be formulated for administration as isolated viruses.

If the first virus is a negative sense RNA virus, the Maraba MG1 virus, the first virus, or both may include a reverse complement and RNA version of a codon optimized transgene comprising a nucleotide sequence of SEQ ID NO: 14. If the first virus is a DNA virus or a positive sense RNA virus, the first virus may include a codon optimized transgene comprising a nucleotide sequence of SEQ ID NO: 14.

The variant of the protein comprising an amino acid sequence of SEQ ID NO: 13 that is expressed by the first virus, the Maraba MG1 virus, or both, may include at least one tumor associated epitope and be at least 70% identical to SEQ ID NO: 13. Preferably, the variant will be at least 80% identical to SEQ ID NO: 13. More preferably, the variant will be at least 90% identical to SEQ ID NO: 13. Even more preferably, the variant will be at least 95% identical to SEQ ID NO: 13.

One of either the Maraba MG1 virus or the first virus may be capable of expressing a protein that comprises the sequence of SEQ ID NO: 13, and the other of the Maraba MG1 virus and the first virus may be capable of expressing a variant of a protein that comprises the sequence of SEQ ID NO: 13. The two viruses may be capable of expressing different variants of the protein that comprises the sequence of SEQ ID NO: 13.

The first virus may be a lentivirus.

According to another aspect, there is provided an isolated Maraba MG1 viral particle having a genome that encodes a protein comprising an amino acid sequence of SEQ ID NO: 13, or a variant thereof.

The genome may include a reverse complement and RNA version of a nucleotide sequence of SEQ ID NO: 14.

The genome may include a nucleotide sequence that is the reverse complement and RNA version of SEQ ID NO: 15.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

DETAILED DESCRIPTION

Figure 1A:
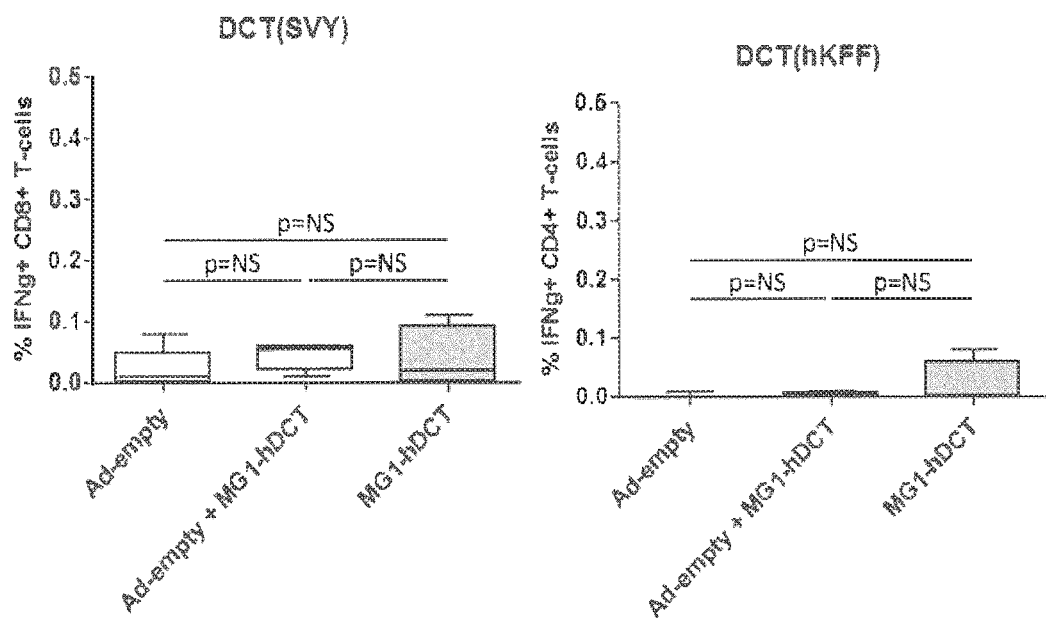
FIG. 1A shows the $CD8^+$ or $CD4^+$ T-cell responses in tumor-bearing mice administered with MG1-hDCT.

The present disclosure provides a kit for use in inducing an immune response in a mammal. The kit includes a first virus that expresses MAGEA3, a Human Papilloma Virus E6/E7 fusion protein, human Six-Transmembrane Epithelial Antigen of the Prostate protein, or Cancer Testis Antigen 1, or a variant thereof, as an antigen and that is formulated to generate an immunity to the antigen in the mammal. The kit also includes a Maraba MG1 virus encoding the same antigen, or a variant of the same antigen, the Maraba MG1 virus formulated to induce the immune response in the mammal. The first virus is immunologically distinct from the Maraba MG1 virus so that it may act as the "prime" in a heterologous prime-boost vaccination.

Prime: boost immunizations can be given with unmatched vaccine delivery methods while using the same antigen, in a 'heterologous' prime-boost format; or with matched vaccine delivery methods, in a 'homologous' prime-boost. Heterologous prime-boost methods are preferable when using vectored vaccine platforms as homologous vaccination would lead to boosting of responses to both the vector and the transgene in the secondary response. In contrast, a heterologous system focuses the secondary response (that is, the boosted response) on the antigen as responses against the first and the second vector are primary responses, and are therefore much less robust.

In the present disclosure, the first virus and the Maraba MG1 virus are used in a heterologous prime-boost format.

The antigenic proteins listed above are self-antigens already tolerized by the immune system through a tightly controlled process of negative selection in the thymus (Kruisbeek A M and Amsen D, (1996) Curr Opin Immunol 8:233-244; Stockinger B (1999) Adv Immunol 71:229-265) or peripheral tolerization. The major challenge with developing vaccines to these antigenic proteins, and any other self-antigens, is to induce a strong immune response directed selectively against cancer cells. Although a number of tumor associated antigenic peptides have been discovered, the authors of the present disclosure have determined that is impossible to predict which tumor associated antigenic peptides can be successfully used to develop vaccines.

Melanoma antigen, family A,3 (MAGEA3) is a "cancer testis antigen". The MAGE family of genes encoding tumor specific antigens is discussed in De Plaen et al., Immunogenetics 40:360-369 (1994), MAGEA3 is expressed in a wide variety of tumors including melanoma, colorectal and lung. This protein was used by the authors of the present disclosure as the antigenic protein in both the first virus and the Maraba MG1 virus. The authors also used a variant of the MAGEA3 protein as the antigenic protein in both the first virus and the Maraba MG1 virus.

Human Papilloma Virus (HPV) oncoproteins E6/E7 are constitutively expressed in cervical cancer (Zur Hausen, H (1996) Biochem Biophys Acta 1288:F55-F78). Furthermore, HPV types 16 and 18 are the cause of 75% of cervical cancer (Walboomers J M (1999) J Pathol 189:12-19). The authors of the present disclosure used a fusion protein of the E6/E7 oncoproteins of HPV types 16 and 18 as the antigenic protein. The fusion protein was expressed using a nucleotide sequence coexpressing HPV type 16/18 E6/E7 as a fusion protein, which was mutated to remove oncogenic potential. The fusion protein was used by the authors of the present disclosure as the antigenic protein in both the first virus and the Maraba MG1 virus.

Six-Transmembrane Epithelial Antigen of the Prostate (huSTEAP) is a recently identified protein shown to be overexpressed in prostate cancer and up-regulated in multiple cancer cell lines, including pancreas, colon, breast, testicular, cervical, bladder, ovarian, acute lyphocytic leukemia and Ewing sarcoma (Hubert R S et al., (1999) Proc Natl Acad Sci 96: 14523-14528). The STEAP gene encodes a protein with six potential membrane-spanning regions flanked by hydrophilic amino- and carboxyl-terminal domains. This protein was used by the authors of the present disclosure as the antigenic protein in both the first virus and the Maraba MG1 virus.

Cancer Testis Antigen 1 (NYESO1) is a cancer/testis antigen expressed in normal adult tissues, such as testis and ovary, and in various cancers (Nicholaou T et al., (2006) Immunol Cell Biol 84:303-317). Cancer testis antigens are a unique family of antigens, which have restricted expression to testicular germ cells in a normal adult but are aberrantly expressed on a variety of solid tumors, including soft tissue sarcomas, melanoma and epithelial cancers. This protein was used by the authors of the present disclosure as the antigenic protein in both the first virus and the Maraba MG1 virus.

In contrast to the successful use of the MAGEA3, HPV E6/E7 fusion, the huSTEAP, and the NYESO1 proteins as antigenic proteins in a heterologous prime-boost vaccine, the authors of the present disclosure determined that Epstein-Barr Nuclear Antigen 1 (EBDNA1, SEQ ID NO: 16, encoded by SEQ ID NO: 17) was unable to generate a similar immune response. EBDNA1 is a multifunctional viral protein associated with Epstein-Barr virus (EBV) (Sibille H et al., (2003) Proc Natl Acad Sci 100:10989-10994) and consistently expressed in EBV-associated tumors (Young L S et al., (2004) Nature Reviews—Cancer 4:757-768). EBNA1 has a glycine-alanine repeat sequence that separates the protein into amino- and carboxy-terminal domains (Young L S (2004) Nature Reviews—Cancer 4:757-768). This sequence also seems to stabilize the protein, preventing proteasomal breakdown, as well as impairing antigen processing and MHC class I-restricted antigen presentation. This thereby inhibits the CDB-restricted cytotoxic T cell response against virus-infected cells (Levitskaya J et al., (1995) Nature 375:685-688).

Placenta-specific protein 1 (PLAC-1) is another example of a tumor associated antigenic protein that was unable to generate an immune response in a heterologous prime-boost vaccine.

In the context of the present disclosure, a "variant" of a tumor associated antigenic protein refers to a protein that (a) includes at least one tumor associated antigenic epitope from the tumor associated antigenic protein and (b) is at least 70% identical to the tumor associated antigenic protein. Preferably, the variant will be at least 80% identical to the tumor associated antigenic protein. More preferably, the variant will be at least 90% identical to the tumor associated antigenic protein. Even more preferably, the variant will be at least 95% identical to the tumor associated antigenic protein. Variants with higher sequence identities have increased likelihood that the epitopes are presented in a similar 3-dimensional manner to the wild type antigenic proteins.

Generally, a tumor associated antigenic epitope may be identified by breaking up the whole antigenic protein into overlapping series of peptides, or by generating libraries of random peptides, and looking for T cell responses by stimulating PBMCs or splenocytes from animals vaccinated with the protein target using the peptide pools. Pools having a response identify that peptide as a potential antigenic epitope. This approach is discussed by Morris, G E in Encyclopedia of Life Sciences, 2007, page 1-3 (doi:10.1002/9780470015902.a0002624.pub2).

A database summarizing well accepted antigenic epitopes is provided by Van der Bruggen P, Stroobant V, Vigneron N, Van den Eynde Bin "Database of T cell-defined human tumor antigens: the 2013 update." *Cancer Immun* 2013 13:15 and at www.cancerimmunity.org/peptide/.

Tumor associated antigenic epitopes have been already identified for MAGEA3. Accordingly, a variant of the MAGEA3 protein may be, for example, an antigenic protein that includes at least one tumor associated antigenic epitope selected from the group consisting of: EVDPIGHLY (SEQ ID NO: 26), FLWGPRALV (SEQ ID NO: 27), KVAELVHFL (SEQ ID NO: 28), TFPDLESEF (SEQ ID NO: 29), VAELVHFLL (SEQ ID NO: 30), MEVDPIGHLY (SEQ ID NO: 31), REPVTKAEML (SEQ ID NO: 32), AELVHFLLL (SEQ ID NO: 33), WQYFFPVIF (SEQ ID NO: 34), EGDCAPEEK (SEQ ID NO: 35), KKLLTQHFVQENYLEY (SEQ ID NO: 36), RKVAELVHFLLLKYR (SEQ ID NO: 37), ACYEFLWGPRALVETS (SEQ ID NO: 38), VIFSKASSSLQL (SEQ ID NO: 39), VFGIELMEVDPIGHL (SEQ ID NO: 40), GDNQIMPKAGLLIIV (SEQ ID NO: 41), TSYVKVLHHMVKISG (SEQ ID NO: 42), RKVAELVHFLLLKYRA (SEQ ID NO: 43), and FLLLKYRAREPVTKAE (SEQ ID NO: 44); and that is at least 70% identical to the MAGEA3 protein.

It may be desirable for variants of a tumor associated antigenic protein to include only antigenic epitopes that have high allelic frequencies, such as frequencies greater than 40% of the population. Accordingly, preferred examples of variants of MAGEA3 may include proteins that include at least one antigenic epitope selected from the group consisting of: FLWGPRALV (SEQ ID NO: 27), KVAELVHFL (SEQ ID NO: 28), EGDCAPEEK (SEQ ID NO: 35), KKLLTQHFVQENYLEY (SEQ ID NO: 36), and RKVAELVHFLLLKYR (SEQ ID NO: 37) and that is at least 70% identical to the MAGEA3 protein.

The antigen expressed by the first virus does not need to have exactly the same sequence as the antigen expressed by the Maraba MG1 virus. The antigen expressed by Maraba MG1 must only induce an overlapping immune response to the antigen expressed by the first virus. For example, the first virus may express the MAGEA3 and the Maraba MG virus may express a MAGEA3 variant, or vice versa. Since both MAGEA3 and the variant of MAGEA3 induce overlapping immune responses (as they both include at least one identical tumor associated antigenic sequence), the first virus acts as the prime and the Maraba MG1 virus acts as the boost. It is sufficient that the immune response generated in the mammal to the first antigen results in an immune response primarily to the MAGEA3 or MAGEA3 variant when the Maraba MG1 virus is administered.

In the context of the present disclosure, it should be understood that all discussions of, and references to, a 'protein expressed by a virus' more exactly refer to a protein expressed by a cell infected with the virus since viruses do not themselves have the capability to express proteins. Similarly, all discussions of, and references to, a 'virus that expresses a protein' or 'virus capable of expressing a protein' more exactly refer to a virus that includes the genetic information necessary for the protein to be expressed by a cell infected with the virus.

The kit may additionally include an immune-potentiating compound, such as cyclophosphamide (CPA), that increases the prime immune response to the tumor associated antigenic protein generated in the mammal by administrating the first virus. Cyclophosphamide is a chemotherapeutic agent that may lead to enhanced immune responses against the tumor associated antigenic protein. In a synergistic murine melanoma 25 tumor model, CPA administered prior to the priming vector significantly increased survival, while CPA administered prior to the boosting vector did not.

The therapeutic approach disclosed herein combines: (1) a viral vaccine, and (2) Maraba MG1 virus as an oncolytic viral vaccine, both expressing MAGEA3, Human Papilloma Virus E6/E7 fusion protein, human Six-Transmembrane Epithelial Antigen of the Prostate protein, or Cancer Testis Antigen 1, or a variant thereof. Boosting with the oncolytic vaccine may lead to both tumor debulking by the oncolytic virus and a large increase in the number of tumor-specific CTL (cytotoxic T-lymphocytes) in animals primed by the viral vaccine. Paradoxically, this methodology actually generates larger anti-tumor responses in tumor-bearing, as compared to tumor-free, animals since the replication of oncolytic virus is amplified in the tumor-bearing animals, which leads to an increase in the number of antigen-specific Tumor Infiltrating Lymphocytes (TILs), when compared to the replication of oncolytic virus in the tumor-free animals and the associated number of antigen-specific Tumor Infiltrating Lymphocytes (TILs).

The expression products of these genes are processed into peptides, which, in turn, are expressed on cell surfaces. This can lead to lysis of the tumor cells by specific CTLs. The T cell response to foreign antigens includes both cytolytic T lymphocytes and helper T lymphocytes. $CD8^+$ cytotoxic or cytolytic T cells (CTLs) are T cells which, when activated, lyse cells that present the appropriate antigen presented by HLA class I molecules. $CD4^+$ T helper cells are T cells which secrete cytokines to stimulate macrophages and antigen-producing B cells which present the appropriate antigen by HLA class II molecules on their surface.

The protein "MAGEA3" may be also referred to as "MAGE-A3" and stands for melanoma-associated antigen 3. The antigenic MAGEA3 protein according to the present disclosure is a protein that includes the amino acid sequence of SEQ ID NO: 1. This amino acid sequence may be encoded by the nucleotide sequence of SEQ ID NO: 2. Alternatively, the amino acid sequence may be encoded by a codon optimized transgene that includes the nucleotide sequence of SEQ ID NO: 3. A negative sense RNA virus that expresses the protein of SEQ ID NO: 1 may include a reverse complement and RNA version of a polynucleotide of SEQ ID NO: 2 or 3. A positive sense RNA virus or a DNA virus that expresses the protein of SEQ ID NO: 1 may include a sequence that is SEQ ID NO: 2 or 3.

An example of an antigenic MAGEA3 variant protein according to the present disclosure is a protein that includes the amino acid sequence of SEQ ID NO: 4. This amino acid sequence may be encoded by the nucleotide sequence of SEQ ID NO: 5. A negative sense RNA virus that expresses the protein of SEQ ID NO: 4 may include an RNA polynucleotide which includes a sequence that is a reverse complement and RNA version of SEQ ID NO: 5. A DNA virus or RNA virus that expresses the protein of SEQ ID NO: 4 may include a sequence that is SEQ ID NO: 5.

One example of such a negative sense RNA virus is a Maraba virus that includes the reverse complement and RNA version of SEQ ID NO: 6.

The antigenic protein "E6/E7 fusion protein" or "Human Papilloma Virus E6/E7 fusion protein" according to the present disclosure is a protein that includes the amino acid sequence of SEQ ID NO: 7. This amino acid sequence may be encoded by the nucleotide sequence of SEQ ID NO: 8. A negative sense RNA virus that expresses the protein of SEQ ID NO: 7 may include a reverse complement and RNA version of a polynucleotide of SEQ ID NO: 8. A DNA virus or a positive sense RNA virus that expresses the protein of SEQ ID NO: 7 may include a polynucleotide of SEQ ID NO: 8. One example of such a negative sense RNA virus is a Maraba virus that includes the reverse complement and RNA version of SEQ ID NO: 9.

The protein "huSTEAP" or "human Six-Transmembrane Epithelial Antigen of the Prostate protein" according to the present disclosure is a protein that includes the amino acid sequence of SEQ ID NO: 10. This amino acid sequence may be encoded by the nucleotide sequence of SEQ ID NO: 11. A negative sense RNA virus that expresses the protein of SEQ ID NO: 10 may include a reverse complement and RNA version of a polynucleotide of SEQ ID NO: 11. A DNA virus or RNA virus that expresses the protein of SEQ ID NO: 10 may include a sequence that is SEQ ID NO: 11. One example of such a negative sense RNA virus is a Maraba virus that includes the reverse complement and RNA version of SEQ ID NO: 12.

The protein "NYESO1" or "human Cancer Testis Antigen 1" according to the present disclosure is a protein that includes the amino acid sequence of SEQ ID NO: 13. This amino acid sequence may be encoded by the nucleotide sequence of SEQ ID NO: 14. A negative sense RNA virus that expresses the protein of SEQ ID NO: 13 may include a reverse complement and RNA version of a polynucleotide of SEQ ID NO: 14. A DNA virus or RNA virus that expresses the protein of SEQ ID NO: 13 may include a sequence that is SEQ ID NO: 14. One example of such a negative sense RNA virus is a Maraba virus that includes the reverse complement and RNA version of SEQ ID NO: 15.

The above noted sequences are shown in Appendix A.

The term "mammal" refers to humans as well as non-human mammals. The term "cancer" is used herein to encompass any cancer that expresses the tumor associated antigenic protein (that is: MAGEA3, Human Papilloma Virus E6/E7 fusion protein, human Six-Transmembrane Epithelial Antigen of the Prostate protein, or Cancer Testis Antigen 1) used in the viruses of interest.

For example, when considering MAGEA3 as an antigenic protein, the term "cancer" encompasses any cancer that expresses MAGEA3 as an antigen. Examples of such a cancer include, but are not limited to, melanoma, non-small cell lung cancer, head and neck cancer, colorectal cancer, and bladder cancer.

When considering E6/E7 fusion protein as an antigenic protein, the term "cancer" encompasses any cancer that expresses E6 and E7 proteins as antigenic proteins. Examples of such a cancer include, but are not limited to, cervical cancer.

The first virus, the Maraba MG1 virus, or both may be independently administered to the mammal intravenously, intramuscularly, intraperitoneally, or intranasally. Following administration of the viruses, an immune response is generated by the mammal within an immune response interval, e.g. within about 4 days, and extending for months, years, or potentially life.

The first virus may be any virus that induces an immune response to the tumor associated antigenic protein or variant thereof after the first virus is administered to the patient. Viruses that may be used according to the present disclosure include, for example: adenovirus (Ad), poxvirus, retrovirus, and alpha virus. An example of a poxvirus is vaccinia virus. An example of a retrovirus is lentivirus. An example of an alpha virus is semliki forest virus.

To establish an immune response to the tumor associated antigenic protein or variant thereof, vaccination using the first virus and the Maraba MG1 virus may be conducted using well-established techniques. As one of skill in the art will appreciate, the amount of virus required to generate an immune response will vary with a number of factors, including, for example, the selected antigen, the viral vector used to deliver the antigen, and the mammal to be treated, e.g. species, age, size, etc. In this regard, for example, intramuscular administration of at least about $10^7$ PFU of Adenoviral vector to a mouse is sufficient to generate an immune response. A corresponding amount would be sufficient for administration to a human to generate an immune response.

Once an immune response has been generated in the mammal by administration of the first virus, Maraba MG1 virus encoding the tumor associated antigenic protein or a variant thereof is administered in an amount suitable for oncolytic viral therapy within a suitable immune response interval. A suitable immune response interval may be, for example, at least about 24 hours, preferably at least about 2-4 days or longer, e.g. at least about 1 week, or at least about 2 weeks. The amount of Maraba MG1 virus suitable for oncolytic viral therapy will vary with the mammal to be treated, as will be appreciated by one of skill in the art. For example, $10^8$ PFU of Maraba MG1 virus encoding MAGEA3 administered IV to a mouse is sufficient for oncolytic therapy. A corresponding amount would be sufficient for use in a human.

Maraba MG1 virus encoding tumor associated antigenic protein or a variant thereof may be prepared by incorporating a reverse complement of a transgene encoding the tumor associated antigenic protein or a variant thereof into the Maraba MG1 virus using standard recombinant technology. For example, the reverse complement of the transgene may be incorporated into the genome of the Marama MG1 virus, or alternatively, may be incorporated into the virus using a plasmid incorporating the transgene. The transgene encoding the tumor may be a codon optimized transgene.

EXAMPLES

The oncolytic Maraba MG1 is a potent oncolytic vaccine platform. While unable to prime detectable responses against a melanoma-associated antigen, Maraba MG1-vaccine displayed the ability to boost preexisting tumor-specific CD4$^+$ and CD8$^+$ T-cell immunity. When applied to the treatment of syngeneic murine melanoma tumor models, Maraba-MG1-mediated recall immunization resulted in an extension of the median survival with complete remission in more than 20% of the animals treated.

In a primate toxicity study heterologous prime-boost vaccination with an Ad-MAGEA3 prime followed by a Maraba-MG1-MAGEA3 boost resulted in T-cell responses that were comparable to those obtained in syngeneic murine tumor models demonstrating that in an outbred primate population the prime-boost oncolytic vaccine strategy gives immune responses comparable to animal models where tumors can be engrafted and a dramatic extension of survival is attained.

The authors of the present disclosure also determined that proteins having the sequence SEQ ID NOs: 7, 10, or 13 could be used to stimulate an immune response in a patient using a heterologous prime boost with Maraba MG1. In contrast, the authors of the present disclosure determined that administration of a first virus expressing EBDNA-1 protein or Placenta-specific protein 1 (PLAC-1) followed by administration of Maraba-MG1 expressing EBDNA-1 protein or PLAC-1, respectively, was unable to stimulate an immune response.

Example 1: MG1-hDCT is a Weak Priming Vector but a Potent Boosting Vector

Ad-empty and Ad-hDCT are replication-deficient adenoviruses (E1/E3-deletion) based on the human serotype 5 (Lane C. et al., (2004) Cancer Research 64:1509-1514; Ng P. et al., (2001) Mol Ther 3:809-815). The replication-deficient adenovirus vector was engineered to express the hDCT transgene, which encodes the full length human melanoma associated antigen DCT (dopachrome tautomerase) while Ad-empty has no transgene. The resulting adenovirus vector is termed "Ad-hDCT".

The MG1 variant of Maraba virus was engineered to express the human form of the melanoma-associated antigen hDCT transgene. The resulting MG1 virus vector is termed "MG1-hDCT" or "Maraba MG1-hDCT". Other virus vectors are named using a similar convention.

Recombinant Maraba and VSV were generated by transgene insertion between the G and L viral genes. VSV-hDCT derives from the wild-type Indiana strain of the VSV (Bridle B W. et al. (2009) 17:1814-1821; Lawson N D. et al., (1995) Proc Natl Acad Sci USA 92:4477-4481). MG1-GFP (Green Flourescent Protein used as a control non-immunogenic transgene insertion) and MG1-hDCT derive from the attenuated strain MG1 of Maraba virus. Prior to in vivo studies, DCT (and GFP) expression from the virus was confirmed by western blot of lysates from infected Vero cells cultured in alpha-MEM containing 10% FBS, 2 mM L-glutamine, 100 U/ml penicillin, and 100 mg/ml streptomycin (all from Invitrogen, Grand Island, N.Y.).

The therapeutic efficacy of MG1-hDCT administered as a monotherapy was evaluated initially. In order to generate lung metastases, C57Bl/6 mice (8-10 weeks old at study initiation) were injected i.v. with $2.5 \times 10^5$ B16-F10 cells (murine melanoma cells expressing the murine DCT antigen) in 200 µl saline water. The oncolytic vaccine was injected systemically 5 or 14 days later and T-cell responses against the melanoma antigen DCT were measured in the blood at day 19. The virus was administered systemically at a high dose ($10^9$ pfu i.v in 200 µl PBS). T-cell responses were measured by isolating PBMCs or splenocytes and stimulating them with the SVYDFFVWL (SEQ ID NO: 45) (SVY) or KFFHRTCKCTGNFA (SEQ ID NO: 46), (KFF) peptides corresponding to the MHC-I or MHC-II restricted immunodominant epitopes of DCT, respectively. Responding T-cells were detected after intracellular cytokine staining (ICS) for IFN-γ by flow cytometry.

Figure 1B:
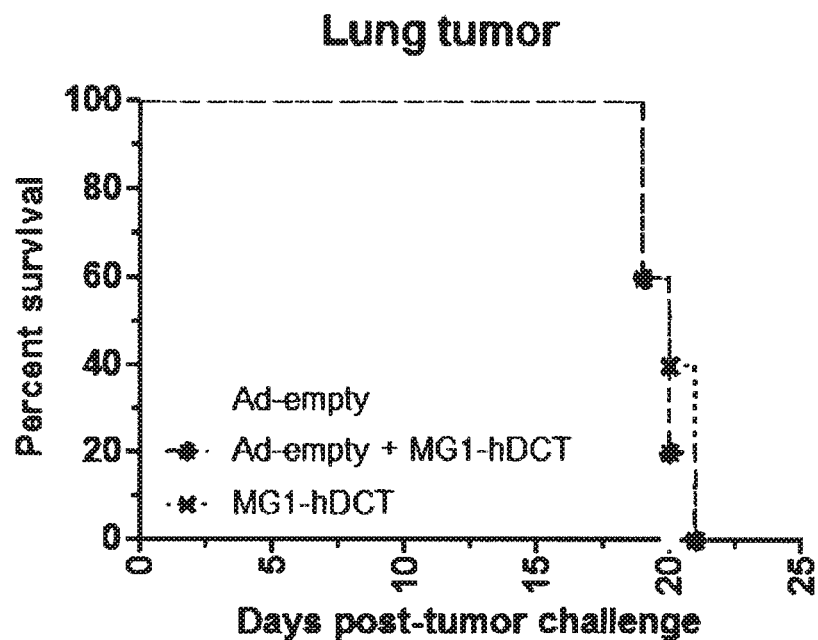
FIG. 1B shows the therapeutic efficacy of MG1-hDCT administered as a priming vector only in a metastatic lung cancer mouse model.

As shown in FIGS. 1A and 1B, MG1-hDCT was unable to prime DCT-specific CD8$^+$ or CD4$^+$ T-cell responses in tumor-bearing mice (FIG. 1A). Administered alone, the MG1-hDCT vaccine did not improve tumor outcome. Indeed, mice treated 14 days post-tumor challenge reached endpoint in a similar timeframe as untreated mice: after 20 days for the Ad-empty control group versus 21 days for the Ad-empty+MG1-hDCT group (FIG. 1B). Moreover, survival was not extended even when mice were treated with MG1-hDCT as early as 5 days after tumor engraftment (MG1-hDCT group, FIG. 1B). In conclusion, not only did MG1-hDCT fail to induce anti-DCT immunity but its oncolytic activity offered no therapeutic benefit. These results demonstrate that MG1-hDCT is unable to prime significant T-cell responses against the tumor antigen DCT and is thus a weak priming vector.

It was previously reported that an oncolytic VSV vector serves as a potent booster of pre-existing immunity (Bridle B W. et al., (2010) Mol Ther 184:4269-4275; WO 2010/105347). In the present disclosure, the ability of Maraba MG1 virus to serve as a booster vaccine was examined. Adenoviral vectors were used as priming vectors and administered intramuscularly (i.m.) at a total dose of $2 \times 10^8$ pfu ($1 \times 10^8$ pfu in 500 PBS per thigh). For adenovirus injection, mice were anesthetized in a sealed chamber containing 5% inhalation isoflurane. Using Ad-hDCT as a priming vector, MG1-hDCT was evaluated as a booster of pre-existing DCT-specific responses. To evaluate Maraba virus as a boosting vector, various routes of administration were evaluated. An oncolytic dose of $1 \times 10^9$ pfu of virus was administered that is well tolerated in this mouse strain and an interval of 12 days post-Ad priming was selected as this was the longest interval that would be feasible in the tumor model. When this dose of MG1-Maraba-hDCT was administered by intravenous (i.v.), intranasal (i.n.) and intramuscular (i.m.) routes, the i.v. route proved to be far superior as measured by ICS for IFN-γ in peripheral CD8$^+$ T-cells: 28.33%±3.82 by i.v. versus 4.73%±1.52 i.n. versus 13.84%±1.88 i.m. The responses were measured at day 5 post-Maraba administration coinciding with the peak of the MG1-hDCT-mediated boost response. In the intravenously boosted animals a significant proportion of DCT-specific CD8$^+$ T-cells was also measured in the spleen with a 3-fold increase in mice administered with both vaccine vectors compared to animals primed only: 3.45%±0.45 in Ad-hDCT group versus 11.02%±2.14 in the Ad-hDCT+MG1-hDCT immunized animals (p=0.0085**). While Ad-hDCT was unable to induce a detectable DCT-specific CD4$^+$ T-cell population in the blood and a barely detectable population in the spleen, the MG1 Maraba-hDCT booster was able to generate clear systemic CD4$^+$ T-cell response but only when administered i.v. (0.30%±0.11). The response was also detectable in the spleen with 0.14%±0.03 of splenic CD4$^+$ T-cells reacting to DCT KFF peptide exposure. Similar to VSV, maximal immune boosting by MG1 Maraba virus is achieved by i.v. administration. In conclusion, systemic delivery of a Maraba-vectored vaccine at a dose of $10^9$ pfu appeared to allow for efficient boosting of both antigen-specific CD8$^+$ and CD4$^+$ T-cell populations. For this reason, this route and dose were used for Maraba MG1 administration in subsequent in vivo experiments.

Figure 2:
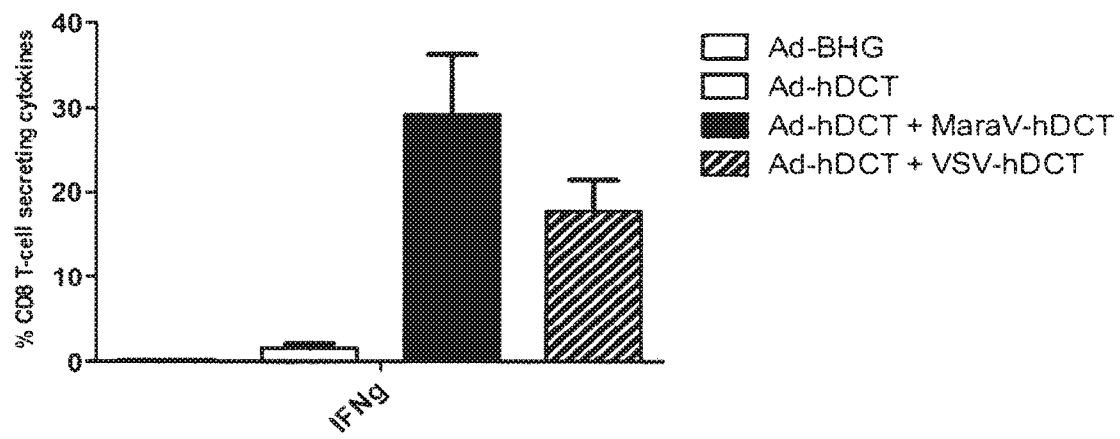
FIG. 2 shows the comparison of the immune response of a prime-boost vaccination in C57/Bl6 mice with Ad-hDCT as the priming vector and either Maraba MG1-hDCT or VSV-hDCT as the boosting vector.

To show that Maraba MG1-hDCT is a more potent boosting vector than VSV-hDCT, C57/B16 mice were primed with Ad-hDCT (Ad-BHG was included as a control vector lacking a transgene) and then boosted with an intravenous dose of either VSV-hDCT or Maraba-hDCT 14 days later. Immune analysis of CD8$^+$ T cell responses were measured in peripheral blood at day 5 post-boosting vector. At an equivalent dose the response induced by Maraba vaccination was 3-8 fold as large as the VSV-induced responses (FIG. 2).

Example 2: MG1-hDCT Vaccine Strategy in Murine Models of Cancer

Figure 3:
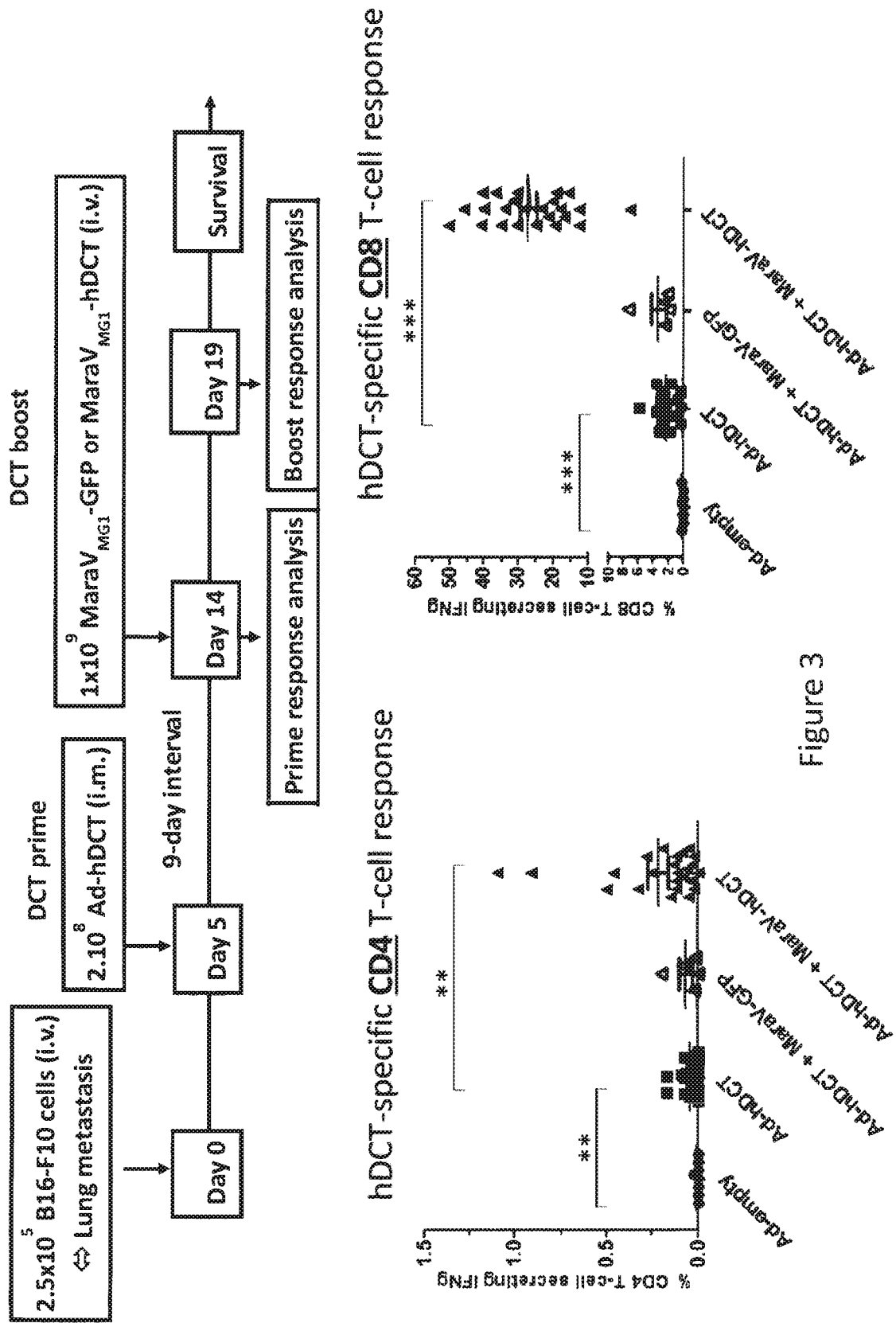
FIG. 3 shows the T-cell response in a metastatic lung cancer mouse model following Ad-empty or Ad-hDCT, as the priming vector only or following prime-boost vaccination with Ad-hDCT, as the priming vector and either Maraba MG1 GFP or Maraba MG1-hDCT, as the boosting vector.

The therapeutic efficacy of MG1-hDCT administered as a boosting vector was subsequently investigated. Five days following B16-F10 engraftment to generate lung metastases in animals, animals received an Ad-hDCT priming vaccine and this was followed 9 days later by a single i.v. dose of MG1 Maraba-hDCT as an oncolytic booster vaccine. Ad-hDCT prime-MG1-hDCT boost vaccination generated a very strong DCT-specific CD8$^+$ T-cell response (mean % IFN-$\gamma^+$CD8$^+$ T-cells=27.54±2.17, FIG. 3) that was 14 times higher than in non-boosted mice (1.95%±0.29 in Ad-hDCT group and 1.91%±0.59 in Ad-hDCT+MG1-GFP group, FIG. 3). Similarly, DCT-specific CD4$^+$ T-cell responses were measured in MG1-hDCT boosted animals while rarely detected in primed only mice (mean % IFN-$\gamma^+$CD4$^+$ T-cells=0.25%±0.06 in Ad-hDCT+MG1-hDCT group versus <0.05% in Ad-hDCT and Ad-hDCT+MG1-GFP groups, FIG. 3).

Figure 4:
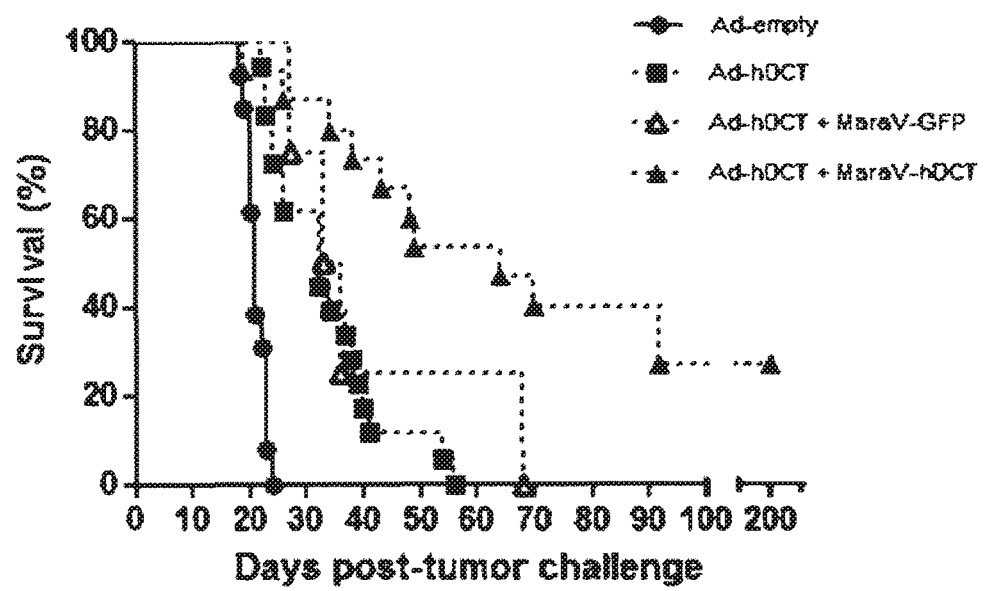
FIG. 4 shows the survival plot in a metastatic lung cancer mouse model following Ad-empty or Ad-hDCT, as the priming vector only or following prime-boost vaccination with Ad-hDCT, as the priming vector and either Maraba MG1 GFP or Maraba MG1-hDCT, as the boosting vector.

Looking at treatment outcome, Ad-hDCT immunization allowed a 10-day extension of the median survival compared to untreated mice: 31 days for Ad-hDCT treatment versus 20.5 days for Ad-empty group (FIG. 4). Ad-hDCT treatment followed by MG1 Maraba-GFP oncolytic treatment did not improve survival (27.5 days median survival for Ad-hDCT+MG1-GFP group, FIG. 4). However, boosting anti-tumor immunity with the Maraba MG1-DCT vaccine dramatically improved tumor outcome with a 20-day extension of the median survival compared to Ad-hDCT primed only animals (51 days for Ad-hDCT+MG1-hDCT group, FIG. 4). More importantly, the oncolytic MG1-hDCT booster treatment resulted in 23.3% long-term survival (FIG. 4).

In order to characterize the respective contribution of tumor-specific CD4$^+$ and CD8$^+$ T-cell responses in the therapeutic efficacy, each T-cell compartment was selectively depleted (data not shown). Depletion of the CD8$^+$ T-cell population at the time of the boost abrogated the therapeutic benefit of MG1-hDCT administration. On the contrary, CD4$^+$ T-cells depletion appeared not to affect significantly the therapeutic efficacy indicating that Maraba immune boosting of CD8$^+$ T cells is CD4$^+$-independent. While the critical role of CD8$^+$ T-cells in controlling tumor growth is admitted, these results show that boosting tumor-specific CD8$^+$ T-cells with Maraba vaccine is a potent way of improving cancer therapy.

Figure 5:
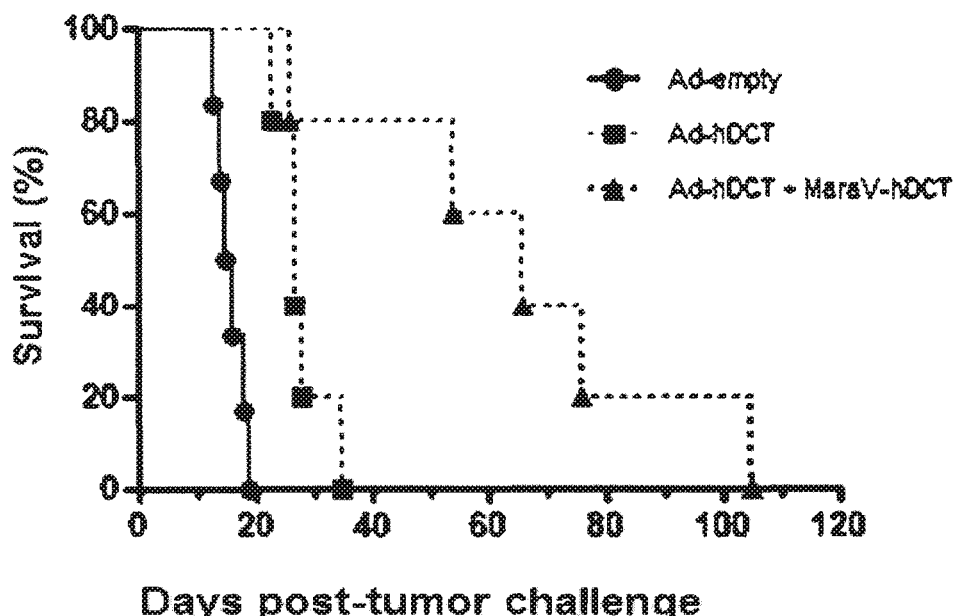
FIG. 5 shows the survival plot in a metastatic brain cancer mouse model following Ad-empty or Ad-hDCT, as the priming vector only or following prime-boost vaccination with Ad-hDCT, as the priming vector and Maraba MG1-hDCT, as the boosting vector.

Finally, the efficacy of the prime-boost strategy involving Maraba vaccine was also evaluated in a very challenging intracranial B16-F10 model of metastatic melanoma brain cancer. Ad-hDCT-mediated immunotherapy significantly improved survival of melanoma brain met-bearing mice with a median extended from 15 days for Ad-empty controls to 25.5 days for the Ad-hDCT group (FIG. 5). As previously reported, such therapeutic efficacy demonstrates the ability of the tumor-specific effector T-cells raised to cross the blood-brain barrier and infiltrate the tumor bed (Bridle B W. et al., (2010) Mol Ther 184:4269-4275). The additional administration of a Maraba MG1-hDCT oncolytic booster further improved tumor outcome with a median survival reaching 42 days together with cures observed in 21.4% of treated animals (Ad-hDCT+MG1-hDCT group, FIG. 5).

Example 3: Failure of Vaccine Strategy to Induce an Anti-mPLAC1 T Cell Response

Although Maraba MG1 and VSV were able to act as boosting vectors using hDCT as a tumor associated antigen, not all tumor associated antigens can be used in a heterologous prime-boost vaccine strategy. The authors of the present disclosure tested a heterologous prime-boost vaccine strategy using huAd5-mPLAC1 as the priming vector and VSV-mPLAC1 as the boosting vector.

PLAC1 is a recently described tumor associated antigen expressed in the placenta but has also been reported in several tumor cell lines and in tumors of patients breast, lung, liver, gastric and colorectal cancers (Silva, W A et al., (2007) Cancer Immun 7:18).

Ad-mPLAC1 is a replication-deficient adenoviruses (E1/E3-deletion) based on the human serotype 5 (Lane C. et al., (2004) Cancer Research 64:1509-1514; Ng P. et al., (2001) Mol Ther 3:809-815). The replication-deficient adenovirus vector was engineered to express the mPLAC1 transgene, which encodes the full length murine antigen PLAC1 (placenta-specific 1), the resulting adenovirus vector is termed "Ad-mPLAC1" or "huAd5-mPLAC1".

VSV virus was engineered to express the human form of the melanoma-associated antigen mPLAC1 transgene. The resulting VSV-virus vector is termed "VSVmPLAC1". Recombinant VSV was generated by transgene insertion between the G and L viral genes. VSV-mPLAC1 derives from the wild-type Indiana strain of the VSV (Bridle B W. Et al. (2009) 17:1814-1821; Lawson N D. et al., (1995) Proc Natl Acad Sci USA 92:4477-4481).

C57Bl/6 mice were primed with Ad-mPLAC1 (2×10$^9$ PFU IM injection) and then boosted with a single i.v.dose.of VSV-mPLAC1 (2×10$^9$ PFU) 14 days later. T-cell responses were measured by isolating splenocytes and stimulating them with individual 15 mmer peptides form an overlapping PLAC1 peptide library for a total of 6 hours with golgi plug added 1 hour into the stimulation. Following stimulation the splenocytes were stained for CD4, CD8 and IFN$\gamma$ and analyzed on FACSCanto and FlowJo. Responding T-cells were detected after intracellular cytokine staining (ICS) for IFN-$\gamma$ by flow cytometry. None of the mPLAC1 peptides were able to stimulate IFN-$\gamma$ production in either CD8 or CD4 T cells.

Figure 6:
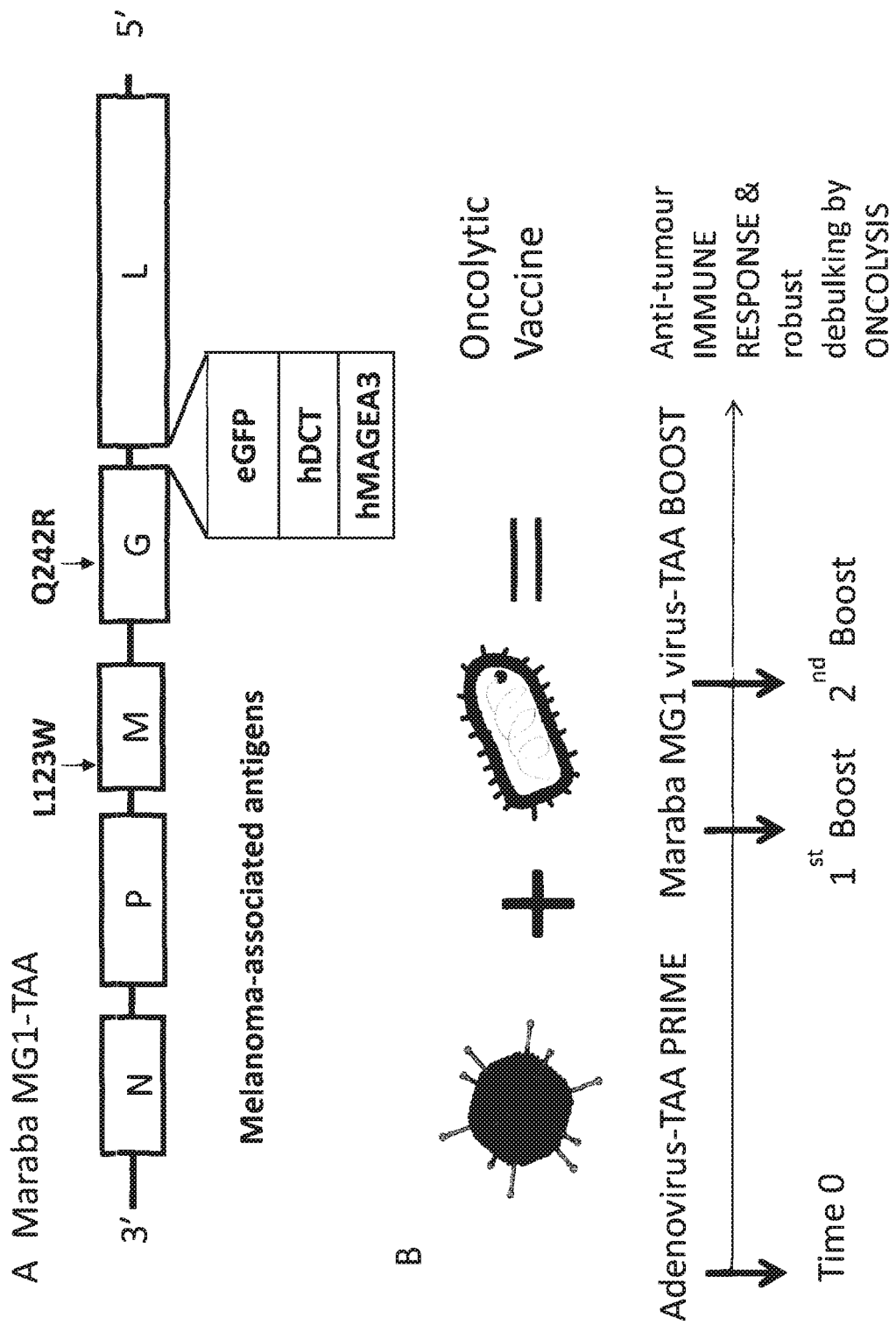
FIG. 6 is a diagram of the priming vector Ad-MAGEA3, the boosting vector Maraba MG1-MAGEA3 and the prime-boost strategy utilized in a primate toxicity/immunogenicity study.

Example 4: Construction of Oncolytic Vaccine Vectors with MAGEA3 or a Variant Thereof Ad-MAGEA3 is a replication-deficient adenovirus (E1/E3-deletion) based on the human serotype 5 (Lane C. et al., (2004) Cancer Research 64:1509-1514; Ng P. et al., (2001) Mol Ther 3:809-815) containing the full-length human MAGEA3 gene. Maraba MG1-hMAGEA3 has been developed and contains the codon-optimized full length human MAGEA3 gene inserted between the G and L viral genes of the MG1 double mutant of Maraba virus (Brun J. et al., (2010) Mol Ther 18:1440-1449). The MAGEA3 sequence (NCBI Gene ID: 4102 www.ncbi.nlm.nih.gov/gene/4102) was codon optimized for expression in mammalian cells and then synthesized with a FLAG tag on 3' end and with MluI restriction sites on both 3' and 5' ends. This sequence was ligated into the shuttle vector pMRB-MG1/pNF at its MluI site (between G and L genes) which contains part of the Maraba-MG1 genome from the beginning of G to the end of L genes, flanked by KpnI and NheI sites, respectively. The entire region from KpnI to NheI, now containing MAGEA3 Flag between G and L was then removed from pMRB-MG1/pNF and ligated back into the pMRB-MG1 genomic plasmid using KpnI and NheI sites. Maraba-MG1-MAGEA3 Flag was then rescued and plaque purified. This is illustrated in FIG. 6.

A full length human MAGEA3 protein expressed by the adenovirus may include the amino acid sequence of SEQ ID NO: 1. The adenovirus may include a nucleotide sequence of SEQ ID NO: 2. Alternatively, the amino acid sequence may be encoded by a codon optimized transgene that includes the nucleotide sequence of SEQ ID NO: 3. Accordingly, the adenovirus may include the codon-optimized nucleotide sequence of SEQ ID NO: 3.

The Maraba MG1 virus may include a reverse complement and RNA version of a nucleotide sequence of SEQ ID NO: 2. Alternatively, the amino acid sequence may be encoded by a codon optimized transgene that includes the nucleotide sequence of SEQ ID NO: 3. Accordingly, the Maraba MG1 virus may include the reverse complement and RNA version of the codon-optimized nucleotide sequence of SEQ ID NO: 3.

One variant of MAGEA3 is a protein that includes the amino acid sequence of SEQ ID NO: 4. This amino acid sequence may be encoded by the nucleotide sequence of SEQ ID NO: 5. The adenovirus may include a nucleotide sequence of SEQ ID NO: 5. The Maraba MG1 virus may include a reverse complement and RNA version of a nucleotide sequence of SEQ ID NO: 5.

A negative sense RNA virus, such as a Maraba virus, that expresses the protein of SEQ ID NO: 4 may include an RNA polynucleotide which includes a sequence that is a reverse complement and RNA version of SEQ ID NO: 6.

Example 5: MG1-MAGEA3 Vaccine Immune Response in Healthy Primates

Healthy cynomolgous monkeys were used in a study designed to collect toxicity and immunogenicity data for developing the potential MG1-MAGEA3 oncolytic vaccine for human use. The use of the cynomolgous monkeys maximizes the likelihood of identifying responses that are quantitatively and qualitatively similar to those expected in humans. Prior to study start primates were acclimated for 4-6 weeks from the time of animal arrival until the time of vascular access port implantation surgery. After a minimum of 2-3 weeks following surgery, animals were vaccinated with a non-replicating adenovirus Ad-MAGEA3 priming vector, injected in each leg, 0.5 ml per dose totaling $1\times10^{10}$ pfu by slow IM injection. For the Ad-MAGEA3/MG1-MAGEA3 prime boost study, Ad-MAGEA3 prime occurred at either 2 weeks (−14 days) or 4 weeks (−28 days) prior to MG1-MAGEA3 boost. Therefore Ad-MAGEA3 administration occurred on Day −14 or on Day −28 and MG1-MAGEA3 boost on Days 0 and 3. The rationale for Ad-MAGEA3 dosage level comes from the literature, and from previous experiments demonstrating that a dose of $1\times10^{10}$ pfu in Macaques (and humans) is a safe dose with no observed toxicities (Bett et al. Vaccine, 2010). For animals in the 2 week boosted group, MG1-MAGEA3 virus was injected i.v. at either a low dose $1\times10^{10}$ or a high dose $1\times10^{11}$ at experiment days 0 and 3 (14 and 17 days after Ad-MAGEA3). For animals in the 4 week boosted group, MG1-MAGEA3 virus was injected i.v. at either a low dose $1\times10^{10}$ or a high dose $1\times10^{11}$ at experiment days 0 and 3, (28 and 31 days after the Ad-MAGEA3). Boosting Virus was infused in 30 mL of sterile buffered saline (pH 7.5) over 30 minutes through the vascular access port. The rationale for MG1-MAGEA3 low dosage level comes from pre-clinical studies that demonstrate that the murine maximum tolerable dose is $1\times10^9$. The relative body surface area scale-up to Macaques equates this to $3.5\times10^{10}$ total pfu. The rationale for MG1-MAGEA3 high dosage level comes from a pilot Non-Human Primate (NHP) toxicology study, where there was no observed toxicity at a dose level of $2\times10^{11}$ pfu. Animals in the prime boost study were either sacrificed early (Day 14) or late (Day 84). For the Ad-MAGEA3/MG1-MAGEA3 prime boost study, blood samples were taken from all animals at 5 distinct time points. For animals in the 2 week heterologous prime-boost cohort, blood samples were collected prior to any vaccination and on a day prior to Day −14 (Baseline) and on experiment Days 5, 13 and 84. For animals in the 4 week heterologous prime-boost cohort, blood samples were collected prior to any vaccination and on a day prior to Day −28 (Baseline), and on experiment Days 5, 13, and 84.

To assess immune responses in the primates to the heterologous prime-boost vaccination with Ad-MAGEA3/MG1-MAGEA3, Peripheral Blood Mononuclear Cells (PBMCs) were incubated for 4 hours (last 3 hours in presence of Brefeldin A) with a pool of 10 hMAGE-A3 peptides for T-cell (re-) stimulation (or left unstimulated for evaluation of the background). Peptides were from an overlapping peptide library covering the whole hMAGE-A3 antigen from N to C-termini in 87 peptides (15-mer each). After stimulation, T-cells were stained with fluorescent anti-CD8 and anti-CD4 antibodies for 25 minutes. After this surface staining, cells were permeabilized and fixed with BD Cytofix/Cytoperm for 20 minutes. Then, hMAGE-A3-specific T-cells were detected by looking at cytokine expression by intracellular staining with fluorescent anti-IFNγ and anti-TNFα antibodies for 25 minutes. Cell analysis was performed on BD Canto flow cytometer.

Figure 7:
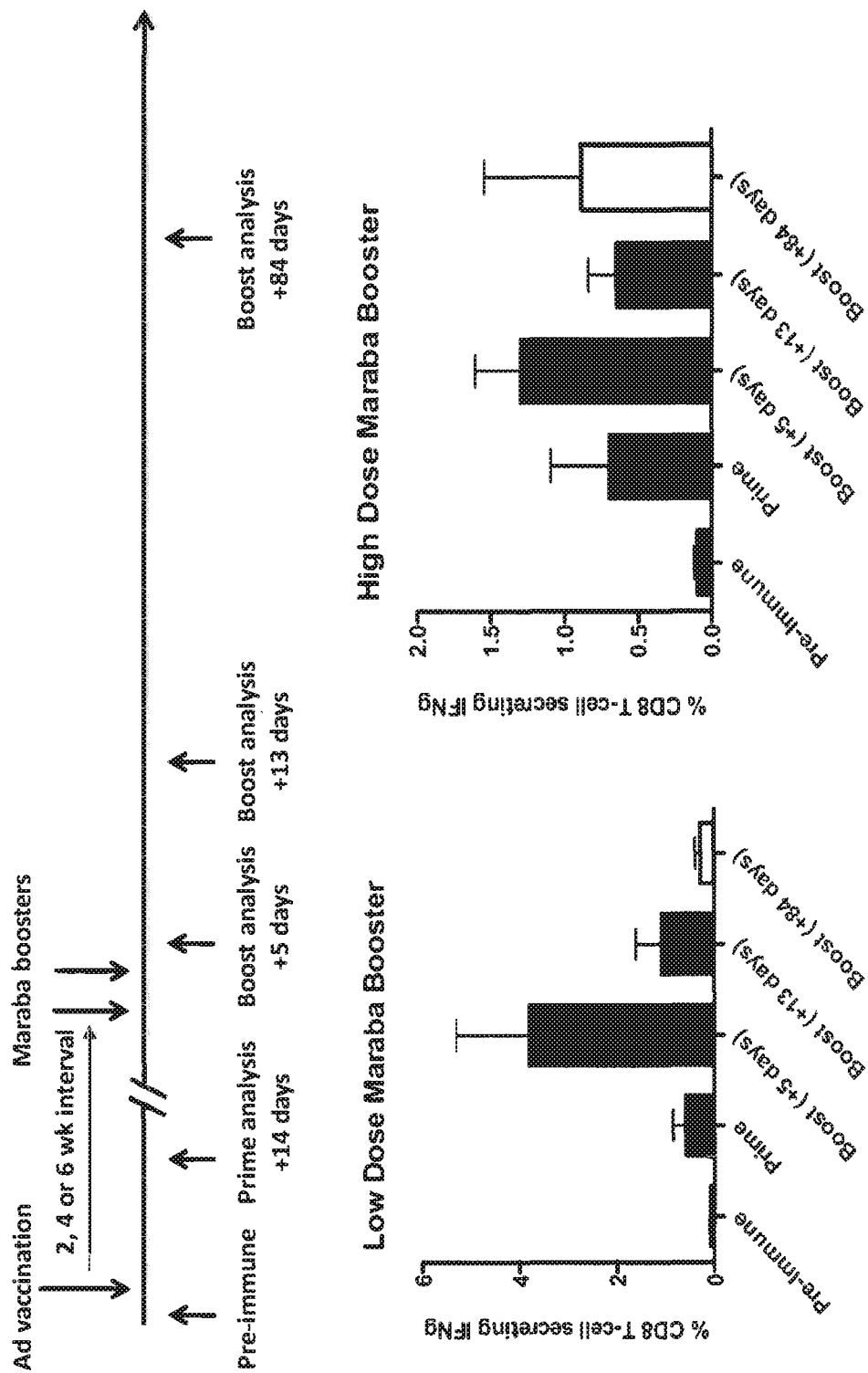
FIG. 7 shows the average T-cell response in primates given Ad-MAGEA3 as the priming vector and a high or low dose of MG1-MAGEA3 as the boosting vector. The T-cell responses were determined after 5, 13 and 84 days following the boosting vector.
Figure 8:
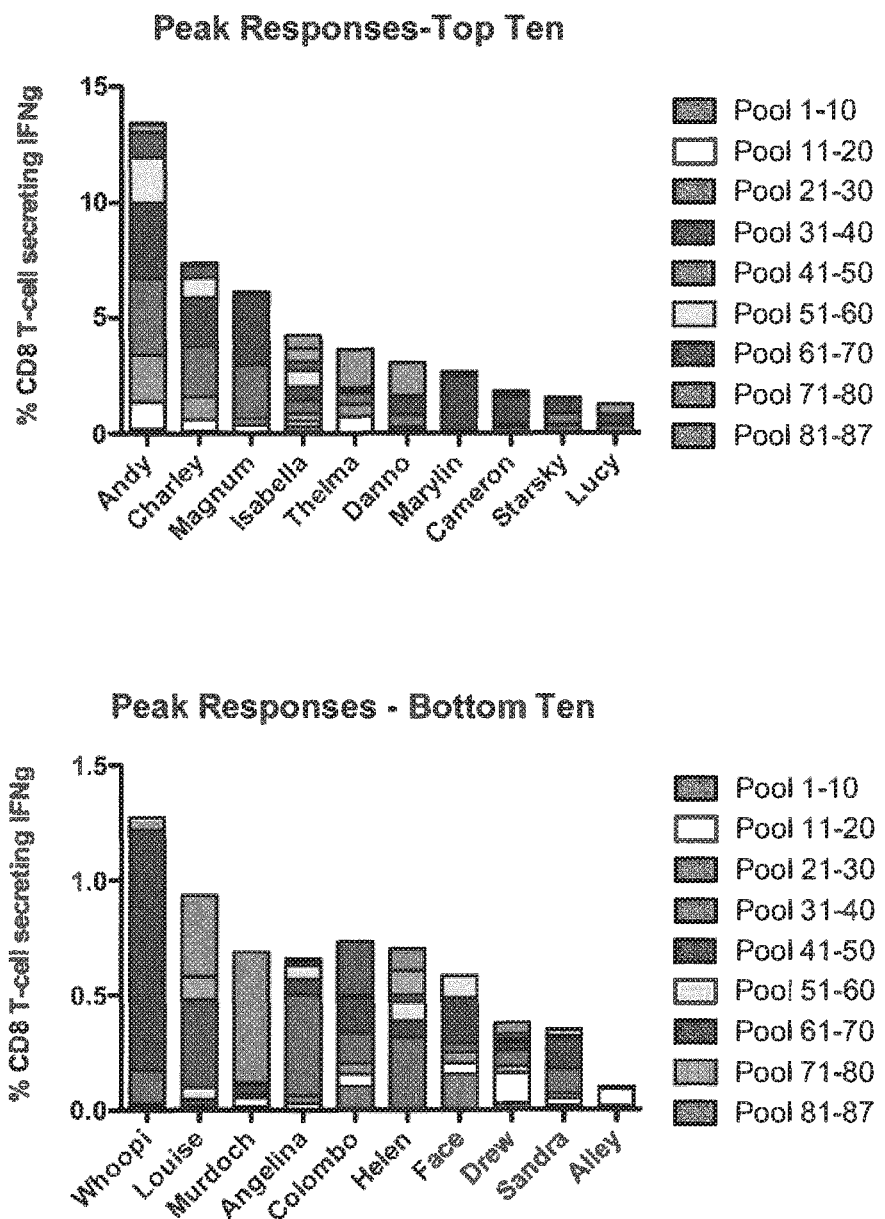
FIG. 8 shows the T-cell responses in individual primates given Ad-MAGEA3 as the priming vector and MG1-MAGEA3 as the boosting vector after 5 days following the boosting vector. The T-cell responses were stratified in relation to the MAGEA3 peptide pool used to stimulate the response.

FIG. 7 shows the average CD8$^+$ T-cell immune responses of monkeys given high and low dose MG1-MAGEA3 as a boosting vector following an Ad-MAGEA3 prime. In the low dose MG1-MAGEA3 animals there is a significant increase in CD8$^+$ T-cell response 5 days following the boost, which drops off over time while in the high dose MG1-MAGEA3 animals there is a similar significant increase in CD8$^+$ T-cell response 5 days following the boost, which is sustained at a higher level over time. FIG. 8 shows that all of the animals in the study exhibited a significant increase in CD8$^+$ T-cell response 5 days following the boost with MG1-MAGEA3 irrespective of high or low dose. These peak T-cell responses in Primates demonstrate that in an outbred population the prime-boost oncolytic vaccine strategy gives immune responses comparable to animal models where tumors can be engrafted and a dramatic extension of survival is attained.

Example 6: Construction and Immune Testing of Lentiviral Priming Vectors and Oncolytic Vaccine Vectors Expressing Human Papilloma Virus E6/E7 Fusion Protein The HPV transgene is a fusion of HPV serotype 16 full-length wild-type E6 (gi/4927720/gb/AAD33252.1/AF125673_1 E6 Human papillomavirus type 16) and E7 (gi/4927721/gb/AAD33253.1/AF125673_2 E7 Human papillomavirus type 16) sequences and HPV serotype 18 full-length wild-type E6 (gi/137758/sp/P06463.1/VE6_HPV18 RecName: Full=Protein E6) and E7 (gi/137792/sp/P06788.2/VE7 HPV18 RecName: Full=Protein E7) sequences with deletions in all 4 nucleotide sequences to remove zinc fingers required for Rb or p53 binding (removing oncogenic potential of the proteins). The resulting fusion protein has a flexible glycine linker plus AAY sequence (which serves as a proteasomal cleavage site to ensure that each antigen is proteolytically degraded to the peptides normally generated for antigen presentation). This codon-optimized fusion nucleotide sequence gives rise to a 527 amino acid HPV16/18 E6/E7 fusion protein (SEQ ID NO: 7).

Lentiviruses expressing Human Papilloma Virus E6/E7 fusion transgene were made using the pDY.EG.WS lentivirus vector. The modified HPV transgene was PCR amplified using primers containing the EcoRI restriction site (forward primer ACTGGAATTCATGCATCAGAAGCGAACTGC, SEQ ID NO: 18) and the BamHI restriction site (reverse primer ACTGGGATCCTCACTGCTGGGAGGCACAC, SEQ ID NO: 19). The HPV transgene PCR product was agarose gel purified. The pDY.EG.WS lentivirus vector was cut at the EcoRI and BamHI sites to remove eGFP, was agarose gel purified, and was subjected to dephosphorylation using CIAP (Invitrogen Catalogue 18009-019). The cut vector was then subjected to additional agarose gel purification. The HPV transgene PCR product was then ligated into the EcoRI/BamHI cut vector using T4 DNA ligase (Invitrogen). The ligation reaction was subjected to a transformation using competent cells, and plasmid DNA from positive colonies was subjected to mini-prep amplification. The pDY.EG.WS lentivirus vector expressing the modified HPV transgene was then subjected to maxi-prep amplification. The lentivirus expressing Human Papilloma Virus E6/E7 fusion transgene were rescued on 293T cells after transfection of 6.4 μg of each of three plasmids: the pDY.EG.WS lentivirus vector expressing the modified HPV transgene, the packaging pCMV-8.84 plasmid, and the envelope pMD2G plasmid. Virus supernatants were pooled, and filtered through a 0.45 μM filter and centrifuged for 120 minutes at 50,000×g at 16° C. The lentivirus expressing Human Papilloma Virus E6/E7 fusion transgene was resuspended in PBS, and stored at −80° C.

Maraba MG1 was engineered to contain a Papilloma Virus E6/E7 fusion transgene inserted between the G and L viral genes of the MG1 double mutant of Maraba virus (Brun J. et al., (2010) Mol Ther 18:1440-1449). The transgene sequence (SEQ ID NO: 8) was codon optimized for expression in mammalian cells. The resulting Maraba MG1 containing the HPV E6/E7 is designated, generally, "Maraba-MG1-HPV E6/E7". A modified Maraba MG1 backbone was used to facilitate cloning. A silent mutation was introduced into the L gene of the Maraba MG1 genome backbone to remove one of the MluI sites. The second MluI site was replaced with a BsiWI site at the cloning region between G and L. These modifications to the Maraba MG1 genome backbone allowed for a more direct cloning system than that described in the Brun et al. paper as it avoids using the shuttle plasmid pMRB-MG1/pNF. The HPV E6/E7 fused transgene sequence was ligated into the modified Maraba MG1 genome backbone at its MluI site and BsiWI site (at cloning region between G and L) The Maraba-MG1-HPV E6/E7 was then rescued (as previously described in Brun et al., (2010) Mol Ther 18:1440-1449), plaque purified once, and subjected to opti-prep purification.). The Maraba-MG1-HPV E6/E7 has a genomic sequence that is the reverse complement and RNA version of SEQ ID NO: 9.

Generally, animals were immunized by administration of the priming vector (lentivirus-HPV E6/E7+poly I:C as an adjuvant) at day 0 and by administration of 1e9 PFU of the boosting vector (Maraba-MG1-HPV E6/E7) at day 14. Control animals were prime-boosted with viral vectors encoding GFP instead of the HPV E6/E7 transgene as a control non-immunogenic transgene insertion. Analysis of the prime response was conducted at day 14 and of the boost response at day 19. Each lentivirus-HPVE6/E7 preparation was made with 250 ug poly I:C added as an adjuvant to the priming virus and then split between 5 animals for each virus. Mice were anesthetized with isoflurane and 30 uL of lentivirus-HPV E6/E7/poly I:C was injected into each hind foot pad. The remaining virus was injected subcutaneously near the left inguinal lymph node. 14 days after prime, blood was collected and analyzed by flow cytometry. Mice were then boosted with $1\times10^9$ PFU MG1-HPV E6/E7 intravenously. 5 days following the boost, blood was drawn and immune responses were assessed by flow cytometry.

Immune analysis was performed as follows: Blood was collected via retro-orbital bleeding using heparinzied capillary tube and blood was collected into heparin. Red blood cells were then lysed using ACK lysis buffer and the resulting PBMCs were analyzed for immune responses to the tumor antigens. PBMCs were either incubated in the absence of peptide or stimulated with 2 ug/mL peptides (RAHYNIVTF) (SEQ ID NO: 47) for a total of 5 hours with golgi plug added 1 hour into the stimulation. Following stimulation the PBMCs were stained for CD4, CD8 and IFNγ and analyzed on FACSCanto and FlowJo. Responding T-cells were detected after intracellular cytokine staining (ICS) for IFN-γ by flow cytometry. Values from unstimulated PBMCs were considered background and subtracted from values obtained from stimulated PBMCs. Data represents mean+/−SEM. In Table 1 it is demonstrated that the HPV E6/E7 peptides were able to stimulate IFN-γ production in CD8 cells indicating the existence of an immune response.

TABLE 1

IMMUNE RESPONSE to HPV E6/E7 PRIME-BOOST

| | Percentage of CD8 T Cells Secreting Interferon (IFN) γ | | | |
|---|---|---|---|---|
| Stimulatory Peptide Epitope | Control Group Lentivirus-GFP Prime MG1-GFP Boost | | Immune Group Lentivirus-HPV E6/E7 Prime MG1-HPV E6/E7 Boost (N = 5) | |
| RAHYNIVTF (SEQ ID NO: 47) | 0.0033 ± 0.0033 (after prime) | 0.03 ± 0.025 (after boost) | 0.036 ± 0.012 (after prime) | 5.9 ± 2.7 (after boost) |

Example 7: Construction and Immune Testing of Lentiviral Priming Vectors and Oncolytic Vaccine Vectors Expressing Cancer Testis Antigen 1

The NYESO1 transgene is full-length wild-type sequence (SEQ ID NO: 14) codon-optimized for expression in human and mouse to give rise to a 180 amino acid protein (SEQ ID NO: 13).

Lentiviruses expressing Cancer Testis Antigen 1 transgene were made using the pDY.EG.WS lentivirus vector. The NYESO1 transgene was PCR amplified using primers containing the BamHI restriction site (forward primer ACTGGGATCCATGCAGGCCGAGGGCAGAG, SEQ ID NO: 20) and the BamHI restriction site (reverse primer ACTGGGATCCTCATCTTCTCTGGCCGCTGG, SEQ ID NO: 21). The NYESO1 transgene PCR product was agarose gel purified. The pDY.EG.WS lentivirus vector was cut at the BamHI site to remove eGFP, was agarose gel purified, and was subjected to dephosphorylation using CIAP (Invitrogen Catalogue 18009-019). The cut vector was then subjected to additional agarose gel purification. The NYESO1 transgene PCR product was then ligated into the BamHI cut vector using T4 DNA ligase (Invitrogen). The ligation reaction was subjected to a transformation using competent cells, and plasmid DNA from positive colonies was subjected to mini-prep amplification. The pDY.EG.WS lentivirus vector expressing the modified HPV transgene was then subjected to maxi-prep amplification. The lentivirus expressing NYESO1 transgene were rescued on 293T cells after transfection of 6.4 µg of each of three plasmids: the pDY.EG.WS lentivirus vector expressing the NYESO1 transgene, the packaging pCMV-8.84 plasmid, and the envelope pMD2G plasmid. Virus supernatants were pooled, and filtered through a 0.45 µM filter and centrifuged for 120 minutes at 50,000×g at 16° C. The lentivirus expressing NYESO1 transgene was resuspended in PBS, and stored at −80° C.

Maraba MG1 was engineered to contain Cancer Testis Antigen 1 transgene inserted between the G and L viral genes of the MG1 double mutant of Maraba virus (Brun J. et al., (2010) Mol Ther 18:1440-1449). The transgene sequence was codon optimized for expression in mammalian cells. The resulting Maraba MG1 containing the NYESO1 protein is designated as "Maraba-MG1-NYESO1" or "MG1-NYESO1".

The NYESO1 transgene was ligated into the shuttle vector pMRB-MG1/pNF at its MluI site (between G and L genes) which contains part of the Maraba-MG1 genome from the beginning of G to the end of L genes, flanked by Kpnl and Nhel sites, respectively. The entire region from Kpnl to Nhel, now containing the NYESO1 transgene inserted between G and L was then removed from pMRB-MG1/pNF and ligated back into the pMRB-MG1 genomic plasmid using Kpnl and Nhel sites. The Maraba-MG1-NYESO1 was then rescued (as previously described Brun J. et al., (2010) Mol Ther 18: 1440-1449). The Maraba-MG1-NYESO1 was plaque purified 3 times, and purified via sucrose cushion purification. The Maraba-MG1-NYESO1 virus has a genomic sequence that is the reverse complement and RNA version of SEQ ID NO: 15.

Generally, animals were immunized by administration of the priming vector (lentivirus-NYESO1+poly I:C as an adjuvant) at day 0 and by administration of 1e9 PFU of the boosting vector (Maraba-MG1-NYESO1) at day 14. Control animals were prime-boosted with viral vectors encoding GFP instead of the NYESO1 transgene as a control non-immunogenic transgene insertion. Analysis of the prime response was conducted at day 14 and day 19. Each lentivirus-NYESO1 preparation was made with 250 ug poly I:C added as an adjuvant to the priming virus and then split between 5 animals for each virus. Mice were anesthetized with isoflurane and 30 uL of lentivirus-NYESO1/poly I:C was injected into each hind foot pad. The remaining virus was injected subcutaneously near the left inguinal lymph node. 14 days after prime, blood was collected and analyzed by flow cytometry. Mice were then boosted with 1×10⁹ PFU MG1-NYESO1 intravenously. Five days following the boost, blood was drawn and immune responses were assessed by flow cytometry.

Immune analysis was performed as follows: Blood was collected via retro-orbital bleeding using heparinzied capillary tube and blood was collected into heparin. Red blood cells were then lysed using ACK lysis buffer and the resulting PBMCs were analyzed for immune responses to the tumor antigens. PBMCs were either incubated in the absence of peptide or stimulated with 2 ug/mL peptides (RGPESRLL) (SEQ ID NO: 48) for a total of 5 hours with golgi plug added 1 hour into the stimulation. Following stimulation the PBMCs were stained for CD4, CD8 and IFNγ and analyzed on FACSCanto and FlowJo. Responding T-cells were detected after intracellular cytokine staining (ICS) for IFN-γ by flow cytometry. Values from unstimulated PBMCs were considered background and subtracted from values obtained from stimulated PBMCs. Data represents mean+/−SEM. In Table 2 it is demonstrated that the NYESO1 peptides were able to stimulate IFN-γ production in CD8 cells indicating the existence of an immune response.

TABLE 2

| | IMMUNE RESPONSE to NYESO1 PRIME-BOOST | | | |
|---|---|---|---|---|
| | Percentage of CD8 T Cells Secreting Interferon (IFN) γ | | | |
| | Control Group Lentivirus-GFP Prime MG1-GFP Boost | | Immune Group Lentivirus-NYESO1 Prime MG1-NYESO1 Boost (N = 5) | |
| Stimulatory Peptide Epitope | | | | |
| RGPESRLL (SEQ ID NO: 48) | 0 ± 0 (after prime) | 0.013 ± 0.0088 (after boost) | 0.027 ± 0.015 (after prime) | 12.33 (after boost) |

Example 8: Construction and Immune Testing of Lentiviral Priming Vectors and Oncolytic Vaccine Vectors Expressing Human Six-Transmembrane Epithelial Antigen of the Prostate Protein The huSTEAP transgene is full-length wild-type sequence (SEQ ID NO: 11) codon-optimized for expression in human and mouse to give rise to a 341 amino acid protein (SEQ ID NO: 10).

Lentiviruses expressing human Six-Transmembrane Epithelial Antigen of the Prostate protein were made using the pDY.EG.WS lentivirus vector. The huSTEAP transgene was PCR amplified using primers containing the EcoRI restriction site (forward primer ACTGGAATTCATGGAAT-CACGGAAGGACATC, SEQ ID NO: 22) and the BamHI restriction site (reverse primer ACTGGGATCCT-TAAAGCTTCAGCTGGCTACAG, SEQ ID NO: 23). The huSTEAP transgene PCR product was agarose gel purified. The pDY.EG.WS lentivirus vector was cut at the EcoRI/BamHI site to remove eGFP, was agarose gel purified, and was subjected to dephosphorylation using CIAP (Invitrogen Catalogue 18009-019). The cut vector was then subjected to additional agarose gel purification. The huSTEAP transgene PCR product was then ligated into the EcoRI/BamHI cut vector using T4 DNA ligase (Invitrogen). The ligation reaction was subjected to a transformation using competent cells, and plasmid DNA from positive colonies was subjected to mini-prep amplification. The pDY.EG.WS lentivirus vector expressing the modified huSTEAP transgene was then subjected to maxi-prep amplification. The lentivirus expressing huSTEAP transgene were rescued on 293T cells after transfection of 6.4 µg of each of three plasmids: the pDY.EG.WS lentivirus vector expressing the huSTEAP transgene, the packaging pCMV-8.84 plasmid, and the envelope pMD2G plasmid. Virus supernatants were pooled, and filtered through a 0.45 µM filter and centrifuged for 120 minutes at 50,000×g at 16° C. The lentivirus expressing huSTEAP transgene was resuspended in PBS, and stored at −80° C.

Maraba MG1 was engineered to contain human Six-Transmembrane Epithelial Antigen of the Prostate transgene inserted between the G and L viral genes of the MG1 double mutant of Maraba virus (Brun J. et al., (2010) Mol Ther 18:1440-1449). The transgene sequence was codon optimized for expression in mammalian cells. The resulting Maraba MG1 containing the huSTEAP protein is designated as "Maraba-MG1-huSTEAP" or "MG1-huSTEAP". A modified Maraba MG1 backbone was used to facilitate cloning. A silent mutation was introduced into the L gene of the Maraba MG1 genome backbone to remove one of the Mlul sites. The second Mlul site was replaced with a BsiWI site at the cloning region between G and L. These modifications to the Maraba MG1 genome backbone allowed for a more direct cloning system than that described in the Brun et al. paper as it avoids using the shuttle plasmid pMRB-MG1/pNF. The huSTEAP transgene sequence was ligated into the modified Maraba MG1 genome backbone at its Mlul and BsiWI site (at cloning region between G and L). The Maraba-MG1-huSTEAP was then rescued (as previously described in Brun J. et al., (2010) Mol Ther 18:1440-1449), plaque purified once, and subjected to opti-prep purification. The Maraba-MG1-huSTEAP has a genomic sequence that is the reverse complement and RNA version of SEQ ID NO: 12.

Generally, animals were immunized by administration of the priming vector (lentivirus-huSTEAP+poly I:C as an adjuvant) at day 0 and by administration of 1e9 PFU of the boosting vector (Maraba-MG1-huSTEAP) at day 14. Control animals were prime-boosted with viral vectors encoding GFP instead of the huSTEAP transgene as a control non-immunogenic transgene insertion. Analysis of the prime response was conducted at day 14 and day 19. Each lentivirus-huSTEAP preparation was made with 250 ug poly I:C added as an adjuvant to the priming virus and then split between 5 animals for each virus. Mice were anesthetized with isoflurane and 30 uL of lentivirus-huSTEAP/poly I:C was injected into each hind foot pad. The remaining virus was injected subcutaneously near the left inguinal lymph node. 14 days after prime, blood was collected and analyzed by flow cytometry. Mice were then boosted with $1 \times 10^9$ PFU MG1-huSTEAP intravenously. Five days following the boost, blood was drawn and immune responses were assessed by flow cytometry.

Immune analysis was performed as follows: Blood was collected via retro-orbital bleeding using heparinzied capillary tube and blood was collected into heparin. Red blood cells were then lysed using ACK lysis buffer and the resulting PBMCs were analyzed for immune responses to the tumor antigens. PBMCs were either incubated in the absence of peptide or stimulated with peptides for a total of 5 hours with golgi plug added 1 hour into the stimulation. PBMCs were either incubated in the absence of peptide or stimulated with 2 ug/mL peptides (RSRYKLL) (SEQ ID NO: 49) for a total of 5 hours with golgi plug added 1 hour into the stimulation. Following stimulation the PBMCs were stained for CD4, CD8 and IFNγ and analyzed on FACSCanto and FlowJo. Responding T-cells were detected after intracellular cytokine staining (ICS) for IFN-γ by flow cytometry. Values from unstimulated PBMCs were considered background and subtracted from values obtained from stimulated PBMCs. Data 20 represents mean+/−SEM. In Table 3 it is demonstrated that the huSTEAP peptides were able to stimulate IFN-γ production in CD8 cells indicating the existence of an immune response.

TABLE 3

IMMUNE RESPONSE to huSTEAP PRIME-BOOST

| | Percentage of CD8 T Cells Secreting Interferon (IFN) γ | | | |
|---|---|---|---|---|
| | Control Group Lentivirus-GFP Prime MG1-GFP Boost | | Immune Group Lentivirus-huSTEAP Prime MG1- huSTEAP Boost (N = 5) | |
| Stimulatory Peptide Epitope | (after prime) | (after boost) | (after prime) | (after boost) |
| RSYRYKLL (SEQ ID NO: 49) | 0.0033 ± 0.0033 | 0.0033 ± 0.0033 | 0.008 ± 0.0508 | 0.0406 ± 0.11 |

Example 9: Construction and Immune Testing of Lentiviral Priming Vectors and Oncolytic Vaccine Vectors Expressing Epstein-Barr Nuclear Antigen 1

The EBDNA1 transgene is a partial nucleotide sequence of full-length wild-type EBDNA1 (www.ncbi.nlm.nih.gov/protein/Q1HVF7.1) with the Glycine-Alanine generating repetitive sequence deleted (which separates the protein into amino- and carboxy-terminal domains). This sequence seems to stabilize the protein, preventing proteasomal breakdown, as well as impairing antigen processing and MHC class I-restricted antigen presentation (Levitskaya J et al., (1995) Nature 375:685-688). The truncated EBDNA1 nucleotide sequence (SEQ ID NO: 17) was codon-optimized for expression in human and mouse to give rise to a 238 amino acid protein (SEQ ID NO: 16).

Lentiviruses expressing Epstein-Barr Nuclear Antigen 1 protein were made using the pDY.EG.WS lentivirus vector. The modified EBDNA1 transgene was PCR amplified using primers containing the EcoRI restriction site (forward primer ACTGGAATTCATGCCAGTCGGCCAGGCTG, SEQ ID NO: 24) and the BamHI restriction site (reverse primer ACTGGGATCCTTATTCCTGCCCCTCTTCTCC, SEQ ID NO: 25). The EBDNA1 transgene PCR product was agarose gel purified. The pDY.EG.WS lentivirus vector was cut at the EcoRI and BamHI sites to remove eGFP, was agarose gel purified, and was subjected to dephosphorylation using CIAP (Invitrogen Catalogue 18009-019). The cut vector was then subjected to additional agarose gel purification. The EBDNA1 transgene PCR product was then ligated into the EcoRI/BamHI cut vector using T4 DNA ligase (Invitrogen). The ligation reaction was subjected to a transformation using competent cells, and plasmid DNA from positive colonies was subjected to mini-prep amplification. The pDY.EG.WS lentivirus vector expressing the EBDNA1 transgene was then subjected to maxi-prep amplification. The lentivirus expressing EBDNA1 transgene was rescued on 293T cells after transfection of 6.4 µg of each of three plasmids: the pDY.EG.WS lentivirus vector expressing the EBDNA1 transgene, the packaging pCMV-8.84 plasmid, and the envelope pMD2G plasmid. Virus supernatants were pooled, and filtered through a 0.45 µM filter and centrifuged for 120 minutes at 50,000×g at 16° C. The lentivirus expressing EBDNA1 transgene was resuspended in PBS, and stored at −80° C.

Maraba MG1 was engineered to contain Epstein-Barr Nuclear Antigen 1 transgene inserted between the G and L viral genes of the MG1 double mutant of Maraba virus (Brun J. et al., (2010) Mol Ther 18: 1440-1449). The transgene sequence was codon optimized for expression in mammalian cells. The resulting Maraba MG1 containing the EBVDNA1 protein is designated as "Maraba-MG1-EBVDNA1" or "MG1-EDVDNA1". A modified Maraba MG1 backbone was used to facilitate cloning. A silent mutation was introduced into the L gene of the Maraba MG1 genome backbone to remove one of the MluI sites. The second MluI site was replaced with a BsiWI site at the cloning region between G and L. These modifications to the Maraba MG1 genome backbone allowed for a more direct cloning system than that described in the Brun et al. paper as it avoids using the shuttle plasmid pMRB-MG1/pNF. The EBDNA1 transgene sequence was ligated into the modified Maraba MG1 genome backbone at its MluI and BsiWI site (at cloning region between G and L). The Maraba-MG1-EBDNA1 transgene was then rescued (as previously described in Brun J. et al., (2010) Mol Ther 18:1440-1449), plaque purified once, and subjected to opti-prep purification.

Generally, animals were immunized by administration of the priming vector (lentivirus-EBDNA1+poly I:C as an adjuvant) at day 0 and by administration of 1e9 PFU of the boosting vector (Maraba-MG1-EBDNA1) at day 14. Control animals were prime-boosted with viral vectors encoding GFP instead of the TM transgene as a control non-immunogenic transgene insertion. Analysis of the prime response was conducted at day 14 and day 19. Each lentivirus-EBDNA1 preparation was made with 250 ug poly I:C added as an adjuvant to the priming virus and then split between 5 animals for each virus. Mice were anesthetized with isoflurane and 30 uL of lentivirus-EBDNA1/poly I:C was injected into each hind foot pad. The remaining virus was injected subcutaneously near the left inguinal lymph node. 14 days after prime, blood was collected and analyzed by flow cytometry. Mice were then boosted with 1×10$^9$ PFU MG1-EBDNA1 intravenously. Five days following the boost, blood was drawn and immune responses were assessed by flow cytometry.

Immune analysis was performed as follows: Blood was collected via retro-orbital bleeding using heparinzied capillary tube and blood was collected into heparin. Red blood cells were then lysed using ACK lysis buffer and the resulting PBMCs were analyzed for immune responses to the tumor antigens. PBMCs were either incubated in the absence of peptide or stimulated with 2 ug/mL peptides (VYGGSKTSL) (SEQ ID NO: 50) for a total of 5 hours with golgi 30 plug added 1 hour into the stimulation. Following stimulation the PBMCs were stained for CD4, CD8 and IFNγ and analyzed on FACSCanto and FlowJo. Responding T-cells were detected after intracellular cytokine staining (ICS) for IFN-γ by flow cytometry. Values from unstimulated PBMCs were considered background and subtracted from values obtained from stimulated PBMCs. Data represents mean+/−SEM. The EBVDNA1 peptides were unable to stimulate IFN-γ production in either CD8 T cells indicating a lack of an immune response, as shown in Table 4.

TABLE 4

IMMUNE RESPONSE to EBVDNA1 PRIME-BOOST

| | Percentage of CD8 T Cells Secreting Interferon (IFN) γ | |
|---|---|---|
| | Control Group | Immune Group |
| | Lentivirus-GFP Prime | Lentivirus- EBVDNA1Prime |
| Stimulatory Peptide Epitope | MG1-GFP Boost | MG1- EBVDNA1 Boost (N = 5) |
| VYGGSKTSL (SEQ ID NO: 50) | 0.055 ± 0.015 (after prime)  0.01 ± 0.0058 (after boost) | 0.008 ± 0.0049 (after prime)  0.09 ± 0.05 (after boost) |

Example 10: Effect of Cyclophosphamide on Adenovirus-OV Vaccine Prime-Boost Strategy Cyclophosphamide (CPA) is a chemotherapeutic agent used to treat various types of cancer. High doses of this drug are required for effective chemotherapy. High doses of CPA are thought to lead to immunosuppression while low doses of the drug can lead to enhanced immune responses against a variety of antigens. Surprisingly, in the heterologous prime-boost strategy of the current disclosure, CPA only results in an increase in immune response when administered prior to the priming of the immune system by the first virus.

Figure 9:
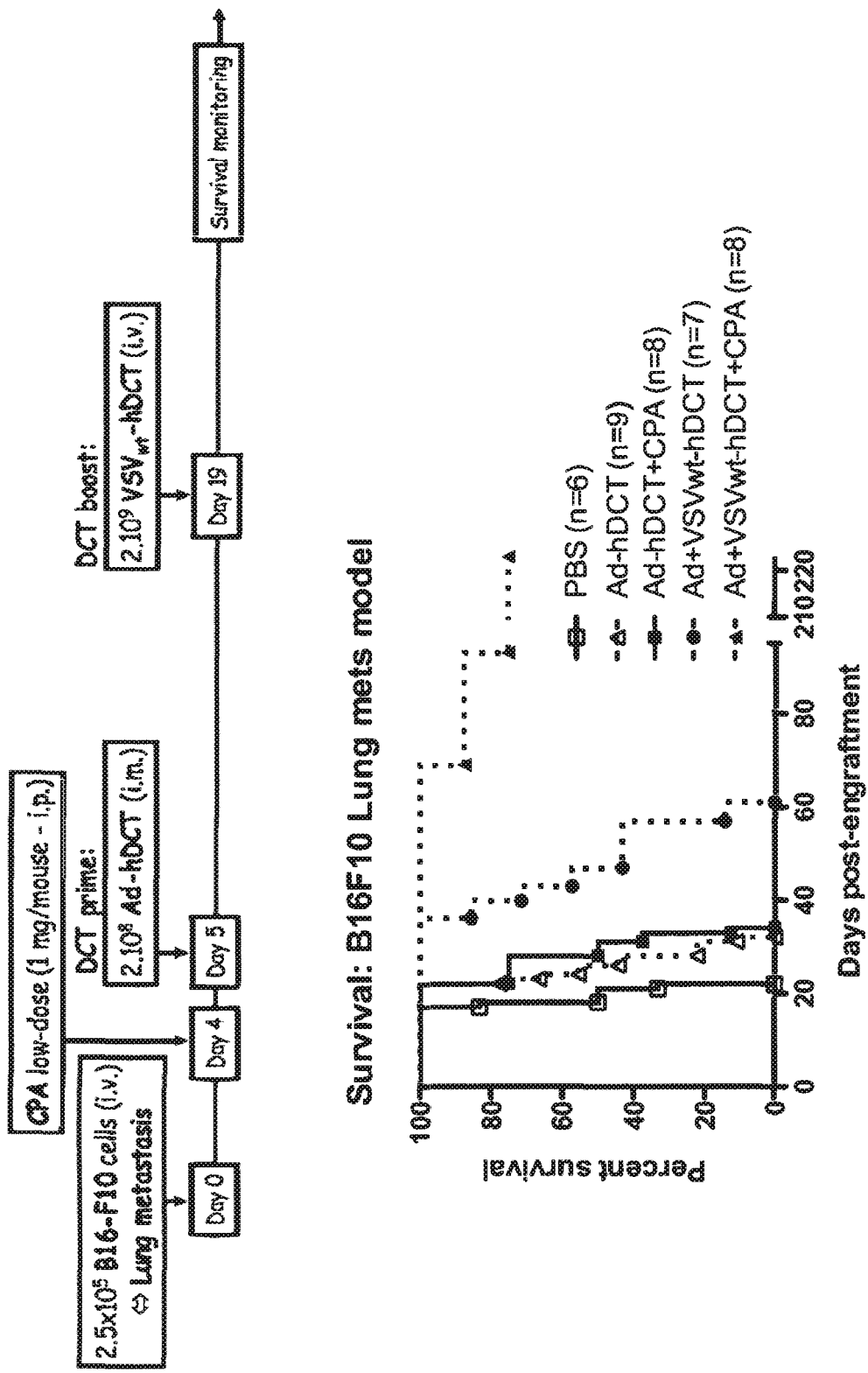
FIG. 9 shows the survival plot in a metastatic lung cancer mouse model following Ad-hDCT versus Ad-hDCT plus Cyclophosphamide, as the priming vector only or following prime-boost vaccination with Ad-hDCT versus Ad-hDCT plus Cyclophosphamide, as the priming vector and VSV-hDCT, as the boosting vector.

In order to generate lung metastases, C57Bl/6 mice (8-10 weeks old at study initiation) were injected with 2.5×10$^5$ B16-F10 cells (murine melanoma cells expressing the murine DCT antigen) in 200 µl saline water i.v. at day 0. Five days following B16-F10 engraftment, mice received an Ad-hDCT priming vaccine (2×10$^8$ pfu in 200 µl PBS i.m.) and this was followed 14 days later by a single i.v. dose of VSV-hDCT (2×10$^9$ pfu in 200 µl PBS i.v.) as an oncolytic booster vaccine. Additionally, mice either received vehicle or CPA (1 mg/20 g mouse, i.p.) at day (−1) prior to the prime and/or day 13 prior to the boost. In FIG. 9 it can be seen that CPA given prior to the priming vector significantly increases survival while CPA administered prior to the boosting vector does not extend survival (data not shown).

In the preceding description, for purposes of explanation, numerous details are set forth in order to provide a thorough understanding of the examples. The above-described examples are intended to be exemplary only. Alterations, modifications and variations can be effected to the particular examples by those of skill in the art without departing from the scope, which is defined solely by the claims appended hereto.

APPENDIX A

Protein and Nucleotide Sequences

Protein sequence of full length, wild type, human MAGEA3 (SEQ ID NO: 1):
MPLEQRSQHCKPEEGLEARGEALGLVGAQAPATEEQEAASSSSTLVEVTLGEVPAAESP
DPPQSPQGASSLPTTMNYPLWSQSYEDSSNQEEEGPSTFPDLESEFQAALSRKVAELVHF
LLLKYRAREPVTKAEMLGSVVGNWQYFFPVIFSKASSSLQLVFGIELMEVDPIGHLYIFA
TCLGLSYDGLLGDNQIMPKAGLLIIVLAIIAREGDCAPEEKIWEELSVLEVFEGREDSILG
DPKKLLTQHFVQENYLEYRQVPGSDPACYEFLWGPRALVETSYVKVLHHMVKISGGPH
ISYPPLHEWVLREGEE*

DNA sequence encoding full length, wild type, human MA GEA3 (SEQ ID NO: 2):
ATGCCTCTTGAGCAGAGGAGTCAGCACTGCAAGCCTGAAGAAGGCCTTGAGGCCCG
AGGAGAGGCCCTGGGCCTGGTGGGTGCGCAGGCTCCTGCTACTGAGGAGCAGGAGG
CTGCCTCCTCCTCTTCTACTCTAGTTGAAGTCACCCTGGGGGAGGTGCCTGCTGCCG
AGTCACCAGATCCTCCCCAGAGTCCTCAGGGAGCCTCCAGCCTCCCCACTACCATGA
ACTACCCTCTCTGGAGCCAATCCTATGAGGACTCCAGCAACCAAGAAGAGGAGGGG
CCAAGCACCTTCCCTGACCTGGAGTCCGAGTTCCAAGCAGCACTCAGTAGGAAGGT
GGCCGAGTTGGTTCATTTTCTGCTCCTCAAGTATCGAGCCAGGGAGCCGGTCACAAA
GGCAGAAATGCTGGGGAGTGTCGTCGGAAATTGGCAGTATTTCTTTCCTGTGATCTT
CAGCAAAGCTTCCAGTTCCTTGCAGCTGGTCTTTGGCATCGAGCTGATGGAAGTGGA
CCCCATCGGCCACTTGTACATCTTTGCCACCTGCCTGGGCCTCTCCTACGATGGCCTG
CTGGGTGACAATCAGATCATGCCCAAGGCAGGCCTCCTGATAATCGTCCTGGCCATA
ATCGCAAGAGAGGGCGACTGTGCCCCTGAGGAGAAAATCTGGGAGGAGCTGAGTGT
GTTAGAGGTGTTTGAGGGGAGGGAAGACAGTATCTTGGGGGATCCCAAGAAGCTGC
TCACCCAACATTTCGTGCAGGAAAACTACCTGGAGTACCGGCAGGTCCCCGGCAGT
GATCCTGCATGTTATGAATTCCTGTGGGGTCCAAGGGCCCTCGTTGAAACCAGCTAT
GTGAAAGTCCTGCACCATATGGTAAAGATCAGTGGAGGACCTCACATTTCCTACCCA
CCCCTGCATGAGTGGGTTTTGAGAGAGGGGGAAGAGTGA Codon optimized DNA sequence encoding full length, wild type, human MA GEA3 protein (SEQ ID NO: 3):
ATGCCCCTGGAGCAGCGGTCTCAGCATTGCAAGCCAGAGGAGGGCCTCGAGGCGAG
GGGCGAGGCCCTCGGCTTGGTGGGGCGCAGGCTCCTGCAACCGAGGAGCAAGAGG
CCGCATCCAGTTCCTCTACCCTGGTTGAGGTGACCTTGGGTGAGGTGCCCGCCGCGG
AGAGCCCCGACCCGCCTCAAAGCCCCCAGGGTGCCAGCTCCCTGCCCACAACAATG
AACTACCCACTCTGGAGTCAGTCTTACGAGGACAGTAGTAACCAAGAGGAGGAGGG
ACCCTCCACATTCCCAGACCTGGAGTCTGAATTCCAGGCAGCATTGTCTAGAAAAGT
GGCCGAATTGGTGCACTTCCTGCTGCTGAAGTATCGCGCCCGCGAGCCAGTCACAAA
AGCTGAAATGCTGGGTTCTGTCGTGGGAAATTGGCAGTACTTCTTCCCCGTGATCTT
CAGTAAAGCGTCCAGCTCCTTGCAGCTGGTCTTTGGTATCGAGCTGATGGAGGTGGA
TCCCATCGGCCATCTGTATATCTTTGCCACATGCCTGGGCCTGAGCTACGATGGCCT
GCTGGGCGACAACCAGATCATGCCAAAAGCTGGCCTGCTGATCATCGTTCTGGCTAT
CATCGCTAGAGAAGGAGATTGCGCCCCTGAAGAAAGATCTGGGAGGAACTGAGCG
TCCTGGAAGTCTTTGAGGGTCGTGAAGACAGCATTCTCGGGGATCCCAAGAAGCTGC
TGACCCAGCACTTCGTGCAGGAGAACTATCTGGAGTACCGCCAGGTTCCCGGCAGC
GACCCCGCTTGCTACGAGTTCCTGTGGGGCCCCAGGGCCCTGGTCGAGACATCCTAC
GTGAAGGTCCTGCACCATATGGTTAAAATCAGCGGCGGCCCCCATATCTCTTATCCG
CCGCTCCACGAGTGGGTGCTCCGGGAGGGAGAGGAG Protein sequence of a variant of full length, wild type, human MAGEA3 (SEQ ID NO: 4):
MPLEQRSQHCKPEEGLEARGEALGLVGAQAPATEEQEAASSSSTLVEVTLGEVPAAESP
DPPQSPQGASSLPTTMNYPLWSQSYEDSSNQEEEGPSTFPDLESEFQAALSRKVAELVHF
LLLKYRAREPVTKAEMLGSVVGNWQYFFPVIFSKASSSLQLVFGIELMEVDPIGHLYIFA
TCLGLSYDGLLGDNQIMPKAGLLIIVLAIIAREGDCAPEEKIWEELSVLEVFEGREDSILG
DPKKLLTQHFVQENYLEYRQVPGSDPACYEFLWGPRALVETSYVKVLHHMVKISGGPH
ISYPPLHEWVLREGEEDYKDDDDK*

DNA sequence encoding a variant of full length, wild type, human MAGEA3 (SEQ ID NO: 5):
ATGCCCCTGGAACAGCGGAGCCAGCACTGCAAGCCCGAGGAAGGCCTGGAAGCCA
GAGGCGAAGCCCTGGGACTGGTGGGAGCCCAGGCCCCTGCCACAGAAGAACAGGA
AGCCGCCAGCAGCAGCTCCACCCTGGTGGAAGTGACCCTGGGCGAAGTGCCTGCCG
CCGAGAGCCCTGATCCCCCTCAGTCTCCTCAGGGCGCCAGCAGCCTGCCCACCACCA
TGAACTACCCCCTGTGGTCCCAGAGCTACGAGGACAGCAGCAACCAGGAAGAGGAA
GGCCCCAGCACCTTCCCCGACCTGGAAAGCGAGTTCCAGGCCGCCCTGAGCCGGAA
GGTGGCAGAGCTGGTGCACTTCCTGCTGCTGAAGTACAGAGCCCGCGAGCCCGTGA
CCAAGGCCGAGATGCTGGGCAGCGTGGTGGGAAACTGGCAGTACTTCTTCCCCGTG
ATCTTCTCCAAGGCCAGCAGCTCCCTGCAGCTGGTGTTCGGCATCGAGCTGATGGAA
GTGGACCCCATCGGCCACCTGTACATCTTCGCCACCTGTCTGGGCCTGAGCTACGAC
GGCCTGCTGGGCGACAACCAGATCATGCCCAAGGCCGGCCTGCTGATCATCGTGCT
GGCCATCATTGCCCGCGAGGGCGACTGCGCCCCTGAGGAAAAGATCTGGGAGGAAC
TGAGCGTGCTGGAAGTGTTCGAGGGCAGAGAGGACAGCATCCTGGGCGACCCCAAG
AAGCTGCTGACCCAGCACTTCGTGCAGGAAAACTACCTGGAATACCGCCAGGTGCC
CGGCAGCGACCCCGCTTGTTACGAGTTCCTGTGGGGCCCCAGGGCTCTGGTGGAAA
CCAGCTACGTGAAGGTGCTGCACCACATGGTGAAAATCAGCGGCGGACCCCACATC
AGCTACCCCCCACTGCACGAGTGGGTGCTGAGAGAGGGCGAAGAGGACTACAAGG
ACGACGACGACAAATGA APPENDIX A-continued Protein and Nucleotide Sequences Protein sequence of HPV E6/E7 fusion protein (SEQ ID NO: 7):
MHQKRTAMFQDPQERPRKLPQLCTELQTTIHDIILECVYCKQQLLRREVYDFAFRDLCIV
YRDGNPYAVDKLKFYSKISEYRHYCYSVYGTTLEQQYNKPLCDLLIRINQKPLCPEEKQ
RHLDKKQRFHNIRGRWTGRCMSCCRSSRTRRETQLGGGGGAAYMARFEDPTRRPYKLP
DLCTELNTSLQDIEITCVYCKTVLELTEVFEFAFKDLFVVYRDSIPHAAHKIDFYSRIRELR
HYSDSVYGDTLEKLTNTGLYNLLIRLRQKPLNPAEKLRHLNEKRRFHNIAGHYRGQCHS
CCNRARQERLQRRRETQVGGGGGAAYMHGDTPTLHEYMLDLQPETTDLYQLNDSSEE
EDEIDGPAGQAEPDRAHYNIVTFCCKCDSTLRLCVQSTHVD1RTLEDLLMGTLGIVPICSQ
KPGGGGGAAYMHGPKATLQDIVLHLEPQNEIPVDLLQLSDSEEENDEIDGVNHQHLPAR
RAEPQRHTMLCMCCKCEARIKLVVESSADDLRAFQQLFLNTLSFVPWCASQQ*

DNA sequence of HPV E6/E7 fusion protein (SEQ ID NO: 8):
ATGCATCAGAAGCGAACTGCTATGTTTCAGGACCCTCAGGAGCGGCCACGCAAACT
GCCTCAGCTGTGCACCGAACTGCAGACAACTATCCACGACATCATTCTGGAATGCGT
GTACTGTAAGCAGCAGCTGCTGAGGAGAGAGGTCTATGACTTCGCTTTTCGCGATCT
GTGCATCGTGTACCGAGACGGAAACCCATATGCAGTCGATAAGCTGAAGTTCTACA
GCAAGATCTCCGAATACAGGCATTACTGTTACAGCGTGTACGGGACCACACTGGAG
CAGCAGTATAACAAGCCCCTGTGCGACCTGCTGATCAGAATTAATCAGAAGCCCCT
GTGCCCTGAGGAAAAACAGAGGCACCTGGATAAGAAACAGAGATTTCATAACATCC
GAGGACGATGGACCGGGCGGTGCATGTCCTGCTGTAGAAGCTCCCGGACTCGACGA
GAGACCCAGCTGGGCGGAGGAGGAGGAGCAGCTTACATGGCACGATTCGAGGACC
CTACCCGAAGGCCATATAAGCTGCCCGACCTGTGCACAGAACTGAATACTTCTCTGC
AGGACATCGAGATTACATGCGTGTACTGTAAAACCGTCCTGGAGCTGACAGAAGTG
TTCGAGTTTGCTTTCAAGGACCTGTTTGTGGTCTACCGGGATTCAATCCCTCACGCAG
CCCATAAAATCGACTTCTACAGCAGGATCAGGGAACTGCGCCACTACTCCGACAGC
GTGTACGGGGATACACTGGAGAAGCTGACAAACACTGGCCTGTACAATCTGCTGAT
CCGACTGCGACAGAAGCCACTGAACCCAGCCGAAAAACTGAGACACCTGAACGAG
AAGAGACGGTTTCACAATATTGCAGGCCATTATAGGGGACAGTGCCATAGTTGCTGT
AATCGAGCCAGGCAGGAAAGACTGCAGCGCCGAAGGGAGACTCAAGTCGGCGGAG
GAGGAGGAGCTGCATACATGCACGGCGACACCCCCACACTGCATGAATATATGCTG
GATCTGCAGCCTGAGACTACCGACCTGTACCAGCTGAACGATTCTAGTGAGGAAGA
GGACGAAATCGACGGACCAGCAGGACAGGCAGAGCCTGACCGGGCCCACTATAAT
ATTGTGACATTCTGCTGTAAGTGCGATTCTACTCTGCGGCTGTGCGTGCAGAGTACT
CATGTCGACATCCGCACCCTGGAGGATCTGCTGATGGGGACTCTGGGCATCGTCCCA
ATTTGTAGCCAGAAACCAGGCGGCGGCGGCGAGCAGCTTACATGCACGGACCCAA
GGCTACCCTGCAGGACATCGTGCTGCATCTGGAACCTCAGAATGAGATTCCAGTCGA
CCTGCTGCAGCTGAGTGATTCAGAAGAGGAAAACGACGAGATCGACGGCGTGAATC
ACCAGCATCTGCCTGCTAGACGGGCAGAGCCACAGCGACACACAATGCTGTGCATG
TGCTGTAAGTGTGAAGCCAGGATCAAGCTGGTGGTCGAGTCAAGCGCCGACGATCT
GCGCGCCTTCCAGCAGCTGTTCCTGAATACTCTGTCATTTGTCCCTTGGTGTGCCTCC
CAGCAGTGA Protein sequence of huSTEAP protein (SEQ ID NO: 10):
MESRKDITNQEELWKMKPRRNLEEDDYLHKDTGETSMLKRPVLLHLHQTAHADEFDCP
SELQHTQELFPQWHLPIKIAAIIASLTFLYTLLREVIHPLATSHQQYFYKIPILVINKVLPMV
SITLLALVYLPGVIAAIVQLHNGTKYKKFPHWLDKWMLTRKQFGLLSFFFAVLHAIYSLS
YPMRRSYRYKLLNWAYQQVQQNKEDAWIEHDVWRMEIYVSLGIVGLAILALLAVTSIP
SVSDSLTWREFHYIQSKLGIVSLLLGTIHALIFAWNKWIDIKQFVWYTPPTFMIAVFLPIV
VLIFKSILFLPCLRKKILKIRHGWEDVTKINKTEICSQLKL*

DNA sequence of huSTEAP protein (SEQ ID NO: 11):
ATGGAATCACGGAAGGACATCACTAATCAGGAGGAACTGTGGAAAATGAAGCCAA
GAAGGAATCTGGAAGAGGACGACTATCTGCACAAGGACACCGGCGAAACAAGTAT
GCTGAAACGACCAGTGCTGCTGCACCTGCATCAGACTGCTCACGCAGACGAGTTTG
ATTGCCCCTCTGAACTGCAGCACACCCAGGAGCTGTTCCCACAGTGGCATCTGCCCA
TCAAGATTGCCGCTATCATTGCTTCACTGACATTTCTGTACACTCTGCTGAGAGAAGT
GATCCACCCCCTGGCCACCAGCCATCAGCAGTACTTCTATAAGATCCCTATCCTGGT
CATCAACAAGGTCCTGCCAATGGTGAGCATCACACTGCTGGCCCTGGTCTACCTGCC
TGGAGTGATCGCAGCCATTGTCCAGCTGCACAATGGGACAAAGTATAAGAAATTTC
CACATTGGCTGGATAAGTGGATGCTGACTAGGAAACAGTTCGGACTGCTGTCCTTCT
TTTTCGCCGTGCTGCACGCTATCTACAGCCTGTCCTATCCCATGAGGAGGAGCTACC
GGTATAAGCTGCTGAACTGGGCTTACCAGCAGGTGCAGCAGAACAAGGAGGACGCA
TGGATTGAACATGACGTGTGGCGCATGGAAATCTACGTGAGCCTGGGCATTGTCGG
ACTGGCCATCCTGGCTCTGCTGGCAGTGACCAGTATCCCTTCTGTCAGTGACTCACT
GACATGGAGAGAGTTTCACTACATTCAGAGCAAGCTGGGGATCGTGTCCCTGCTGCT
GGGCACCATCCATGCACTGATTTTTGCCTGGAACAAGTGGATCGATATCAAGCAGTT
CGTGTGGTATACTCCCCCTACCTTTATGATTGCCGTCTTCCTGCCCATCGTGGTCCTG
ATCTTCAAGTCCATCCTGTTCCTGCCTTGTCTGCGGAAGAAAATCCTGAAAATTCGG
CACGGATGGGAGGATGTCACCAAAATCAATAAGACTGAAATCTGTAGCCAGCTGAA
GCTTTAA Protein sequence of NYESO1 MAR protein (SEQ ID NO: 13):
MQAEGRGTGGSTGDADPGGPGIPDGPGGNAGGPGEAGATGGRGPRGAGAARASGPG
GGAPRGPHGGAASGLNGCCRCGARGPESRLLEFYLAMPFATPMEAELARRSLAQDAPP
LPVPGVLLKEFTVSGNILTIRLTAADHRQLQLSISSCLQQLSLLMWITQCFLPVFLAQPPS
GQRR*

APPENDIX A-continued

Protein and Nucleotide Sequences

DNA sequence of NYESO1 MAR (SEQ ID NO: 14):
ATGCAGGCCGAGGGCAGAGGCACAGGCGGATCTACAGGCGACGCCGATGGCCCTG
GCGGCCCTGGAATTCCTGACGGACCTGGCGGCAATGCCGGCGGACCCGGAGAAGCT
GGGCGCCACAGGCGGAAGAGGACCTAGAGGCGCTGGCGCCGCTAGAGCTTCTGGACC
AGGCGGAGGCGCCCCTAGAGGACCTCATGGCGGAGCCGCCTCCGGCCTGAACGGCT
GTTGCAGATGTGGAGCCAGAGGCCCCGAGAGCCGGCTGCTGGAATTCTACCTGGCC
ATGCCCTTCGCCACCCCCATGGAAGCCGAGCTGGCCAGACGGTCCCTGGCCCAGGA
TGCTCCTCCTCTGCCTGTGCCCGGCGTGCTGCTGAAAGAATTCACCGTGTCCGGCAA
CATCCTGACCATCCGGCTGACTGCCGCCGACCACAGACAGCTCCAGCTGTCTATCAG
CTCCTGCCTGCAGCAGCTGAGCCTGCTGATGTGGATCACCCAGTGCTTTCTGCCCGT
GTTCCTGGCTCAGCCCCCAGCGGCCAGAGAAGATGA Protein sequence of EBDNA1 (SEQ ID NO: 16):
MPVGQADYFEYHQEGGPDGEPDMPPGAIEQGPADDPGEGPSTGPRGQGDGGRRKKGG
WFGKHRGQGGSNQKFENIADGLRTLLARCHVERTTDEGTWVAGVFVYGGSKTSLYNL
RRGISLAIPQCRLTPLSRLPFGMAPGPGPQPGPLRESIVCYFIVFLQTHIFAEGLKDAIKDL
VMPKPAPTCNIKATVCSFDDGVDLPPWFPPMVEGAAAEGDDGDDGDDGDEGGDGEG
EEGQE*

DNA sequence of EBDNA1 (SEQ ID NO: 17):
ATGCCAGTCGGCCAGGCTGATTACTTTGAATACCACCAGGAGGGGGGACCAGACGG
AGAACCAGACATGCCACCAGGAGCCATTGAACAGGGACCAGCAGACGATCCTGGA
GAGGGACCATCAACTGGACCCCGAGGACAGGGGGACGGCGGAAGGAGAAAGAAAG
GGGGATGGTTCGGAAAGCACCGAGGACAGGGAGGGAGCAACCAGAAATTTGAAAA
TATCGCTGACGGCCTGCGAACACTGCTGGCAAGGTGCCATGTGGAGAGAACCACAG
ATGAAGGCACATGGGTCGCCGGAGTGTTCGTCTACGGCGGAAGCAAGACTTCCCTG
TATAACCTGCGGCGCGGCATCTCTCTGGCCATTCCACAGTGCCGGCTGACCCCTCTG
AGTCGCCTGCCATTCGGGATGGCTCCTGGACCAGGACCACAGCCTGGACCACTGAG
GGAGTCCATCGTGTGCTACTTCATTGTCTTTCTGCAGACACATCTTTGCCGAAGGC
CTGAAGGACGCCATCAAGGACCTGGTCATGCCCAAGCCTGCACCAACTTGCAATAT
CAAGGCCACCGTGTGCAGTTTCGACGATGGCGTGGACCTGCCCCCTTGGTTTCCACC
TATGGTGGAGGGAGCCGCTGCAGAAGGGGACGATGGCGATGACGGGACGATGGG
GATGAAGGCGGGACGGCGATGAGGGAGAAGAGGGGCAGGAATAA

What is claimed is:

1. A method of inducing an immune response against a cancer in a mammal, said cancer being a tumour expressing an HPV protein, said method comprising:
   a) administering a first virus comprising a nucleic acid capable of expressing an HPV tumour associated antigen, wherein said first virus is capable of generating immunity to said HPV tumour associated antigen;
   b) administering a second virus, said second virus being a Vesiculovirus, said second virus comprising a nucleic acid capable of expressing an HPV tumour associated antigen,
   wherein said second virus is capable of providing a therapeutic oncolytic effect in said mammal;
   wherein said first virus is immunologically distinct and physically isolated from said second virus; and
   wherein the amino acid sequence of the HPV tumour associated antigen comprises the amino acid sequence of SEQ ID NO. 7.

2. The method of claim 1, wherein said second virus is Maraba MG1.

3. The method of claim 2, wherein the amino acid sequence of the HPV tumour associated antigen consists of the amino acid sequence of SEQ ID NO:7.

4. The method of claim 3, wherein the amino acid sequence of the HPV tumour associated antigen is encoded by the nucleotide sequence of SEQ ID NO: 8.

5. The method of claim 4, wherein the Maraba MG1 genome comprises a reverse complement and RNA version of the nucleotide sequence of SEQ ID NO: 9.

6. The method of claim 1, wherein the amino acid sequence of the HPV tumour associated antigen consists of the amino acid sequence of SEQ ID NO: 7.

7. The method of claim 6, wherein the amino acid sequence of the HPV tumour associated antigen is encoded by the nucleotide sequence of SEQ ID NO: 8.

8. The method of claim 1, wherein said first and second virus both express the same HPV tumour associated antigen.

9. The method of claim 1, wherein the cancer expresses HPV E6 or E7 proteins as antigenic proteins.

10. The method of claim 1, wherein the cancer is cervical cancer.

11. The method of claim 1, wherein said first virus is administered intramuscularly.

12. The method of claim 2, wherein said second virus is administered intravenously.

13. The method of claim 12, wherein said first virus is administered intramuscularly.

* * * * *

SEQUENCE LISTING

<160> NUMBER OF SEQ ID NOS: 50

<210> SEQ ID NO 1
<211> LENGTH: 314
<212> TYPE: PRT
<213> ORGANISM: Homo sapiens

<400> SEQUENCE: 1

Met Pro Leu Glu Gln Arg Ser Gln His Cys Lys Pro Glu Glu Gly Leu
1               5                   10                  15

Glu Ala Arg Gly Glu Ala Leu Gly Leu Val Gly Ala Gln Ala Pro Ala
            20                  25                  30

Thr Glu Glu Gln Glu Ala Ala Ser Ser Ser Thr Leu Val Glu Val
        35                  40                  45

Thr Leu Gly Glu Val Pro Ala Ala Glu Ser Pro Asp Pro Pro Gln Ser
    50                  55                  60

Pro Gln Gly Ala Ser Ser Leu Pro Thr Thr Met Asn Tyr Pro Leu Trp
65                  70                  75                  80

Ser Gln Ser Tyr Glu Asp Ser Ser Asn Gln Glu Glu Glu Gly Pro Ser
                85                  90                  95

Thr Phe Pro Asp Leu Glu Ser Glu Phe Gln Ala Ala Leu Ser Arg Lys
            100                 105                 110

Val Ala Glu Leu Val His Phe Leu Leu Leu Lys Tyr Arg Ala Arg Glu
        115                 120                 125

Pro Val Thr Lys Ala Glu Met Leu Gly Ser Val Val Gly Asn Trp Gln
    130                 135                 140

Tyr Phe Phe Pro Val Ile Phe Ser Lys Ala Ser Ser Ser Leu Gln Leu

```
                145                 150                 155                 160
Val Phe Gly Ile Glu Leu Met Glu Val Asp Pro Ile Gly His Leu Tyr
                    165                 170                 175
Ile Phe Ala Thr Cys Leu Gly Leu Ser Tyr Asp Gly Leu Leu Gly Asp
                180                 185                 190
Asn Gln Ile Met Pro Lys Ala Gly Leu Leu Ile Ile Val Leu Ala Ile
                195                 200                 205
Ile Ala Arg Glu Gly Asp Cys Ala Pro Glu Lys Ile Trp Glu Glu
            210                 215                 220
Leu Ser Val Leu Glu Val Phe Glu Gly Arg Glu Asp Ser Ile Leu Gly
225                 230                 235                 240
Asp Pro Lys Lys Leu Leu Thr Gln His Phe Val Gln Glu Asn Tyr Leu
                    245                 250                 255
Glu Tyr Arg Gln Val Pro Gly Ser Asp Pro Ala Cys Tyr Glu Phe Leu
                260                 265                 270
Trp Gly Pro Arg Ala Leu Val Glu Thr Ser Tyr Val Lys Val Leu His
                    275                 280                 285
His Met Val Lys Ile Ser Gly Gly Pro His Ile Ser Tyr Pro Pro Leu
                290                 295                 300
His Glu Trp Val Leu Arg Glu Gly Glu Glu
305                 310

<210> SEQ ID NO 2
<211> LENGTH: 945
<212> TYPE: DNA
<213> ORGANISM: Homo sapiens

<400> SEQUENCE: 2
atgcctcttg agcagaggag tcagcactgc aagcctgaag aaggccttga ggcccgagga     60
gaggccctgg gcctggtggg tgcgcaggct cctgctactg aggagcagga ggctgcctcc    120
tcctcttcta ctctagttga agtcaccctg ggggaggtgc ctgctgccga gtcaccagat    180
cctccccaga gtcctcaggg agcctccagc ctccccacta ccatgaacta ccctctctgg    240
agccaatcct atgaggactc cagcaaccaa gaagaggagg gccaagcac cttccctgac     300 ctggagtccg agttccaagc agcactcagt aggaaggtgg ccgagttggt tcattttctg    360
ctcctcaagt atcgagccag ggagccggtc acaaaggcag aaatgctggg gagtgtcgtc    420
ggaaattggc agtatttctt tcctgtgatc ttcagcaaag cttccagttc cttgcagctg    480
gtctttggca tcgagctgat ggaagtggac cccatcggcc acttgtacat ctttgccacc    540
tgcctgggcc tctcctacga tggcctgctg ggtgacaatc agatcatgcc caaggcaggc    600
ctcctgataa tcgtcctggc cataatcgca agagagggcg actgtgcccc tgaggagaaa    660
atctgggagg agctgagtgt gttagaggtg tttgagggga gggaagacag tatcttgggg    720
gatcccaaga agctgctcac ccaacatttc gtgcaggaaa actacctgga gtaccggcag    780
gtccccggca gtgatcctgc atgttatgaa ttcctgtggg gtccaagggc cctcgttgaa    840
accagctatg tgaaagtcct gcaccatatg gtaaagatca gtggaggacc tcacatttcc    900
tacccacccc tgcatgagtg ggttttgaga gaggggaag agtga                     945

<210> SEQ ID NO 3
<211> LENGTH: 942
<212> TYPE: DNA
<213> ORGANISM: Artificial Sequence
<220> FEATURE:
<223> OTHER INFORMATION: codon optimized nucleotide sequence encoding
``` full length, wild type, human MAGEA3 protein

<400> SEQUENCE: 3

| | | | | | |
|---|---|---|---|---|---|
| atgcccctgg | agcagcggtc | tcagcattgc | aagccagagg | agggcctcga | ggcgaggggc | 60 |
| gaggcccctcg | gcttggtggg | ggcgcaggct | cctgcaaccg | aggagcaaga | ggccgcatcc | 120 |
| agttcctcta | ccctggttga | ggtgaccttg | ggtgaggtgc | ccgccgcgga | gagccccgac | 180 |
| ccgcctcaaa | gccccagggg | tgccagctcc | ctgcccacaa | caatgaacta | cccactctgg | 240 |
| agtcagtctt | acgaggacag | tagtaaccaa | gaggaggagg | gaccctccac | attcccagac | 300 |
| ctggagtctg | aattccaggc | agcattgtct | agaaaagtgg | ccgaattggt | gcacttcctg | 360 |
| ctgctgaagt | atcgcgcccg | cgagccagtc | acaaaagctg | aaatgctggg | ttctgtcgtg | 420 |
| ggaaattggc | agtacttctt | ccccgtgatc | ttcagtaaag | cgtccagctc | cttgcagctg | 480 |
| gtctttggta | tcgagctgat | ggaggtggat | cccatcggcc | atctgtatat | ctttgccaca | 540 |
| tgcctgggcc | tgagctacga | tggcctgctg | ggcgacaacc | agatcatgcc | aaaagctggc | 600 |
| ctgctgatca | tcgttctggc | tatcatcgct | agagaaggag | attgcgcccc | tgaagaaaag | 660 |
| atctgggagg | aactgagcgt | cctggaagtc | tttgagggtc | gtgaagacag | cattctcggg | 720 |
| gatcccaaga | agctgctgac | ccagcacttc | gtgcaggaga | actatctgga | gtaccgccag | 780 |
| gttcccggca | gcgaccccgc | ttgctacgag | ttcctgtggg | gccccagggc | cctggtcgag | 840 |
| acatcctacg | tgaaggtcct | gcaccatatg | gttaaaatca | gcggcggccc | ccatatctct | 900 |
| tatccgccgc | tccacgagtg | ggtgctccgg | gagggagagg | ag | | 942 |

<210> SEQ ID NO 4
<211> LENGTH: 322
<212> TYPE: PRT
<213> ORGANISM: Artificial Sequence
<220> FEATURE:
<223> OTHER INFORMATION: variant of MAGEA3 protein derived from homo sapiens

<400> SEQUENCE: 4

Met Pro Leu Glu Gln Arg Ser Gln His Cys Lys Pro Glu Glu Gly Leu
1               5                   10                  15

Glu Ala Arg Gly Glu Ala Leu Gly Leu Val Gly Ala Gln Ala Pro Ala
            20                  25                  30

Thr Glu Glu Gln Glu Ala Ala Ser Ser Ser Thr Leu Val Glu Val
        35                  40                  45

Thr Leu Gly Glu Val Pro Ala Ala Glu Ser Pro Asp Pro Pro Gln Ser
    50                  55                  60

Pro Gln Gly Ala Ser Ser Leu Pro Thr Thr Met Asn Tyr Pro Leu Trp
65                  70                  75                  80

Ser Gln Ser Tyr Glu Asp Ser Ser Asn Gln Glu Glu Glu Gly Pro Ser
                85                  90                  95

Thr Phe Pro Asp Leu Glu Ser Glu Phe Gln Ala Ala Leu Ser Arg Lys
            100                 105                 110

Val Ala Glu Leu Val His Phe Leu Leu Leu Lys Tyr Arg Ala Arg Glu
        115                 120                 125

Pro Val Thr Lys Ala Glu Met Leu Gly Ser Val Val Gly Asn Trp Gln
    130                 135                 140

Tyr Phe Phe Pro Val Ile Phe Ser Lys Ala Ser Ser Ser Leu Gln Leu
145                 150                 155                 160

Val Phe Gly Ile Glu Leu Met Glu Val Asp Pro Ile Gly His Leu Tyr
                165                 170                 175

```
Ile Phe Ala Thr Cys Leu Gly Leu Ser Tyr Asp Gly Leu Leu Gly Asp
            180                 185                 190

Asn Gln Ile Met Pro Lys Ala Gly Leu Leu Ile Ile Val Leu Ala Ile
        195                 200                 205

Ile Ala Arg Glu Gly Asp Cys Ala Pro Glu Glu Lys Ile Trp Glu Glu
210                 215                 220

Leu Ser Val Leu Glu Val Phe Glu Gly Arg Glu Asp Ser Ile Leu Gly
225                 230                 235                 240

Asp Pro Lys Lys Leu Leu Thr Gln His Phe Val Gln Glu Asn Tyr Leu
                245                 250                 255

Glu Tyr Arg Gln Val Pro Gly Ser Asp Pro Ala Cys Tyr Glu Phe Leu
            260                 265                 270

Trp Gly Pro Arg Ala Leu Val Glu Thr Ser Tyr Val Lys Val Leu His
        275                 280                 285

His Met Val Lys Ile Ser Gly Gly Pro His Ile Ser Tyr Pro Pro Leu
    290                 295                 300

His Glu Trp Val Leu Arg Glu Gly Glu Glu Asp Tyr Lys Asp Asp Asp
305                 310                 315                 320

Asp Lys

<210> SEQ ID NO 5
<211> LENGTH: 969
<212> TYPE: DNA
<213> ORGANISM: Artificial Sequence
<220> FEATURE:
<223> OTHER INFORMATION: nucleotide sequence encoding variant of MAGEA3
      protein derived from homo sapiens

<400> SEQUENCE: 5
atgcccctgg aacagcggag ccagcactgc aagcccgagg aaggcctgga agccagaggc      60
gaagccctgg gactggtggg agcccaggcc cctgccacag aagaacagga agccgccagc     120
agcagctcca ccctggtgga agtgaccctg ggcgaagtgc ctgccgccga gagccctgat     180
ccccctcagt ctcctcaggg cgccagcagc ctgcccacca ccatgaacta ccccctgtgg     240
tcccagagct acgaggacag cagcaaccag gaagaggaag cccccagcac cttccccgac     300
ctggaaagcg agttccaggc cgccctgagc cggaaggtgg cagagctggt gcacttcctg     360
ctgctgaagt acagagcccg cgagcccgtg accaaggccg agatgctggg cagcgtggtg     420
ggaaactggc agtacttctt ccccgtgatc ttctccaagg ccagcagctc cctgcagctg     480
gtgttcggca tcgagctgat ggaagtggac cccatcggcc acctgtacat cttcgccacc     540
tgtctgggcc tgagctacga cggcctgctg ggcgacaacc agatcatgcc aaggccggc      600 ctgctgatca tcgtgctggc catcattgcc cgcgagggca ctgcgcccc tgaggaaaag     660 atctggagg aactgagcgt gctggaagtg ttcgagggca gagaggacag catcctgggc     720
gaccccaaga agctgctgac ccagcacttc gtgcaggaaa actacctgga ataccgccag     780
gtgcccggca gcgaccccgc ctgttacgag ttcctgtggg gccccagggc tctggtggaa     840
accagctacg tgaaggtgct gcaccacatg gtgaaaatca gcggcggacc ccacatcagc     900
taccccccac tgcacgagtg ggtgctgaga gagggcgaag aggactacaa ggacgacgac     960
gacaaatga                                                            969

<210> SEQ ID NO 6
<211> LENGTH: 14297
<212> TYPE: DNA
```

<213> ORGANISM: Artificial Sequence
<220> FEATURE:
<223> OTHER INFORMATION: nucleotide encoding an artificial Maraba virus
      that expresses a MAGEA3 protein

<400> SEQUENCE: 6

```
aagcttgata tcattcagga cgagcctcag actccagcgt aactggactg caatcaactc    60
actggctcac cttcacgggt gggcctttct tcggtagaaa atcaaaggat cttcttgaga   120
tcctttttt ctgcgcgtaa tctgctgctt gcaaacaaaa aaaccaccgc taccagcggt    180
ggtttgtttg ccggatcaag agctaccaac tcttttttccg aggtaactgg cttcagcaga   240
gcgcagatac caaatactgt tcttctagtg tagccgtagt taggccacca cttcaagaac   300
tctgtagcac cgcctacata cctcgctctg ctaatcctgt taccagtggc tgctgccagt    360
ggcgataagt cgtgtcttac cgggttggac tcaagacgat agttaccgga taaggcgcag    420
cggtcgggct gaacggggg ttcgtgcaca cagcccagct tggagcgaac gacctacacc    480
gaactgagat acctacagcg tgagctatga gaaagcgcca cgcttcccga agggagaaag    540
gcggacaggt atccggtaag cggcagggtc ggaacaggag agcgcacgag ggagcttcca    600
gggggaaacg cctggtatct ttatagtcct gtcgggtttc gccacctctg acttgagcat    660
cgatttttgt gatgctcgtc aggggggcgg agcctatgga aaaacgccag caacgcagaa    720
aggcccaccc gaaggtgagc caggtgatta catttgggcc ctcatcagag gttttcaccg    780
tcatcaccga aacgcgcgag gcagctgcgg taaagctcat cagcgtggtc gtgaagcgat    840
tcacagatgt ctgcctgttc atccgcgtcc agctcgttga gtttctccag aagcgttaat    900
gtctggcttc tgataaagcg ggccatgtta agggcggttt tttcctgttt ggtcatttag    960
aaaaactcat cgagcatcaa gtgaaactgc aatttattca tatcaggatt atcaatacca   1020
tattttgaa aaagccgttt ctgtaatgaa ggagaaaact caccgaggca gttccatagg   1080
atggcaagat cctggtatcg gtctgcgatt ccgactcgtc caacatcaat acaacctatt   1140
aatttcccct cgtcaaaaat aaggttatca agtgagaaat caccatgagt gacgactgaa   1200
tccggtgaga atggcaaaag cttatgcatt tctttccaga cttgttcaac aggccagcca   1260
ttacgctcgt catcaaaatc actcgcacca accaaaccgt tattcattcg tgattgcgcc   1320
tgagcgagac gaaatacgcg atcgccgtta aaggacaat tacaaacagg aatcgaatgc   1380
aaccggcgca ggaacactgc cagcgcatca acaatatttt cacctgaatc aggatattct   1440
tctaatacct ggaatgctgt ttttccctggg atcgcagtgg tgagtaacca tgcatcatca   1500
ggagtacgga taaaatgctt gatggtcgga agaggcataa attccgtcag ccagtttagc   1560
ctgaccatct catctgtaac atcattggca acgctacctt tgccatgttt cagaaacaac   1620
tctggcgcat cgggcttccc atacaatcga tagattgtcg cacctgattg cccgacatta   1680
tcgcgagccc atttataccc atataaatca gcatccatgt tggaatttaa tcgcggcctc   1740
gagcaagacg tttcccgttg aatatggctc attttagctt ccttagctcc tgaaaatctc   1800
gataactcaa aaaatacgcc cggtagtgat cttatttcat tatggtgaaa gttggaacct   1860
cttacgtgcc gatcaagtca aaagcctccg gtcggaggct tttgactttc tgctatggag   1920
gtcaggtatg atttaaatgg tcagtattga gcgatatcta gagaattcgt ctaatacgac   1980
tcactatagg gacgaagaca aacaaaccat tgatagaatt aagaggctca tgaaaatcct   2040
taacagcgtt caaatgtctc gttacagtca agagagtcat tgatgattca ctcatcaccc   2100
ccaaattgcc tgcgaatgag gaccctgtgg agtaccctgc tgattatttc aaaaagtccc   2160
```

```
gtgatattcc ggtgtacata aacacgacca aaagtttgtc tgatttgcgg ggctatgttt    2220
atcaaggcct aaagtcaggc aacatctcta taattcatgt caacagttat ctgtatgcag    2280
cattaaaaga gatcagagga aaattggaca gagattggat cacctttggt atccaaatcg    2340 gaaaacagg  agatagcgtg gggatattcg atttactgac cctaaaacct ctagatggtg    2400
ttttaccaga tggggtgtct gatgctactc gaactagctc agacgatgca tggcttccac    2460
tgtatctatt ggggttatac agagttggtc gaacacagat gccagaatac aggaagaagc    2520
tgatggatgg tctgattaat caatgtaaga tgatcaatga gcagtttgaa ccactgttgc    2580
cagaaggaag agatgtcttt gatgtctggg gaaatgacag caattacaca agattgtgg    2640 ccgctgtaga tatgttcttc catatgttca aaaagcatga aaggcctct  ttcaggtatg    2700 gcacaatagt gtcaagattt aaggattgtg cagcattggc tacatttggt catctgtgta    2760
agatcactgg tatgtccact gaagatgtga caacttggat tctaaacagg gaggtggctg    2820
atgagatggt tcaaatgatg tacccaggac aggagataga taaggctgat tcttacatgc    2880
cttatctaat cgacttaggt ctgtcctcaa aatctcccata ttcatcagtt aaaaatccag    2940
ctttccattt ttggggtcaa ttgaccgcat tgttactgag atcaaccaga gccagaaatg    3000
cacgtcagcc ggatgacatc gagtatacat ccctgaccac tgctgggctg ttgtatgcat    3060
atgccgttgg ttcgtctgca gacctggctc aacaattcta cgttggggac aacaagtatg    3120
tgccagaaac tggagatgga ggattaacca ccaatgcacc gccacaaggg cgagatgtgg    3180
tcgagtggct tagttggttt gaagatcaaa acagaaaacc taccccagac atgctcatgt    3240
atgctaagag agctgtcagt gctttacaag gattgaggga gaagacgatt ggcaagtacg    3300
ccaagtcaga gtttgacaaa tgacaactca ctcaccatat gtattactac ctttgcttca    3360 tatgaaaaa  actaacagcg atcatggatc agctatcaaa ggtcaaggaa ttccttaaga    3420
cttacgcgca gttggatcaa gcagtacaag agatggatga cattgagtct cagagagagg    3480
aaaagactaa ttttgatttg tttcaggaag aaggattgga gattaaggag aagccttcct    3540
attatcgggc agatgaagaa gagattgatt cagatgaaga cagcgtggat gatgcacaag    3600
acttagggat acgtacatca acaagtccca tcgaggggta tgtggatgag agcaggatg    3660 attatgagga tgaggaagtg aacgtggtgt ttacatcgga ctggaaacag cctgagctgg    3720
aatccgacgg ggatgggaaa actctccgat tgacgatacc agatggattg actggggagc    3780
agaagtcgca atggcttgcc acgattaagg cagttgttca gagtgctaaa tattggaaca    3840
tctcagaatg ttcatttgag agttatgagc aaggggtttt gattagagag agacaaatga    3900
ctcctgatgt ctacaaagtc actcctgttt taaatgctcc accggttcaa atgacagcta    3960
atcaagatgt ttggtctctc agcagcactc catttacatt tttgcccaag aaacaaggtg    4020
tgactccatt gaccatgtcc ttagaagaac tcttcaacac ccgaggtgaa ttcatatctc    4080
tgggaggaaa cgggaaaatg agtcaccggg aggccatcat tctagggttg agacacaaga    4140
agctctataa tcaagccaga ctaaagtata acttagcttg aatatgaaaa aaactaacag    4200
atatcaaaag atatctctaa ctcagtccat tgtgttcagt tcaatcatga gctctctcaa    4260
gaaaattttg ggtattaaag ggaaagggaa gaaatctaag aaattaggta tggctccccc    4320 acccctatgaa gaagagactc caatggaata ttctccaagt gcaccttatg ataagtcatt    4380
gtttggagtc gaagatatgg atttccatga tcaacgtcaa ctccgatatg agaaatttca    4440
cttctcattg aagatgactg tgagatcaaa caaaccattt cgaaattatg atgacgttgc    4500
agcagcggtg tccaattggg atcatatgta catcggcatg gcaggaaaac gtccttttta    4560
```

```
taagatatta gcattcatgg gttctactct attgaaggct acaccagccg tctgggctga    4620
ccaaggacag ccagaatatc atgctcactg tgagggacga gcttacttgc cgcatcggtt    4680
agggccgacc cctccgatgt tgaatgtccc tgaacatttt cgccgtccat ttaacatcgg    4740
attattcaga gggacaatcg acataaccct ggtacttttc gatgatgaat ctgtagattc    4800
tgccccggtc atatgggatc attttaatgc atccagattg agcagcttca gagaaaaggc    4860
tttgttgttt ggtttgattc tagaaaagaa agccactggg aattgggtat tggactctat    4920
tagtcatttc aagtaattat cacaagtgtt gaggtgatgg gcagactatg aaaaaaacta    4980
acagggttca acactcttg atcgaggtac ccagttatat ttgttacaac aatgttgaga    5040 cttttctct tttgtttctt ggccttagga gcccactcca aatttactat agtattccct    5100
catcatcaaa aagggaattg gaagaatgtg ccttccacat atcattattg cccttctagt    5160
tctgaccaga attggcataa tgatttgact ggagttagtc ttcatgtgaa aattcccaaa    5220
agtcacaaag ctatacaagc agatggctgg atgtgccacg ctgctaaatg ggtgactact    5280
tgtgacttca gatggtacgg acccaaatac atcacgcatt ccatacactc tatgtcaccc    5340
accctagaac agtgcaagac cagtattgag cagacaaagc aaggagtttg gattaatcca    5400
ggctttcccc ctcaaagctg cggatatgct acagtgacgg atgcagaggt ggttgttgta    5460
caagcaacac ctcatcatgt gttggttgat gagtacacag gagaatggat tgactcacaa    5520
ttggtggggg gcaaatgttc caaggaggtt tgtcaaacgg ttcacaactc gaccgtgtgg    5580
catgctgatt acaagattac agggctgtgc gagtcaaatc tggcatcagt ggatatcacc    5640
ttcttctctg aggatggtca aaagacgtct ttgggaaaac cgaacactgg attcaggagt    5700
aatcactttg cttacgaaag tggagagaag gcatgccgta tgcagtactg cacacgatgg    5760
ggaatccgac taccttctgg agtatggttt gaattagtgg acaaagatct cttccaggcg    5820
gcaaaattgc ctgaatgtcc tagaggatcc agtatctcag ctccttctca gacttctgtg    5880
gatgttagtt tgatacaaga cgtagagagg atcttagatt actctctatg ccaggagacg    5940
tggagtaaga tacgagccaa gcttcctgta tctccagtag atctgagtta tctcgcccca    6000
aaaaatccag ggagcggacc ggccttcact atcattaatg gcactttgaa atatttcgaa    6060
acaagataca tcagagttga cataagtaat cccatcatcc ctcacatggt gggaacaatg    6120
agtggaacca cgactgagcg tgaattgtgg aatgattggt atccatatga agacgtagag    6180
attggtccaa atggggtgtt gaaaactccc actggtttca gtttccgct gtacatgatt    6240 gggcacggaa tgttggattc cgatctccac aaatcctccc aggctcaagt cttcgaacat    6300
ccacacgcaa aggacgctgc atcacagctt cctgatgatg agactttatt ttttggtgac    6360
acaggactat caaaaaaccc agtagagtta gtagaaggct ggttcagtag ctggaagagc    6420
acattggcat cgttctttct gattataggc ttggggttg cattaatctt catcattcga    6480
attattgttg cgattcgcta taaatacaag gggaggaaga cccaaaaaat ttacaatgat    6540
gtcgagatga gtcgattggg aaataaataa cagatgacgc atgagggtca gatcagattt    6600
acagcgtaag tgtgatattt aggattataa aggttcctta attttaattt gttacgcgtt    6660
gtatgaaaaa aactcatcaa cagccatcgc caccatgccc ctgaacagc ggagccagca    6720 ctgcaagccc gaggaaggcc tggaagccag aggcgaagcc ctgggactgg tgggagccca    6780
ggcccctgcc acagaagaac aggaagccgc cagcagcagc tccaccctgg tggaagtgac    6840
cctgggcgaa gtgcctgccg ccgagagccc tgatcccct cagtctcctc agggcgccag    6900
```

```
cagcctgccc accaccatga actacccect gtggtcccag agctacgagg acagcagcaa      6960
ccaggaagag gaaggcccca gcaccttccc cgacctggaa agcgagttcc aggccgccct      7020
gagccggaag gtggcagagc tggtgcactt cctgctgctg aagtacagag cccgcgagcc      7080
cgtgaccaag gccgagatgc tgggcagcgt ggtgggaaac tggcagtact tcttccccgt      7140
gatcttctcc aaggccagca gctccctgca gctggtgttc ggcatcgagc tgatggaagt      7200
ggaccccatc ggccacctgt acatcttcgc cacctgtctg gcctgagct acgacggcct       7260 gctgggcgac aaccagatca tgcccaaggc cggcctgctg atcatcgtgc tggccatcat      7320
tgcccgcgag ggcgactgcg cccctgagga aagatctgg gaggaactga gcgtgctgga      7380
agtgttcgag ggcagagagg acagcatcct gggcgacccc aagaagctgc tgacccagca      7440
cttcgtgcag gaaaactacc tggaataccg ccaggtgccc ggcagcgacc ccgcctgtta      7500
cgagttcctg tggggcccca gggctctggt ggaaaccagc tacgtgaagg tgctgcacca      7560
catggtgaaa atcagcggcg accccacat cagctacccc ccactgcacg agtgggtgct       7620
gagagagggc gaagaggact acaaggacga cgacgacaaa tgagtctgag cacgagttgc      7680
agacgcgttg tatgaaaaaa actcatcaac agccatcatg gatgttaacg attttgagtt      7740
gcatgaggac tttgcattgt ctgaagatga ctttgtcact tcagaatttc tcaatccgga      7800
agaccaaatg acatacctga atcatgccga ttataatttg aattctccct taatcagcga      7860
tgatattgat ttcctgatca agaaatataa tcatgagcaa attccgaaaa tgtgggatgt      7920
caagaattgg gagggagtgt tagagatgtt gacagcctgt caagccagtc aatttttatc      7980
tagcactatg cataagtggg tgggaaagtg gctcatgtct gatgatcatg acgcaagcca      8040
aggcttcagt tttcttcatg aagtggacaa agaagctgat ctgacgtttg aggtggtgga      8100
gacattcatt agaggatggg gaggtcgaga attgcagtac aagaggaaag acacatttcc      8160
ggactccttt agagttgcag cctcattgtg tcaaaaattc cttgatttgc acaaactcac      8220
tctgataatg aattcagtct ctgaagtcga acttaccaac ctagcaaaga atttttaaagg     8280 aaaaaacagg aaagcaaaaa gcggaaatct gataaccaga ttgagggttc ccagtttagg      8340
tcctgctttt gtgactcagg gatgggtgta catgaagaag ttggaaatga ttatggatcg      8400
gaattttttg ttgatgttga aagacgttat catcgggagg atgcagacga tcctgtccat      8460
gatctcaaga gatgataatc tcttctccga gtctgatatc tttactgtat taaagatata      8520
ccggataggg gataagatat tagaaaggca agggacaaag ggttacgact tgatcaaaat      8580
gattgagcct atttgtaact taaagatgat gaatctggca cgtaaatatc gtcctctcat      8640
ccctacattt cctcatttg aaaaacatat tgctgactct gttaaggaag gatcgaaaat       8700
agacaaaggg attgagttta tatatgatca cattatgtca atccctggtg tggacttgac      8760
cttagttatt tacggatcat ttcggcactg gggtcatcct tttatcaact actatgaggg      8820
cttagagaag ctacacaagc aggttacaat gcccaagact attgacagag aatatgcaga      8880
atgtcttgct agtgatctgg caagaatcgt tcttcagcaa caattcaatg aacataagaa      8940
atggtttgtt gatgtagata agtcccaca atcccatcct ttcaaaagcc atatgaaaga       9000
gaatacttgg cctactgcag cccaagttca ggattacggc gatcgctggc atcagctccc      9060
actcatcaaa tgcttcgaaa tcccagattt gttagatcca tcgatcatct actcagacaa      9120
aagtcattcc atgaaccggt ctgaagtact acgacatgta agacttacac ctcatgtgcc      9180
cattccaagc aggaaagtat tgcagacaat gttggagact aaggcaacag actgaaaga      9240 gttttttaaag aaaattgacg aagaggggtt agaggatgat gatcttgtca taggactcaa      9300
```

```
agggaaagag agagaattaa aaattgcggg aagattcttt tctttgatgt cctggaagct    9360
cagagagtat tttgtcatca ctgagtattt gattaagacg cactttgtcc cgatgtttaa    9420
agggttgacc atggcggatg acttgacagc ggtgataaag aagatgatgg acacatcttc    9480
aggacaaggc ttagataatt atgaatccat ttgtatagcc aaccatattg actatgagaa    9540
gtggaacaat catcaaagaa aagagtcgaa cgggcccgtg ttcaaggtga tgggtcaatt    9600
cttgggatat ccacgtctga ttgagagaac tcatgaattt tttgagaaga gtctgatata    9660
ttacaatgga cgaccagatc tgatgcgggt tcgaggaaat tctctagtca acgcctcatc    9720
tttaaatgtc tgctgggagg gtcaagctgg gggattagaa ggactgcgac agaagggatg    9780
gagtattcta aatttgcttg tcattcagag agaagcaaaa ataaggaaca ccgccgtgaa    9840
agtgctagct caaggtgaca atcaggtgat atgtactcag tataaaacga agaaatcccg    9900
gaatgatatt gagcttaagg cagctctaac acagatggta tctaataatg agatgattat    9960
gtctgcgatt aaatcaggca ccgagaaact gggtcttttg attaatgatg atgagacaat   10020
gcaatctgct gattacctca attacgggaa ggttcccatt ttcagaggag taatcagagg   10080
ccttgagaca aaaagatggt cacgcgtgac ctgtgtgaca aatgatcaga ttccaacgtg   10140
tgcgaacatt atgagctctg tgtcaactaa tgcattaact gtagcccatt ttgccgagaa   10200
tccagtcaat gccatcattc agtataacta ctttggaaca tttgcaaggc tactgctgat   10260
gatgcatgac cccgctctga ggatctctct gtatgaagtc caatcaaaaa ttccaggact   10320
tcacagtttg acatttaaat attctatgtt gtatctggat ccttcgatag gaggagtctc   10380
cggaatgtca ctctcgagat tcctcataag atcatttcca gatccagtga cagaaagttt   10440
ggcgttctgg aaatttatcc actctcatgc aagaagcgat tcattaaagg agatatgtgc   10500
agtttttgga aatcctgaaa ttgcaagatt tcggctaact catgtcgata aattggtgga   10560
agacccaacc tcattgaaca tagctatggg aatgagtcct gctaatctat taaagacaga   10620
ggtaaaaaaa tgtctactgg aatcaaggca gagcatcaag aaccagattg taagagatgc   10680
tactatttac ctacaccatg aggaagacaa acttcgtagt ttcttatggt ccataacacc   10740
actgttccct cggttcttga gtgaattcaa atctgggaca ttcatcggag tagcagatgg   10800
cctgatcagc ttatttcaga actctaggac tattcgaaat tcttttaaaa agcgttatca   10860
cagggaactt gatgatttaa taatcaagag cgaagtttcc tcacttatgc atttgggtaa   10920
gctacatttg aggcgaggct cagttcgtat gtggacttgc tcttctactc aggctgatct   10980
tctccgattc cggtcatggg gaagatctgt tataggaacc acagtccctc atcccttaga   11040
gatgttagga caacattta aaaaggagac tccttgcagt gcttgcaaca tatccggatt   11100
agactatgta tctgtccact gtccgaatgg gattcatgac gttttttgaat cacgtggtcc   11160 actccctgca tatttgggtt ctaaaacatc cgaatcaact tcgatcttgc agccgtggga   11220
gagagagagt aaagtaccgt tgattaagcg tgccacaagg cttcgtgatg caatttcatg   11280
gtttgtgtct cccgactcta acttggcctc aactatcctt aagaacataa atgcattaac   11340
aggagaagaa tggtcaaaga agcagcatgg atttaaaagg acgggatcgg cgttacacag   11400
gttctccaca tccaggatga gtcatggtgg ttttttgcttct cagagtacgg ctgccttgac   11460
tagattgatg gcaactactg acactatgag agatctggga gaacagaact atgatttcct   11520
gtttcaggcg acattattgt atgctcaaat aaccacaact gtagtcagga atggatcatt   11580
tcatagctgc acggaccatt accatataac ctgcaaatct tgtctgaggg ccattgatga   11640
```

```
gattaccttg gattcagcga tggaatatag ccctccagat gtatcatcag tttttacaatc    11700 ttggaggaat ggagaaggct cttggggaca tgaagtgaaa caaatatacc cagttgaagg    11760
tgactggagg ggactatctc ctgttgaaca atcttatcaa gtcggacgct gtatcgggtt    11820
tctgttcggt gatctggcgt atagaaaatc atcccatgca gatgatagct ccatgtttcc    11880
gttatctata caaacaaag tcagaggaag aggctttta aaagggctta tggatgggtt     11940
aatgagagcc agttgttgcc aggtgatcca tcgtcgaagc ttagcccatc tgaagagacc    12000
ggctaatgca gtctatggag ggctgattta tttgatagac aaattgagtg catctgcccc    12060
ttttctttca ctgacgagac atggacctt aagggaagaa ttagaaactg ttccacataa    12120
gataccgact tcttatccta cgagcaaccg agatatgggg gtgatagttc gtaattattt    12180
taaatatcag tgcagactgg tagaaaaagg tcggtacaag acacattatc ctcaattgtg    12240
gcttttctca gatgtgctgt ccattgattt cttaggaccc ctgtctatat cttcaactct    12300
attgggtatt ctgtataaac agacgttatc ttctcgagac aaaaatgagt tgagagaact    12360
cgctaacttg tcttcattgt tgagatcagg agaaggatgg gaagatatcc atgtcaaatt    12420
cttctctaag gacactttac ctgccctga agagatccga catgcgtgca aatttgggat     12480
tgctaaggaa tccgctgttt taagctatta tcctccttgg tctcaagagt cttatgagg    12540 catcacctcg atccccgtat attttttcgac caggaagtat cccaaaattt tagatgtccc    12600
tcctcgggtt caaaacccat tggtctcggg tctacgattg gggcaactcc ctactggagc    12660
acattataag attaggagca ttgtaaagaa caagaaccttcgttatagag atttccttag    12720 ttgtggggat ggatctgggg gatgaccgc ggcactattg agagaaaaca gacaaagtag    12780
gggaatcttc aacagcctgt tagagttagc cggatctctt atgagaggag catctccaga    12840
gcctccaagt gcactggaga cgctcgggca agaacgatct aggtgtgtga atggaagcac    12900
atgtttggga gtactcatctg acctaagcca aaaagagaca tgggattact cttaagatt    12960 gaagagaggc ctgggtttga ccgtggactt aatcaccatg gacatggagg tcagagaccc    13020
taatacaagt ttgatgatag aaaagaacct caaagtttat ctgcatcaga tattagaacc    13080
aactggtgtc ttaatatata aaacatacgg gacccatatt gcgacacaaa cagataatat    13140
cctgacgata atcggtcctt tctttgagac ggttgaccta gtccagtccg aatacagcag    13200
ctcacaaacg tccgaggtct attttgtagg acgaggcttg cgctctcatg ttgacgaacc    13260
ctgggtggac tggccatcct taatggacaa ttggagatcc attatgctt tcatgatcc     13320 tactacagaa tttatcagag caaaaaaagt ctgtgaaatt gacagtctta taggcattcc    13380
ggctcaattc attccagacc catttgtaaa tctcgagacc atgctacaga tagttggtgt    13440
tccaacagga gtttcgcatg ccgcagctct attatcatca caatatccaa atcaattggt    13500
cacaacgtca atattttata tgacactcgt gtcttattat aatgtaaacc atattcgaag    13560
aagccccaag cctttctctc ctccgtctga tggagtctca cagaacattg gttcagccat    13620
agtcggacta agttttggg tgagtttgat ggagaatgat ctcggattat acaaacaggc    13680
tctaggtgca ataaagacgt cattccctat tagatggtcc tctgtccaga ccaaggatgg    13740
gtttacacaa gaatggagaa ctaaaggaaa cggaattcct aaagattgtc gtctctcaga    13800
ctctttggct cagataggaa actggatcag agcgatggaa ttggttagga acaaaacgag    13860
gcaatcagga ttttctgaaa ccctatttga tcaattctgc ggacttgcag accatccct     13920 caaatggcg aagttgggaa acagaacagg aattattgat tggctaaata atagaatttc    13980
atccattgac aaatccatct tggtgaccaa aagtgatctg catgacgaga actcatggag    14040
```

-continued

```
ggagtgaaga tgtattcttc cacctctcat tgggtgatac ccatatatga aaaaaactat   14100
aagtacttta aactctcttt gttttttaat gtatatctgg ttttgttgtt tccgtgccgg   14160
ccatggtccc agcctcctcg ctggcggccg gtgggcaaca ttccgagggg accgtcccct   14220
cggtaatgac gaatgggaca accccttggg gcctctaaac gggtcttgag gggttttttg   14280
gtttaaacaa cgaattc                                                 14297
```

<210> SEQ ID NO 7  
<211> LENGTH: 527  
<212> TYPE: PRT  
<213> ORGANISM: Artificial Sequence  
<220> FEATURE:  
<223> OTHER INFORMATION: fusion protein derived from E6 and E7 proteins of human papilloma virus

<400> SEQUENCE: 7

```
Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Tyr Asp Phe Ala Phe Arg Asp Leu Cys Ile Val Tyr Arg Asp Gly
    50                  55                  60

Asn Pro Tyr Ala Val Asp Lys Leu Lys Phe Tyr Ser Lys Ile Ser Glu
65                  70                  75                  80

Tyr Arg His Tyr Cys Tyr Ser Val Tyr Gly Thr Thr Leu Glu Gln Gln
                85                  90                  95

Tyr Asn Lys Pro Leu Cys Asp Leu Leu Ile Arg Ile Asn Gln Lys Pro
            100                 105                 110

Leu Cys Pro Glu Glu Lys Gln Arg His Leu Asp Lys Lys Gln Arg Phe
        115                 120                 125

His Asn Ile Arg Gly Arg Trp Thr Gly Arg Cys Met Ser Cys Cys Arg
130                 135                 140

Ser Ser Arg Thr Arg Arg Glu Thr Gln Leu Gly Gly Gly Gly Gly Ala
145                 150                 155                 160

Ala Tyr Met Ala Arg Phe Glu Asp Pro Thr Arg Arg Pro Tyr Lys Leu
                165                 170                 175

Pro Asp Leu Cys Thr Glu Leu Asn Thr Ser Leu Gln Asp Ile Glu Ile
            180                 185                 190

Thr Cys Val Tyr Cys Lys Thr Val Leu Glu Leu Thr Glu Val Phe Glu
        195                 200                 205

Phe Ala Phe Lys Asp Leu Phe Val Val Tyr Arg Asp Ser Ile Pro His
    210                 215                 220

Ala Ala His Lys Ile Asp Phe Tyr Ser Arg Ile Arg Glu Leu Arg His
225                 230                 235                 240

Tyr Ser Asp Ser Val Tyr Gly Asp Thr Leu Glu Lys Leu Thr Asn Thr
                245                 250                 255

Gly Leu Tyr Asn Leu Leu Ile Arg Leu Arg Gln Lys Pro Leu Asn Pro
            260                 265                 270

Ala Glu Lys Leu Arg His Leu Asn Glu Lys Arg Arg Phe His Asn Ile
        275                 280                 285

Ala Gly His Tyr Arg Gly Gln Cys His Ser Cys Cys Asn Arg Ala Arg
    290                 295                 300
```

```
Gln Glu Arg Leu Gln Arg Arg Glu Thr Gln Val Gly Gly Gly
305                 310                 315                 320

Gly Ala Ala Tyr Met His Gly Asp Thr Pro Thr Leu His Glu Tyr Met
                325                 330                 335

Leu Asp Leu Gln Pro Glu Thr Thr Asp Leu Tyr Gln Leu Asn Asp Ser
            340                 345                 350

Ser Glu Glu Glu Asp Glu Ile Asp Gly Pro Ala Gly Gln Ala Glu Pro
        355                 360                 365

Asp Arg Ala His Tyr Asn Ile Val Thr Phe Cys Cys Lys Cys Asp Ser
    370                 375                 380

Thr Leu Arg Leu Cys Val Gln Ser Thr His Val Asp Ile Arg Thr Leu
385                 390                 395                 400

Glu Asp Leu Leu Met Gly Thr Leu Gly Ile Val Pro Ile Cys Ser Gln
                405                 410                 415

Lys Pro Gly Gly Gly Gly Ala Ala Tyr Met His Gly Pro Lys Ala
                420                 425                 430

Thr Leu Gln Asp Ile Val Leu His Leu Glu Pro Gln Asn Glu Ile Pro
            435                 440                 445

Val Asp Leu Leu Gln Leu Ser Asp Ser Glu Glu Glu Asn Asp Glu Ile
450                 455                 460

Asp Gly Val Asn His Gln His Leu Pro Ala Arg Arg Ala Glu Pro Gln
465                 470                 475                 480

Arg His Thr Met Leu Cys Met Cys Cys Lys Cys Glu Ala Arg Ile Lys
                485                 490                 495

Leu Val Val Glu Ser Ser Ala Asp Asp Leu Arg Ala Phe Gln Gln Leu
            500                 505                 510

Phe Leu Asn Thr Leu Ser Phe Val Pro Trp Cys Ala Ser Gln Gln
            515                 520                 525

<210> SEQ ID NO 8
<211> LENGTH: 1584
<212> TYPE: DNA
<213> ORGANISM: Artificial Sequence
<220> FEATURE:
<223> OTHER INFORMATION: nucleotide sequence encoding fusion protein
      derived from E6 and E7 proteins of human papilloma virus

<400> SEQUENCE: 8
atgcatcaga agcgaactgc tatgtttcag gaccctcagg agcggccacg caaactgcct        60
cagctgtgca ccgaactgca gacaactatc cacgacatca ttctggaatg cgtgtactgt       120
aagcagcagc tgctgaggag agaggtctat gacttcgctt tcgcgatct gtgcatcgtg       180 taccgagacg aaacccata tgcagtcgat aagctgaagt tctacagcaa gatctccgaa       240
tacaggcatt actgttacag cgtgtacggg accacactgg agcagcagta taacaagccc       300
ctgtgcgacc tgctgatcag aattaatcag aagcccctgt gccctgagga aaaacagagg       360
cacctggata gaaacagag atttcataac atccgaggac gatggaccgg gcggtgcatg       420
tcctgctgta gaagctcccg gactcgacga gagacccagc tgggcggagg aggaggagca       480
gcttacatgg cacgattcga ggaccctacc cgaaggccat ataagctgcc cgacctgtgc       540
acagaactga atacttctct gcaggacatc gagattacat gcgtgtactg taaaaccgtc       600
ctggagctga cagaagtgtt cgagtttgct ttcaaggacc tgtttgtggt ctaccgggat       660
tcaatccctc acgcagccca taaaatcgac ttctacagca ggatcaggga actgcgccac       720
tactccgaca gcgtgtacgg ggatacactg gagaagctga caaacactgg cctgtacaat       780
```

| | |
|---|---|
| ctgctgatcc gactgcgaca gaagccactg aacccagccg aaaaactgag acacctgaac | 840 |
| gagaagagac ggtttcacaa tattgcaggc cattataggg gacagtgcca tagttgctgt | 900 |
| aatcgagcca ggcaggaaag actgcagcgc cgaagggaga ctcaagtcgg cggaggagga | 960 |
| ggagctgcat acatgcacgg cgacacccc acactgcatg aatatatgct ggatctgcag | 1020 |
| cctgagacta ccgacctgta ccagctgaac gattctagtg aggaagagga cgaaatcgac | 1080 |
| ggaccagcag gacaggcaga gcctgaccgg gcccactata atattgtgac attctgctgt | 1140 |
| aagtgcgatt ctactctgcg gctgtgcgtg cagagtactc atgtcgacat ccgcaccctg | 1200 |
| gaggatctgc tgatggggac tctgggcatc gtcccaattt gtagccagaa accaggcggc | 1260 |
| ggcggcggag cagcttacat gcacggaccc aaggctaccc tgcaggacat cgtgctgcat | 1320 |
| ctggaacctc agaatgagat tccagtcgac ctgctgcagc tgagtgattc agaagaggaa | 1380 |
| aacgacgaga tcgacggcgt gaatcaccag catctgcctg ctagacgggc agagccacag | 1440 |
| cgacacacaa tgctgtgcat gtgctgtaag tgtgaagcca ggatcaagct ggtggtcgag | 1500 |
| tcaagcgccg acgatctgcg cgccttccag cagctgttcc tgaatactct gtcatttgtc | 1560 |
| ccttggtgtg cctcccagca gtga | 1584 |

<210> SEQ ID NO 9
<211> LENGTH: 12754
<212> TYPE: DNA
<213> ORGANISM: Artificial Sequence
<220> FEATURE:
<223> OTHER INFORMATION: nucleotide encoding an artificial Maraba virus
      that expresses a human papilloma virus E6/E7 fusion protein

<400> SEQUENCE: 9

```
acgaagacaa acaaaccatt gatagaatta agaggctcat gaaaatcctt aacagcgttc     60
aaaatgtctg ttacagtcaa gagagtcatt gatgattcac tcatcacccc caaattgcct    120
gcgaatgagg accctgtgga gtaccctgct gattatttca aaaagtcccg tgatattccg    180
gtgtacataa acacgaccaa aagtttgtct gatttgcggg gctatgttta tcaaggccta    240
aagtcaggca acatctctat aattcatgtc aacagttatc tgtatgcagc attaaaagag    300
atcagaggaa aattggacag agattggatc acctttggta tccaaatcgg aaaaacagga    360
gatagcgtgg ggatattcga tttactgacc ctaaaacctc tagatggtgt tttaccagat    420
ggggtgtctg atgctactcg aactagctca gacgatgcat ggcttccact gtatctattg    480
gggttataca gagttggtcg aacacagatg ccagaataca ggaagaagct gatggatggt    540
ctgattaatc aatgtaagat gatcaatgag cagtttgaac cactgttgcc agaaggaaga    600
gatgtctttg atgtctgggg aaatgacagc aattacacaa agattgtggc cgctgtagat    660
atgttcttcc atatgttcaa aaagcatgag aaggcctctt tcaggtatgg cacaatagtg    720
tcaagattta aggattgtgc agcattggct acatttggtc atctgtgtaa gatcactggt    780
atgtccactg aagatgtgac aacttggatt ctaaacaggg aggtggctga tgagatggtt    840
caaatgatgt acccaggaca ggagatagat aaggctgatt cttacatgcc ttatctaatc    900
gacttaggtc tgtcctcaaa atctccatat tcatcagtta aaaatccagc tttccatttt    960
tggggtcaat tgaccgcatt gttactgaga tcaaccagag ccagaaatgc acgtcagccg   1020
gatgacatcg agtatacatc cctgaccact gctgggctgt tgtatgcata tgccgttggt   1080
tcgtctgcag acctggctca acaattctac gttggggaca acaagtatgt gccagaaact   1140
ggagatggag gattaaccac caatgcaccg ccacaagggc gagatgtggt cgagtggctt   1200
```

-continued

```
agttggtttg aagatcaaaa cagaaaacct accccagaca tgctcatgta tgctaagaga    1260
gctgtcagtg ctttacaagg attgagggag aagacgattg gcaagtacgc caagtcagag    1320
tttgacaaat gacaactcac tcaccatatg tattactacc tttgcttcat atgaaaaaaa    1380
ctaacagcga tcatggatca gctatcaaag gtcaaggaat tccttaagac ttacgcgcag    1440
ttggatcaag cagtacaaga gatggatgac attgagtctc agagagagga aaagactaat    1500
tttgatttgt ttcaggaaga aggattggag attaaggaga agccttccta ttatcgggca    1560
gatgaagaag agattgattc agatgaagac agcgtggatg atgcacaaga cttagggata    1620
cgtacatcaa caagtcccat cgaggggtat gtggatgagg agcaggatga ttatgaggat    1680
gaggaagtga acgtggtgtt tacatcggac tggaaacagc ctgagctgga atccgacggg    1740
gatgggaaaa ctctccgatt gacgatacca gatggattga ctggggagca gaagtcgcaa    1800
tggcttgcca cgattaaggc agttgttcag agtgctaaat attggaacat ctcagaatgt    1860
tcatttgaga gttatgagca aggggttttg attagagaga gacaaatgac tcctgatgtc    1920
tacaaagtca ctcctgtttt aaatgctcca ccggttcaaa tgacagctaa tcaagatgtt    1980
tggtctctca gcagcactcc atttacattt ttgcccaaga acaaggtgt gactccattg     2040 accatgtcct tagaagaact cttcaacacc cgaggtaat tcatatctct gggaggaaac     2100
gggaaaatga gtcaccggga ggccatcatt ctagggttga gacacaagaa gctctataat    2160
caagccagac taaagtataa cttagcttga atatgaaaa actaacaga tatcaaaga     2220 tatctctaac tcagtccatt gtgttcagtt caatcatgag ctctctcaag aaaattttgg    2280
gtattaaagg gaaagggaag aaatctaaga aattaggtat ggctcccca ccctatgaag    2340 aagagactcc aatggaatat tctccaagtg caccttatga taagtcattg tttggagtcg    2400
aagatatgga tttccatgat caacgtcaac tccgatatga gaaatttcac ttctcattga    2460
agatgactgt gagatcaaac aaaccatttc gaaattatga tgacgttgca gcagcggtgt    2520
ccaattggga tcatatgtac atcggcatgg caggaaaacg tccttttat aagatattag     2580 cattcatggg ttctactcta ttgaaggcta caccagccgt ctgggctgac caaggacagc    2640
cagaatatca tgctcactgt gagggacgag cttacttgcc gcatcggtta gggccgaccc    2700
ctccgatgtt gaatgtccct gaacatttc gccgtccatt taacatcgga ttattcagag    2760
ggacaatcga cataaccctg gtacttttcg atgatgaatc tgtagattct gccccggtca    2820
tatgggatca ttttaatgca tccagattga gcagcttcag agaaaaggct tgttgtttg    2880 gtttgattct agaaaagaaa gccactggga attgggtatt ggactctatt agtcatttca    2940
agtaattatc acaagtgttg aggtgatggg cagactatga aaaaaactaa cagggttcaa    3000
acactcttga tcgaggtacc cagtatatt tgttacaaca atgttgagac ttttctctt     3060 ttgtttcttg gccttaggag cccactccaa atttactata gtattccctc atcatcaaaa    3120
agggaattgg aagaatgtgc cttccacata tcattattgc ccttctagtt ctgaccagaa    3180
ttggcataat gatttgactg gagttagtct tcatgtgaaa attcccaaaa gtcacaaagc    3240
tatacaagca gatggctgga tgtgccacgc tgctaaatgg gtgactactt gtgacttcag    3300
atggtacgga cccaaataca tcacgcattc catacactct atgtcaccca ccctagaaca    3360
gtgcaagacc agtattgagc agacaaagca aggagtttgg attaatccag gctttccccc    3420
tcaaagctgc ggatatgcta cagtgacgga tgcagaggtg gttgttgtac aagcaacacc    3480
tcatcatgtg ttggttgatg agtacacagg agaatggatt gactcacaat ggtgggggg    3540 caaatgttcc aaggaggttt gtcaaacggt tcacaactcg accgtgtggc atgctgatta    3600
```

```
caagattaca gggctgtgcg agtcaaatct ggcatcagtg gatatcacct tcttctctga   3660
ggatggtcaa aagacgtctt tgggaaaacc gaacactgga ttcaggagta atcactttgc   3720
ttacgaaagt ggagagaagg catgccgtat gcagtactgc acacgatggg gaatccgact   3780
accttctgga gtatggtttg aattagtgga caaagatctc ttccaggcgg caaaattgcc   3840
tgaatgtcct agaggatcca gtatctcagc tccttctcag acttctgtgg atgttagttt   3900
gatacaagac gtagagagga tcttagatta ctctctatgc caggagacgt ggagtaagat   3960
acgagccaag cttcctgtat ctccagtaga tctgagttat ctcgccccaa aaaatccagg   4020
gagcggaccg gccttcacta tcattaatgg cactttgaaa tatttcgaaa caagatacat   4080
cagagttgac ataagtaatc ccatcatccc tcacatggtg gaacaatga gtggaaccac    4140 gactgagcgt gaattgtgga atgattggta tccatatgaa gacgtagaga ttggtccaaa   4200
tggggtgttg aaaactccca ctggtttcaa gtttccgctg tacatgattg ggcacggaat   4260
gttggattcc gatctccaca aatcctccca ggctcaagtc ttcgaacatc cacacgcaaa   4320
ggacgctgca tcacagcttc ctgatgatga gactttattt tttggtgaca caggactatc   4380
aaaaaaccca gtagagttag tagaaggctg gttcagtagc tggaagagca cattggcatc   4440
gttctttctg attataggct tgggggttgc attaatcttc atcattcgaa ttattgttgc   4500
gattcgctat aaatacaagg ggaggaagac ccaaaaaatt tacaatgatg tcgagatgag   4560
tcgattggga aataaataac agatgacgca tgagggtcag atcagattta cagcgtaagt   4620
gtgatattta ggattataaa ggttccttaa ttttaatttg ttacgcgttg tatgaaaaaa   4680
actcatcaac agccatcatg catcagaagc gaactgctat gtttcaggac cctcaggagc   4740
ggccacgcaa actgcctcag ctgtgcaccg aactgcagac aactatccac gacatcattc   4800
tggaatgcgt gtactgtaag cagcagctgc tgaggagaga ggtctatgac ttcgcttttc   4860
gcgatctgtg catcgtgtac cgagacgaa acccatatgc agtcgataag ctgaagttct   4920
acagcaagat ctccgaatac aggcattact gttacagcgt gtacgggacc acactggagc   4980
agcagtataa caagcccctg tgcgacctgc tgatcagaat taatcagaag cccctgtgcc   5040
ctgaggaaaa acagaggcac ctggataaga aacagagatt tcataacatc cgaggacgat   5100
ggaccgggcg gtgcatgtcc tgctgtagaa gctcccggac tcgacagaga acccagctgg   5160
gcggaggagg aggagcagct tacatggcac gattcgagga ccctacccga aggccatata   5220
agctgcccga cctgtgcaca gaactgaata cttctctgca ggacatcgag attacatgcg   5280
tgtactgtaa aaccgtcctg gagctgacag aagtgttcga gtttgctttc aaggacctgt   5340
ttgtggtcta ccgggattca atccctcacg cagcccataa aatcgacttc tacagcagga   5400
tcagggaact gcgccactac tccgacgcg tgtacgggga tacactggag aagctgacaa   5460
acactggcct gtacaatctg ctgatccgac tgcgacagaa gccactgaac ccagccgaaa   5520
aactgagaca cctgaacgag aagagacggt tcacaatat gcaggccat tatagggac     5580 agtgccatag ttgctgtaat cgagccaggc aggaaagact gcagcgccga agggagactc   5640
aagtcggcgg aggaggagga gctgcataca tgcacggcga cacccccaca ctgcatgaat   5700
atatgctgga tctgcagcct gagactaccg acctgtacca gctgaacgat tctagtgagg   5760
aagaggacga aatcgacgga ccagcaggac aggcagagcc tgaccgggcc cactataata   5820
ttgtgacatt ctgctgtaag tgcgattcta ctctgcggct gtgcgtgcag agtactcatg   5880
tcgacatccg caccctggag gatctgctga tgggactct gggcatcgtc ccaatttgta   5940
```

```
gccagaaacc aggcggcggc ggcggagcag cttacatgca cggacccaag gctaccctgc    6000
aggacatcgt gctgcatctg gaacctcaga atgagattcc agtcgacctg ctgcagctga    6060
gtgattcaga agaggaaaac gacgagatcg acggcgtgaa tcaccagcat ctgcctgcta    6120
gacgggcaga gccacagcga cacacaatgc tgtgcatgtg ctgtaagtgt gaagccagga    6180
tcaagctggt ggtcgagtca agcgccgacg atctgcgcgc cttccagcag ctgttcctga    6240
atactctgtc atttgtccct tggtgtgcct cccagcagtg acgtacgtgt atgaaaaaaa    6300
ctcatcaaca gccatcatgg atgttaacga ttttgagttg catgaggact ttgcattgtc    6360
tgaagatgac tttgtcactt cagaatttct caatccggaa gaccaaatga catacctgaa    6420
tcatgccgat tataatttga attctccctt aatcagcgat gatattgatt tcctgatcaa    6480
gaaatataat catgagcaaa ttccgaaaat gtgggatgtc aagaattggg agggagtgtt    6540
agagatgttg acagcctgtc aagccagtcc aattttatct agcactatgc ataagtgggt    6600
gggaaagtgg ctcatgtctg atgatcatga cgcaagccaa ggcttcagtt ttcttcatga    6660
agtggacaaa gaagctgatc tgacgtttga ggtggtggag acattcatta gaggatgggg    6720
aggtcgagaa ttgcagtaca agaggaaaga cacatttccg gactccttta gagttgcagc    6780
ctcattgtgt caaaaattcc ttgatttgca caaactcact ctgataatga attcagtctc    6840
tgaagtcgaa cttaccaacc tagcaaagaa ttttaaagga aaaacagga aagcaaaaag    6900 cggaaatctg ataaccagat tgagggttcc cagtttaggt cctgcttttg tgactcaggg    6960
atgggtgtac atgaagaagt tggaaatgat tatggatcgg aattttttgt tgatgttgaa    7020
agacgttatc atcgggagga tgcagacgat cctgtccatg atctcaagag atgataatct    7080
cttctccgag tctgatatct ttactgtatt aaagatatac cggatagggg ataagatatt    7140
agaaaggcaa gggacaaagg gttacgactt gatcaaaatg attgagccta tttgtaactt    7200
aaagatgatg aatctggcac gtaaatatcg tcctctcatc cctacatttc ctcattttga    7260
aaaacatatt gctgactctg ttaaggaagg atcgaaaata gacaagggga ttgagtttat    7320
atatgatcac attatgtcaa tccctggtgt ggacttgacc ttagttattt acggatcatt    7380
tcggcactgg ggtcatcctt ttatcaacta ctatgagggc ttagagaagc tacacaagca    7440
ggttacaatg cccaagacta ttgacagaga atatgcagaa tgtcttgcta gtgatctggc    7500
aagaatcgtt cttcagcaac aattcaatga acataagaaa tggtttgttg atgtagataa    7560
agtcccacaa tcccatcctt tcaaaagcca tatgaaagag aatacttggc ctactgcagc    7620
ccaagttcag gattacggcg atcgctggca tcagctccca ctcatcaaat gcttcgaaat    7680
cccagatttg ttagatccat cgatcatcta ctcagacaaa agtcattcca tgaaccggtc    7740
tgaagtacta cgacatgtaa gacttacacc tcatgtgccc attccaagca ggaaagtatt    7800
gcagacaatg ttggagacta aggcaacaga ctggaaagag tttttaaaga aaattgacga    7860
agaggggtta gaggatgatg atcttgtcat aggactcaaa gggaaagaga gagaattaaa    7920
aattgcggga agattctttt ctttgatgtc ctggaagctc agagagtatt ttgtcatcac    7980
tgagtatttg attaagacgc actttgtccc gatgtttaaa gggttgacca tggcggatga    8040
cttgacagcg gtgataaaga agatgatgga cacatcttca ggacaaggct tagataatta    8100
tgaatccatt tgtatagcca accatattga ctatgagaag tggaacaatc atcaaagaaa    8160
agagtcgaac gggcccgtgt tcaaggtgat gggtcaattc ttgggatatc cacgtctgat    8220
tgagagaact catgaatttt ttgagaagag tctgatatat tacaatggac gaccagatct    8280
gatgcgggtt cgaggaaatt ctctagtcaa cgcctcatct ttaaatgtct gctgggaggg    8340
```

```
tcaagctggg ggattagaag gactgcgaca gaagggatgg agtattctaa atttgcttgt    8400
cattcagaga gaagcaaaaa taaggaacac cgccgtgaaa gtgctagctc aaggtgacaa    8460
tcaggtgata tgtactcagt ataaaacgaa gaaatcccgg aatgatattg agcttaaggc    8520
agctctaaca cagatggtat ctaataatga gatgattatg tctgcgatta aatcaggcac    8580
cgagaaactg ggtcttttga ttaatgatga tgagacaatg caatctgctg attacctcaa    8640
ttacgggaag gttcccattt tcagaggagt aatcagaggc cttgagacaa aaagatggtc    8700
tcgagtgacc tgtgtgacaa atgatcagat tccaacgtgt gcgaacatta tgagctctgt    8760
gtcaactaat gcattaactg tagcccattt tgccgagaat ccagtcaatg ccatcattca    8820
gtataactac tttggaacat tgcaaggct actgctgatg atgcatgacc ccgctctgag    8880
gatctctctg tatgaagtcc aatcaaaaat tccaggactt cacagtttga catttaaata    8940
ttctatgttg tatctggatc cttcgatagg aggagtctcc ggaatgtcac tctcgagatt    9000
cctcataaga tcatttccag atccagtgac agaaagtttg gcgttctgga aatttatcca    9060
ctctcatgca agaagcgatt cattaaagga gatatgtgca gttttttggaa atcctgaaat    9120 tgcaagattt cggctaactc atgtcgataa attggtggaa gacccaacct cattgaacat    9180
agctatggga atgagtcctg ctaatctatt aaagacagag gtaaaaaaat gtctactgga    9240
atcaaggcag agcatcaaga accagattgt aagagatgct actatttacc tacaccatga    9300
ggaagacaaa cttcgtagtt tcttatggtc cataacacca ctgttccctc ggttcttgag    9360
tgaattcaaa tctgggacat tcatcggagt agcagatggc ctgatcagct tatttcagaa    9420
ctctaggact attcgaaatt cttttaaaaa gcgttatcac agggaacttg atgatttaat    9480
aatcaagagc gaagtttcct cacttatgca tttgggtaag ctacatttga ggcgaggctc    9540
agttcgtatg tggacttgct cttctactca ggctgatctt ctccgattcc ggtcatgggg    9600
aagatctgtt ataggaacca cagtccctca tcccttagag atgttaggac aacattttaa    9660
aaaggagact ccttgcagtg cttgcaacat atccggatta gactatgtat ctgtccactg    9720
tccgaatggg attcatgacg tttttgaatc acgtggtcca ctccctgcat atttgggttc    9780
taaaacatcc gaatcaactt cgatcttgca gccgtgggag agagagagta aagtaccgtt    9840
gattaagcgt gccacaaggc ttcgtgatgc aatttcatgg tttgtgtctc ccgactctaa    9900
cttggcctca actatcctta agaacataaa tgcattaaca ggagaagaat ggtcaaagaa    9960
gcagcatgga tttaaaagga cgggatcggc gttacacagg ttctccacat ccaggatgag   10020
tcatggtggt tttgcttctc agagtacggc tgccttgact agattgatgg caactactga   10080
cactatgaga gatctgggag aacagaacta tgatttcctg tttcaggcga cattattgta   10140
tgctcaaata accacaactg tagtcaggaa tggatcattt catagctgca cggaccatta   10200
ccatataacc tgcaaatctt gtctgagggc cattgatgag attaccttgg attcagcgat   10260
ggaatatagc cctccagatg tatcatcagt tttacaatct tggaggaatg gagaaggctc   10320
ttggggacat gaagtgaaac aaatatacccc agttgaaggt gactggaggg gactatctcc   10380
tgttgaacaa tcttatcaag tcggacgctg tatcgggttt ctgttcggtg atctggcgta   10440
tagaaaatca tcccatgcag atgatagctc catgttccg ttatctatac aaaacaaagt   10500
cagaggaaga ggcttttttaa aagggcttat ggatgggtta atgagagcca gttgttgcca   10560
ggtgatccat cgtcgaagct tagcccatct gaagagaccg gctaatgcag tctatggagg   10620
gctgatttat ttgatagaca aattgagtgc atctgccccct ttctttcac tgacgagaca   10680
```

```
tggaccttta agggaagaat tagaaactgt tccacataag ataccgactt cttatcctac    10740
gagcaaccga gatatggggg tgatagttcg taattatttt aaatatcagt gcagactggt    10800
agaaaaaggt cggtacaaga cacattatcc tcaattgtgg cttttctcag atgtgctgtc    10860
cattgatttc ttaggacccc tgtctatatc ttcaactcta ttgggtattc tgtataaaca    10920
gacgttatct tctcgagaca aaatgagtt gagagaactc gctaacttgt cttcattgtt    10980
gagatcagga gaaggatggg aagatatcca tgtcaaattc ttctctaagg cactttact    11040 ctgccctgaa gagatccgac atgcgtgcaa atttgggatt gctaaggaat ccgctgtttt    11100
aagctattat cctccttggt ctcaagagtc ttatggaggc atcacctcga tccccgtata    11160
tttttcgacc aggaagtatc ccaaaatttt agatgtccct cctcgggttc aaacccatt     11220 ggtctcgggt ctacgattgg ggcaactccc tactggagca cattataaga ttaggagcat    11280
tgtaaagaac aagaaccttc gttatagaga tttccttagt tgtggggatg gatctggggg    11340
gatgaccgcg gcactattga gagaaaacag acaaagtagg ggaatcttca acagcctgtt    11400
agagttagcc ggatctctta tgagaggagc atctccagag cctccaagtg cactggagac    11460
gctcgggcaa gaacgatcta ggtgtgtgaa tggaagcaca tgttgggagt actcatctga    11520
cctaagccaa aaagagacat gggattactt cttaagattg aagagaggcc tgggtttgac    11580
cgtggactta atcaccatgg acatggaggt cagagaccct aatacaagtt tgatgataga    11640
aaagaacctc aaagtttatc tgcatcagat attagaacca actggtgtct taatatataa    11700
aacatacggg acccatattg cgacacaaac agataatatc ctgacgataa tcggtccttt    11760
ctttgagacg gttgacctag tccagtccga atacagcagc tcacaaacgt ccgaggtcta    11820
ttttgtagga cgaggcttgc gctctcatgt tgacgaaccc tgggtggact ggccatcctt    11880
aatggacaat tggagatcca tttatgcttt tcatgatcct actacagaat ttatcagagc    11940
aaaaaaagtc tgtgaaattg acagtcttat aggcattccg gctcaattca ttccagaccc    12000
atttgtaaat ctcgagacca tgctacagat agttggtgtt ccaacaggag tttcgcatgc    12060
cgcagctcta ttatcatcac aatatccaaa tcaattggtc acaacgtcaa tatttatat    12120 gacactcgtg tcttattata atgtaaacca tattcgaaga agcccaagc ctttctctcc     12180 tccgtctgat ggagtctcac agaacattgg ttcagccata gtcggactaa gttttggggt    12240
gagtttgatg gagaatgatc tcggattata caaacaggct ctaggtgcaa taaagacgtc    12300
attccctatt agatggtcct ctgtccagac caaggatggg tttacacaag aatggagaac    12360
taaaggaaac ggaattccta agattgtcg tctctcagac tctttggctc agataggaaa     12420
ctggatcaga gcgatggaat tggttaggaa caaaacgagg caatcaggat tttctgaaac    12480
cctatttgat caattctgcg gacttgcaga ccatcacctc aaatggcgga agttgggaaa    12540
cagaacagga attattgatt ggctaaataa tagaatttca tccattgaca aatccatctt    12600
ggtgaccaaa agtgatctgc atgacgagaa ctcatggagg gagtgaagat gtattcttcc    12660
acctctcatt gggtgatacc catatatgaa aaaactata agtactttaa actctctttg     12720 tttttaatg tatatctggt tttgttgttt ccgt                                 12754
```

<210> SEQ ID NO 10
<211> LENGTH: 341
<212> TYPE: PRT
<213> ORGANISM: Homo sapiens

<400> SEQUENCE: 10

Met Glu Ser Arg Lys Asp Ile Thr Asn Gln Glu Glu Leu Trp Lys Met

```
   1               5                  10                 15
Lys Pro Arg Arg Asn Leu Glu Glu Asp Asp Tyr Leu His Lys Asp Thr
                20                 25                 30

Gly Glu Thr Ser Met Leu Lys Arg Pro Val Leu Leu His Leu His Gln
                35                 40                 45

Thr Ala His Ala Asp Glu Phe Asp Cys Pro Ser Glu Leu Gln His Thr
 50                 55                 60

Gln Glu Leu Phe Pro Gln Trp His Leu Pro Ile Lys Ile Ala Ala Ile
 65                 70                 75                 80

Ile Ala Ser Leu Thr Phe Leu Tyr Thr Leu Leu Arg Glu Val Ile His
                85                 90                 95

Pro Leu Ala Thr Ser His Gln Gln Tyr Phe Tyr Lys Ile Pro Ile Leu
               100                105                110

Val Ile Asn Lys Val Leu Pro Met Val Ser Ile Thr Leu Leu Ala Leu
               115                120                125

Val Tyr Leu Pro Gly Val Ile Ala Ala Ile Val Gln Leu His Asn Gly
130                135                140

Thr Lys Tyr Lys Lys Phe Pro His Trp Leu Asp Lys Trp Met Leu Thr
145                150                155                160

Arg Lys Gln Phe Gly Leu Leu Ser Phe Phe Ala Val Leu His Ala
               165                170                175

Ile Tyr Ser Leu Ser Tyr Pro Met Arg Arg Ser Tyr Arg Tyr Lys Leu
               180                185                190

Leu Asn Trp Ala Tyr Gln Gln Val Gln Gln Asn Lys Glu Asp Ala Trp
               195                200                205

Ile Glu His Asp Val Trp Arg Met Glu Ile Tyr Val Ser Leu Gly Ile
210                215                220

Val Gly Leu Ala Ile Leu Ala Leu Leu Ala Val Thr Ser Ile Pro Ser
225                230                235                240

Val Ser Asp Ser Leu Thr Trp Arg Glu Phe His Tyr Ile Gln Ser Lys
               245                250                255

Leu Gly Ile Val Ser Leu Leu Leu Gly Thr Ile His Ala Leu Ile Phe
               260                265                270

Ala Trp Asn Lys Trp Ile Asp Ile Lys Gln Phe Val Trp Tyr Thr Pro
               275                280                285

Pro Thr Phe Met Ile Ala Val Phe Leu Pro Ile Val Val Leu Ile Phe
               290                295                300

Lys Ser Ile Leu Phe Leu Pro Cys Leu Arg Lys Ile Leu Lys Ile
305                310                315                320

Arg His Gly Trp Glu Asp Val Thr Lys Ile Asn Lys Thr Glu Ile Cys
               325                330                335

Ser Gln Leu Lys Leu
               340
```

<210> SEQ ID NO 11
<211> LENGTH: 1026
<212> TYPE: DNA
<213> ORGANISM: Homo sapiens

<400> SEQUENCE: 11
atggaatcac ggaaggacat cactaatcag gaggaactgt ggaaaatgaa gccaagaagg    60
aatctggaag aggacgacta tctgcacaag acaccggcg aaacaagtat gctgaaacga   120
ccagtgctgc tgcacctgca tcagactgct cacgcagacg agtttgattg ccctctgaa   180

```
ctgcagcaca cccaggagct gttcccacag tggcatctgc ccatcaagat tgccgctatc      240
attgcttcac tgacatttct gtacactctg ctgagagaag tgatccaccc cctggccacc      300
agccatcagc agtacttcta taagatccct atcctggtca tcaacaaggt cctgccaatg      360
gtgagcatca cactgctggc cctggtctac ctgcctggag tgatcgcagc cattgtccag      420
ctgcacaatg ggacaaagta taagaaattt ccacattggc tggataagtg gatgctgact      480
aggaaacagt tcggactgct gtccttcttt ttcgccgtgc tgcacgctat ctacagcctg      540
tcctatccca tgaggaggag ctaccggtat aagctgctga actgggctta ccagcaggtg      600
cagcagaaca aggaggacgc atggattgaa catgacgtgt ggcgcatgga aatctacgtg      660
agcctgggca ttgtcggact ggccatcctg gctctgctgg cagtgaccag tatcccttct      720
gtcagtgact cactgacatg gagagagttt cactacattc agagcaagct ggggatcgtg      780
tccctgctgc tgggcaccat ccatgcactg attttgcct ggaacaagtg gatcgatatc      840
aagcagttcg tgtggtatac tcccctacc tttatgattg ccgtcttcct gcccatcgtg      900
gtcctgatct tcaagtccat cctgttcctg ccttgtctgc ggaagaaaat cctgaaaatt      960
cggcacggat gggaggatgt caccaaaatc aataagactg aaatctgtag ccagctgaag     1020
ctttaa                                                               1026

<210> SEQ ID NO 12
<211> LENGTH: 12196
<212> TYPE: DNA
<213> ORGANISM: Artificial Sequence
<220> FEATURE:
<223> OTHER INFORMATION: nucleotide encoding an artificial Maraba virus
      that expresses a human Six-Transmembrane Epithelial Antigen of the
      Prostate protein

<400> SEQUENCE: 12
acgaagacaa acaaaccatt gatagaatta agaggctcat gaaaatcctt aacagcgttc       60
aaaatgtctg ttacagtcaa gagagtcatt gatgattcac tcatcacccc caaattgcct      120
gcgaatgagg accctgtgga gtaccctgct gattatttca aaaagtcccg tgatattccg      180
gtgtacataa acacgaccaa aagtttgtct gatttgcggg gctatgttta tcaaggccta      240
aagtcaggca acatctctat aattcatgtc aacagttatc tgtatgcagc attaaaagag      300
atcagaggaa aattggacag agattggatc acctttggta tccaaatcgg aaaaacagga      360
gatagcgtgg ggatattcga tttactgacc ctaaaaccct caga tggtgt tttaccagat      420 ggggtgtctg atgctactcg aactagctca gacgatgcat ggcttccact gtatctattg      480
gggttataca gagttggtcg aacacagatg ccagaataca ggaagaagct gatggatggt      540
ctgattaatc aatgtaagat gatcaatgag cagtttgaac cactgttgcc agaaggaaga      600
gatgtctttg atgtctgggg aaatgacagc aattacacaa agattgtggc cgctgtagat      660
atgttcttcc atatgttcaa aaagcatgag aaggcctctt tcaggtatgg cacaatagtg      720
tcaagattta aggattgtgc agcattggct acatttggtc atctgtgtaa gatcactggt      780
atgtccactg aagatgtgac aacttggatt ctaaacaggg aggtggctga tgagatggtt      840
caaatgatgt acccaggaca ggagatagat aaggctgatt cttacatgcc ttatctaatc      900
gacttaggtc tgtcctcaaa atctccatat tcatcagtta aaaatccagc tttccatttt      960
tggggtcaat tgaccgcatt gttactgaga tcaaccagag ccagaaatgc acgtcagccg     1020
gatgacatcg agtatacatc cctgaccact gctgggctgt tgtatgcata tgccgttggt     1080
tcgtctgcag acctggctca acaattctac gttggggaca caagtatgt gccagaaact     1140
```

```
ggagatggag gattaaccac caatgcaccg ccacaagggc gagatgtggt cgagtggctt    1200
agttggtttg aagatcaaaa cagaaaacct accccagaca tgctcatgta tgctaagaga    1260
gctgtcagtg ctttacaagg attgagggag aagacgattg gcaagtacgc caagtcagag    1320
tttgacaaat gacaactcac tcaccatatg tattactacc tttgcttcat atgaaaaaaa    1380
ctaacagcga tcatggatca gctatcaaag gtcaaggaat tccttaagac ttacgcgcag    1440
ttggatcaag cagtacaaga gatggatgac attgagtctc agagagagga aaagactaat    1500
tttgatttgt ttcaggaaga aggattggag attaaggaga agccttccta ttatcgggca    1560
gatgaagaag agattgattc agatgaagac agcgtggatg atgcacaaga cttaggcata    1620
cgtacatcaa caagtcccat cgaggggtat gtggatgagg agcaggatga ttatgaggat    1680
gaggaagtga acgtggtgtt tacatcggac tggaaacagc ctgagctgga atccgacggg    1740
gatgggaaaa ctctccgatt gacgatacca gatggattga ctggggagca gaagtcgcaa    1800
tggcttgcca cgattaaggc agttgttcag agtgctaaat attggaacat ctcagaatgt    1860
tcatttgaga gttatgagca aggggttttg attagagaga gacaaatgac tcctgatgtc    1920
tacaaagtca ctcctgtttt aaatgctcca ccggttcaaa tgacagctaa tcaagatgtt    1980
tggtctctca gcagcactcc atttacattt ttgcccaaga aacaaggtgt gactccattg    2040
accatgtcct tagaagaact cttcaacacc cgaggtgaat tcatatctct gggaggaaac    2100
gggaaaatga gtcaccggga ggccatcatt ctagggttga gacacaagaa gctctataat    2160
caagccagac taaagtataa cttagcttga atatgaaaaa actaacaga tatcaaaaga     2220 tatctctaac tcagtccatt gtgttcagtt caatcatgag ctctctcaag aaaattttgg    2280
gtattaaagg gaaagggaag aaatctaaga aattaggtat ggctccccca ccctatgaag    2340
aagagactcc aatggaatat tctccaagtg caccttatga taagtcattg tttggagtcg    2400
aagatatgga tttccatgat caacgtcaac tccgatatga gaaatttcac ttctcattga    2460
agatgactgt gagatcaaac aaaccatttc gaaattatga tgacgttgca gcagcggtgt    2520
ccaattggga tcatatgtac atcggcatgc aggaaaaacg tccttttat aagatattag     2580 cattcatggg ttctactcta ttgaaggcta caccagccgt ctgggctgac caaggacagc    2640
cagaatatca tgctcactgt gagggacgag cttacttgcc gcatcggtta gggccgaccc    2700
ctccgatgtt gaatgtccct gaacattttc gccgtccatt taacatcgga ttattcagag    2760
ggacaatcga cataaccctg gtacttttcg atgatgaatc tgtagattct gccccggtca    2820
tatgggatca ttttaatgca tccagattga gcagcttcag agaaaaggct ttgttgtttg    2880
gtttgattct agaaaagaaa gccactggga attgggtatt ggactctatt agtcatttca    2940
agtaattatc acaagtgttg aggtgatggg cagactatga aaaaaactaa cagggttcaa    3000
acactcttga tcgaggtacc cagttatatt tgttacaaca atgttgagac ttttttctctt    3060 ttgtttcttg gccttaggag cccactccaa atttactata gtattccctc atcatcaaaa    3120
agggaattgg aagaatgtgc cttccacata tcattattgc ccttctagtt ctgaccagaa    3180
ttggcataat gatttgactg gagttagtct tcatgtgaaa attcccaaaa gtcacaaagc    3240
tatacaagca gatggctgga tgtgccacgc tgctaaatgg gtgactactt gtgacttcag    3300
atggtacgga cccaaataca tcacgcattc catacactct atgtcaccca ccctagaaca    3360
gtgcaagacc agtattgagc agacaaagca aggagtttgg attaatccag ctttccccc     3420 tcaaagctgc ggatatgcta cagtgacgga tgcagaggtg gttgttgtac aagcaacacc    3480
```

```
tcatcatgtg ttggttgatg agtacacagg agaatggatt gactcacaat tggtggggg      3540
caaatgttcc aaggaggttt gtcaaacggt tcacaactcg accgtgtggc atgctgatta      3600
caagattaca gggctgtgcg agtcaaatct ggcatcagtg gatatcacct tcttctctga      3660
ggatggtcaa aagacgtctt tgggaaaacc gaacactgga ttcaggagta atcactttgc      3720
ttacgaaagt ggagagaagg catgccgtat gcagtactgc acacgatggg gaatccgact      3780
accttctgga gtatggtttg aattagtgga caaagatctc ttccaggcgg caaaattgcc      3840
tgaatgtcct agaggatcca gtatctcagc tccttctcag acttctgtgg atgttagttt      3900
gatacaagac gtagagagga tcttagatta ctctctatgc caggagacgt ggagtaagat      3960
acgagccaag cttcctgtat ctccagtaga tctgagttat ctcgcccaa aaaatccagg       4020
gagcggaccg gccttcacta tcattaatgg cactttgaaa tatttcgaaa caagatacat      4080
cagagttgac ataagtaatc ccatcatccc tcacatggtg ggaacaatga gtggaaccac      4140
gactgagcgt gaattgtgga atgattggta tccatatgaa gacgtagaga ttggtccaaa      4200
tggggtgttg aaaactccca ctggttttcaa gtttccgctg tacatgattg ggcacggaat      4260
gttggattcc gatctccaca aatcctccca ggctcaagtc ttcgaacatc cacacgcaaa      4320
ggacgctgca tcacagcttc ctgatgatga actttatttt tttggtgaca caggactatc      4380
aaaaaaccca gtagagttag tagaaggctg gttcagtagc tggaagagca cattggcatc      4440
gttctttctg attataggct tggggggttgc attaatcttc atcattcgaa ttattgttgc      4500
gattcgctat aaatacaagg ggaggaagac ccaaaaaatt tacaatgatg tcgagatgag      4560
tcgattggga aataaataac agatgacgca tgagggtcag atcagattta cagcgtaagt      4620
gtgatattta ggattataaa ggttccttaa ttttaatttg ttacgcgttg tatgaaaaaa      4680
actcatcaac agccatcatg gaatcacgga aggacatcac taatcaggag gaactgtgga      4740
aaatgaagcc aagaaggaat ctggaagagg acgactatct gcacaaggac accggcgaaa      4800
caagtatgct gaaacgacca gtgctgctgc acctgcatca gactgctcac gcagacgagt      4860
ttgattgccc ctctgaactg cagcacaccc aggagctgtt cccacagtgg catctgccca      4920
tcaagattgc cgctatcatt gcttcactga catttctgta cactctgctg agagaagtga      4980
tccacccct ggccaccagc catcagcagt acttctataa gatccctatc ctggtcatca      5040
acaaggtcct gccaatggtg agcatcacac tgctggccct ggtctacctg cctggagtga      5100
tcgcagccat tgtccagctg cacaatggga caaagtataa gaaatttcca cattggctgg      5160
ataagtggat gctgactagg aaacagttcg gactgctgtc cttctttttc gccgtgctgc      5220
acgctatcta cagcctgtcc tatccatga ggaggagcta ccggtataag ctgctgaact       5280
gggcttacca gcaggtgcag cagaacaagg aggacgcatg gattgaacat gacgtgtggc      5340
gcatggaaat ctacgtgagc ctgggcattg tcggactggc catcctggct ctgctggcag      5400
tgaccagtat cccttctgtc agtgactcac tgacatggag agagtttcac tacattcaga      5460
gcaagctggg gatcgtgtcc ctgctgctgg gcaccatcca tgcactgatt tttgcctgga      5520
acaagtggat cgatatcaag cagttcgtgt ggtatactcc ccctaccttt atgattgccg      5580
tcttcctgcc catcgtggtc ctgatcttca gtccatcct gttcctgcct tgtctgcgga       5640
agaaaatcct gaaaattcgg cacggatggg aggatgtcac caaaatcaat aagactgaaa      5700
tctgtagcca gctgaagctt taacgtacgt gtatgaaaaa aactcatcaa cagccatcat      5760
ggatgttaac gattttgagt tgcatgagga ctttgcattg tctgaagatg actttgtcac      5820
ttcagaattt ctcaatccgg aagaccaaat gacatacctg aatcatgccg attataattt      5880
```

```
gaattctccc ttaatcagcg atgatattga tttcctgatc aagaaatata atcatgagca    5940
aattccgaaa atgtgggatg tcaagaattg ggagggagtg ttagagatgt tgacagcctg    6000
tcaagccagt ccaatttat ctagcactat gcataagtgg gtgggaaagt ggctcatgtc     6060
tgatgatcat gacgcaagcc aaggcttcag ttttcttcat gaagtggaca agaagctga    6120
tctgacgttt gaggtggtgg agacattcat tagaggatgg ggaggtcgag aattgcagta    6180
caagaggaaa gacacatttc cggactcctt tagagttgca gcctcattgt gtcaaaaatt    6240
ccttgatttg cacaaactca ctctgataat gaattcagtc tctgaagtcg aacttaccaa    6300
cctagcaaag aattttaaag gaaaaaacag gaaagcaaaa agcggaaatc tgataaccag    6360
attgagggtt cccagtttag gtcctgcttt tgtgactcag ggatgggtgt acatgaagaa    6420
gttgaaaatg attatggatc ggaattttt gttgatgttg aaagacgtta tcatcgggag     6480
gatgcagacg atcctgtcca tgatctcaag agatgataat ctcttctccg agtctgatat    6540
ctttactgta ttaaagatat accggatagg ggataagata ttagaaaggc aagggacaaa    6600
gggttacgac ttgatcaaaa tgattgagcc tatttgtaac ttaaagatga tgaatctggc    6660
acgtaaatat cgtcctctca tccctacatt tcctcatttt gaaaaacata ttgctgactc    6720
tgttaaggaa ggatcgaaaa tagacaaagg gattgagttt atatatgatc acattatgtc    6780
aatccctggt gtggacttga ccttagttat ttacggatca tttcggcact ggggtcatcc    6840
ttttatcaac tactatgagg gcttagagaa gctacacaag caggttacaa tgcccaagac    6900
tattgacaga gaatatgcag aatgtcttgc tagtgatctg gcaagaatcg ttcttcagca    6960
acaattcaat gaacataaga aatggtttgt tgatgtagat aaagtcccac aatcccatcc    7020
tttcaaaagc catatgaaag agaatacttg gcctactgca gcccaagttc aggattacgg    7080
cgatcgctgg catcagctcc cactcatcaa atgcttcgaa atcccagatt tgttagatcc    7140
atcgatcatc tactcagaca aaagtcattc catgaaccgg tctgaagtac tacgacatgt    7200
aagacttaca cctcatgtgc ccattccaag caggaaagta ttgcagacaa tgttggagac    7260
taaggcaaca gactggaaag agttttaaa gaaaattgac gaagaggggt tagaggatga    7320
tgatcttgtc ataggactca aagggaaaga gagagaatta aaaattgcgg gaagattctt    7380
ttctttgatg tcctggaagc tcagagagta ttttgtcatc actgagtatt tgattaagac    7440
gcactttgtc ccgatgttta aagggttgac catggcggat gacttgacag cggtgataaa    7500
gaagatgatg gacacatctt caggacaagg cttagataat tatgaatcca tttgtatagc    7560
caaccatatt gactatgaga gtggaacaa tcatcaaaga aaagagtcga acgggcccgt     7620
gttcaaggtg atgggtcaat tcttgggata tccacgtctg attgagagaa ctcatgaatt    7680
ttttgagaag agtctgatat attacaatgg acgaccagat ctgatgcggg ttcgaggaaa    7740
ttctctagtc aacgcctcat ctttaaatgt ctgctgggag ggtcaagctg ggggattaga    7800
aggactgcga cagaagggat ggagtattct aaatttgctt gtcattcaga gagaagcaaa    7860
aataaggaac accgccgtga agtgctagc tcaaggtgac aatcaggtga tatgtactca    7920
gtataaaacg aagaaatccc ggaatgtat tgagcttaag gcagctctaa cacagatggt    7980
atctaataat gagatgatta tgtctgcgat taaatcaggc accgagaaac tgggtctttt    8040
gattaatgat gatgagacaa tgcaatctgc tgattacctc aattacggga aggttcccat    8100
tttcagagga gtaatcagag gccttgagac aaaaagatgg tctcgagtga cctgtgtgac    8160
aaatgatcag attccaacgt gtgcgaacat tatgagctct gtgtcaacta atgcattaac    8220
```

```
tgtagcccat tttgccgaga atccagtcaa tgccatcatt cagtataact actttggaac      8280
atttgcaagg ctactgctga tgatgcatga ccccgctctg aggatctctc tgtatgaagt      8340
ccaatcaaaa attccaggac ttcacagttt gacatttaaa tattctatgt tgtatctgga      8400
tccttcgata ggaggagtct ccggaatgtc actctcgaga ttcctcataa gatcatttcc      8460
agatccagtg acagaaagtt tggcgttctg gaaatttatc cactctcatg caagaagcga      8520
ttcattaaag gagatatgtg cagttttggg aaatcctgaa attgcaagat ttcggctaac      8580
tcatgtcgat aaattggtgg aagacccaac ctcattgaac atagctatgg gaatgagtcc      8640
tgctaatcta ttaaagacag aggtaaaaaa atgtctactg gaatcaaggc agagcatcaa      8700
gaaccagatt gtaagagatg ctactattta cctacaccat gaggaagaca aacttcgtag      8760
tttcttatgg tccataacac cactgttccc tcggttcttg agtgaattca atctgggac      8820 attcatcgga gtagcagatg gcctgatcag cttatttcag aactctagga ctattcgaaa      8880
ttcttttaaa aagcgttatc acagggaact tgatgattta ataatcaaga gcgaagtttc      8940
ctcacttatg catttgggta agctacattt gaggcgaggc tcagttcgta tgtggacttg      9000
ctcttctact caggctgatc ttctccgatt ccggtcatgg ggaagatctg ttataggaac      9060
cacagtccct catcccttag agatgttagg acaacatttt aaaaggaga ctccttgcag      9120 tgcttgcaac atatccggat tagactatgt atctgtccac tgtccgaatg ggattcatga      9180 cgttttgaa tcacgtggtc cactccctgc atatttgggt tctaaaacat ccgaatcaac      9240
ttcgatcttg cagccgtggg agagagagag taaagtaccg ttgattaagc gtgccacaag      9300
gcttcgtgat gcaatttcat ggtttgtgtc tcccgactct aacttggcct caactatcct      9360
taagaacata aatgcattaa caggagaaga atggtcaaag aagcagcatg gatttaaaag      9420
gacgggatcg gcgttacaca ggttctccac atccaggatg agtcatggtg gttttgcttc      9480
tcagagtacg gctgccttga ctagattgat ggcaactact gacactatga gagatctggg      9540
agaacagaac tatgatttcc tgtttcaggc gacattattg tatgctcaaa taaccacaac      9600
tgtagtcagg aatggatcat ttcatagctg cacggaccat taccatataa cctgcaaatc      9660
ttgtctgagg gccattgatg agattacctt ggattcagcg atggaatata gccctccaga      9720
tgtatcatca gttttacaat cttggaggaa tggagaaggc tcttggggac atgaagtgaa      9780
acaaatatac ccagttgaag gtgactggag gggactatct cctgttgaac aatcttatca      9840
agtcggacgc tgtatcgggt ttctgttcgg tgatctggcg tatagaaaat catcccatgc      9900
agatgatagc tccatgtttc cgttatctat acaaaacaaa gtcagaggaa gaggcttttt      9960
aaaagggctt atggatgggt taatgagagc cagttgttgc caggtgatcc atcgtcgaag     10020
cttagcccat ctgaagagac cggctaatgc agtctatgga gggctgattt atttgataga     10080
caaattgagt gcatctgccc ctttctttc actgacgaga catggacctt aagggaaga     10140 attagaaact gttccacata agataccgac ttcttatcct acgagcaacc gagatatggg     10200
ggtgatagtt cgtaattatt ttaaatatca gtgcagactg gtagaaaaag gtcggtacaa     10260
gacacattat cctcaattgt ggcttttctc agatgtgctg tccattgatt tcttaggacc     10320
cctgtctata tcttcaactc tattgggtat tctgtataaa cagacgttat cttctcgaga     10380
caaaaatgag ttgagagaac tcgctaactt gtcttcattg ttgagatcag gagaaggatg     10440
ggaagatatc catgtcaaat tcttctctaa ggacacttta ctctgccctg aagagatccg     10500
acatgcgtgc aaatttggga ttgctaagga atccgctgtt ttaagctatt atcctccttg     10560
gtctcaagag tcttatggag gcatcacctc gatccccgta tatttttcga ccaggaagta     10620
```

-continued

```
tcccaaaatt ttagatgtcc ctcctcgggt tcaaaaccca ttggtctcgg gtctacgatt    10680
ggggcaactc cctactggag cacattataa gattaggagc attgtaaaga acaagaacct    10740
tcgttataga gatttcctta gttgtgggga tggatctggg gggatgaccg cggcactatt    10800
gagagaaaac agacaaagta gggaatcttc aacagcctg ttagagttag ccggatctct     10860
tatgagagga gcatctccag agcctccaag tgcactggag acgctcgggc aagaacgatc    10920
taggtgtgtg aatggaagca catgttggga gtactcatct gacctaagcc aaaagagac     10980
atgggattac ttcttaagat tgaagagagg cctgggtttg accgtggact taatcaccat    11040
ggacatggag gtcagagacc ctaatacaag tttgatgata gaaagaaacc tcaaagttta    11100
tctgcatcag atattagaac caactggtgt cttaatatat aaaacatacg ggacccatat    11160
tgcgacacaa acagataata tcctgacgat aatcggtcct ttctttgaga cggttgacct    11220
agtccagtcc gaatacagca gctcacaaac gtccgaggtc tattttgtag gacgaggctt    11280
gcgctctcat gttgacgaac cctgggtgga ctggccatcc ttaatggaca attggagatc    11340
catttatgct tttcatgatc ctactacaga atttatcaga gcaaaaaag tctgtgaaat     11400
tgacagtctt ataggcattc cggctcaatt cattccagac ccatttgtaa atctcgagac    11460
catgctacag atagttggtg ttccaacagg agtttcgcat gccgcagctc tattatcatc    11520
acaatatcca atcaattgg tcacaacgtc aatattttat atgacactcg tgtcttatta     11580
taatgtaaac catattcgaa gaagccccaa gcctttctct cctccgtctg atggagtctc    11640
acagaacatt ggttcagcca tagtcggact aagttttttgg gtgagtttga tggagaatga    11700
tctcggatta tacaaacagg ctctaggtgc aataaagacg tcattcccta ttagatggtc    11760
ctctgtccag accaaggatg ggtttacaca agaatggaga actaaaggaa acggaattcc    11820
taaagattgt cgtctctcag actctttggc tcagatagga aactggatca gagcgatgga    11880
attggttagg aacaaaacga ggcaatcagg attttctgaa accctatttg atcaattctg    11940
cggacttgca gaccatcacc tcaaatggcg gaagttggga aacagaacag gaattattga    12000
ttggctaaat aatagaattt catccattga caaatccatc ttggtgacca aaagtgatct    12060
gcatgacgag aactcatgga gggagtgaag atgtattctt ccacctctca ttgggtgata    12120
cccatatatg aaaaaaacta aagtactttt aaactctctt tgttttttaa tgtatatctg    12180
gttttgttgt ttccgt                                                    12196
```

<210> SEQ ID NO 13
<211> LENGTH: 180
<212> TYPE: PRT
<213> ORGANISM: Homo sapiens

<400> SEQUENCE: 13

Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
            20                  25                  30

Gly Pro Gly Glu Ala Gly Ala Thr Gly Gly Arg Gly Pro Arg Gly Ala
        35                  40                  45

Gly Ala Ala Arg Ala Ser Gly Pro Gly Gly Gly Ala Pro Arg Gly Pro
    50                  55                  60

His Gly Gly Ala Ala Ser Gly Leu Asn Gly Cys Cys Arg Cys Gly Ala
65                  70                  75                  80

Arg Gly Pro Glu Ser Arg Leu Leu Glu Phe Tyr Leu Ala Met Pro Phe

```
                    85                  90                  95
Ala Thr Pro Met Glu Ala Glu Leu Ala Arg Arg Ser Leu Ala Gln Asp
                100                 105                 110

Ala Pro Pro Leu Pro Val Pro Gly Val Leu Leu Lys Glu Phe Thr Val
            115                 120                 125

Ser Gly Asn Ile Leu Thr Ile Arg Leu Thr Ala Ala Asp His Arg Gln
        130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Pro Pro Ser
                165                 170                 175

Gly Gln Arg Arg
            180

<210> SEQ ID NO 14
<211> LENGTH: 543
<212> TYPE: DNA
<213> ORGANISM: Homo sapiens

<400> SEQUENCE: 14
atgcaggccg agggcagagg cacaggcgga tctacaggcg acgccgatgg ccctggcggc    60
cctggaattc ctgacggacc tggcggcaat gccggcggac ccggagaagc tggcgccaca   120 ggcggaaagag gacctagagg cgctggcgcc gctagagctt ctggaccagg cggaggcgcc   180
cctagaggac ctcatggcgg agccgcctcc ggcctgaacg ctgttgcag atgtggagcc    240 agaggccccg agagccggct gctggaattc tacctggcca tgcccttcgc caccccatg    300 gaagccgagc tggccagacg gtccctggcc aggatgctc tcctctgcc tgtgccggc     360 gtgctgctga agaattcac cgtgtccggc aacatcctga ccatccggct gactgccgcc   420
gaccacagac agctccagct gtctatcagc tcctgcctgc agcagctgag cctgctgatg   480
tggatcaccc agtgctttct gcccgtgttc ctggctcagc cccccagcgg ccagagaaga   540
tga                                                                  543

<210> SEQ ID NO 15
<211> LENGTH: 11725
<212> TYPE: DNA
<213> ORGANISM: Artificial Sequence
<220> FEATURE:
<223> OTHER INFORMATION: nucleotide encoding an artificial Maraba virus
      that expresses a human Cancer Testis Antigen 1 protein

<400> SEQUENCE: 15
acgaagacaa acaaaccatt gatagaatta agaggctcat gaaaatcctt aacagcgttc    60
aaaatgtctg ttacagtcaa gagagtcatt gatgattcac tcatcacccc caaattgcct   120
gcgaatgagg accctgtgga gtaccctgct gattatttca aaaagtcccg tgatattccg   180
gtgtacataa acacgaccaa agtttgtct gatttgcggg ctatgtttta tcaaggccta   240
aagtcaggca catctctat aattcatgtc aacagttatc tgtatgcagc attaaaagag   300
atcagaggaa aattggacag agattggatc acctttggta tccaaatcgg aaaaacagga   360
gatagcgtgg ggatattcga tttactgacc ctaaaacctc tagatggtgt tttaccagat   420 gggggtgtctg atgctactcg aactagctca gacgatgcat ggcttccact gtatctattg   480
gggttataca gagttggtcg aacacagatg ccagaataca ggaagaagct gatggatggt   540
ctgattaatc aatgtaagat gatcaatgag cagtttgaac cactgttgcc agaaggaaga   600
```

```
gatgtctttg atgtctgggg aaatgacagc aattacacaa agattgtggc cgctgtagat    660
atgttcttcc atatgttcaa aaagcatgag aaggcctctt tcaggtatgg cacaatagtg    720
tcaagattta aggattgtgc agcattggct acatttggtc atctgtgtaa gatcactggt    780
atgtccactg aagatgtgac aacttggatt ctaaacaggg aggtggctga tgagatggtt    840
caaatgatgt acccaggaca ggagatagat aaggctgatt cttacatgcc ttatctaatc    900
gacttaggtc tgtcctcaaa atctccatat tcatcagtta aaaatccagc tttccatttt    960
tggggtcaat tgaccgcatt gttactgaga tcaaccagag ccagaaatgc acgtcagccg   1020
gatgacatcg agtatacatc cctgaccact gctgggctgt tgtatgcata tgccgttggt   1080
tcgtctgcag acctggctca acaattctac gttggggaca caagtatgt gccagaaact    1140
ggagatggag gattaaccac caatgcaccg ccacaagggc gagatgtggt cgagtggctt   1200
agttggtttg aagatcaaaa cagaaaacct accccagaca tgctcatgta tgctaagaga   1260
gctgtcagtg ctttacaagg attgagggag aagacgattg gcaagtacgc caagtcagag   1320
tttgacaaat gacaactcac tcaccatatg tattactacc tttgcttcat atgaaaaaaa   1380
ctaacagcga tcatggatca gctatcaaag gtcaaggaat tccttaagac ttacgcgcag   1440
ttggatcaag cagtacaaga gatggatgac attgagtctc agagagagga aaagactaat   1500
tttgatttgt tcaggaaga aggattggag attaaggaga agccttccta ttatcgggca    1560
gatgaagaag agattgattc agatgaagac agcgtggatg atgcacaaga cttaggata    1620
cgtacatcaa caagtcccat cgaggggtat gtggatgagg agcaggatga ttatgaggat   1680
gaggaagtga acgtggtgtt tacatcggac tggaaacagc ctgagctgga atccgacggg   1740
gatgggaaaa ctctccgatt gacgatacca gatggattga ctggggagca gaagtcgcaa   1800
tggcttgcca cgattaaggc agttgttcag agtgctaaat attggaacat ctcagaatgt   1860
tcatttgaga gttatgagca agggttttg attagagaga cacaaatgac tcctgatgtc    1920
tacaaagtca ctcctgtttt aaatgctcca ccggttcaaa tgacagctaa tcaagatgtt   1980
tggtctctca gcagcactcc atttacattt ttgcccaaga acaaggtgt gactccattg    2040
accatgtcct tagaagaact cttcaacacc cgaggtgaat tcatatctct gggaggaaac   2100
gggaaaatga gtcaccggga ggccatcatt ctagggttga gacacaagaa gctctataat   2160
caagccagac taaagtataa cttagcttga atatgaaaaa aactaacaga tatcaaaaga   2220
tatctctaac tcagtccatt gtgttcagtt caatcatgag ctctctcaag aaaattttgg   2280
gtattaaagg gaaagggaag aaatctaaga aattaggtat ggctccccca ccctatgaag   2340
aagagactcc aatggaatat tctccaagtg caccttatga taagtcattg tttggagtcg   2400
aagatatgga tttccatgat caacgtcaac tccgatatga gaaatttcac ttctcattga   2460
agatgactgt gagatcaaac aaaccatttc gaaattatga tgacgttgca gcagcggtgt   2520
ccaattggga tcatatgtac atcggcatgg caggaaaacg tccttttat aagatattag    2580
cattcatggg ttctactcta ttgaaggcta caccagccgt ctgggctgac caaggacagc   2640
cagaatatca tgctcactgt gagggacgag cttacttgcc gcatcggtta gggccgaccc   2700
ctccgatgtt gaatgtccct gaacattttc gccgtccatt taacatcgga ttattcagag   2760
ggacaatcga cataacctg gtacttttcg atgatgaatc tgtagattct gccccggtca    2820
tatgggatca ttttaatgca tccagattga gcagcttcag agaaaaggct tgttgtttg    2880
gtttgattct agaaaagaaa gccactggga attgggtatt ggactctatt agtcatttca   2940
agtaattatc acaagtgttg aggtgatggg cagactatga aaaaaactaa cagggttcaa   3000
```

```
acactcttga tcgaggtacc cagttatatt tgttacaaca atgttgagac ttttctctt      3060 ttgtttcttg gccttaggag cccactccaa atttactata gtattccctc atcatcaaaa      3120
agggaattgg aagaatgtgc cttccacata tcattattgc ccttctagtt ctgaccagaa      3180
ttggcataat gatttgactg gagttagtct tcatgtgaaa attcccaaaa gtcacaaagc      3240
tatacaagca gatggctgga tgtgccacgc tgctaaatgg gtgactactt gtgacttcag      3300
atggtacgga cccaaataca tcacgcattc catacactct atgtcaccca ccctagaaca      3360
gtgcaagacc agtattgagc agacaaagca aggagtttgg attaatccag ctttccccc       3420 tcaaagctgc ggatatgcta cagtgacgga tgcagaggtg gttgttgtac aagcaacacc      3480
tcatcatgtg ttggttgatg agtacacagg agaatggatt gactcacaat ggtgggggg       3540 caaatgttcc aaggaggttt gtcaaacggt tcacaactcg accgtgtggc atgctgatta      3600
caagattaca gggctgtgcg agtcaaatct ggcatcagtg gatatcacct tcttctctga      3660
ggatggtcaa aagacgtctt tgggaaaacc gaacactgga ttcaggagta atcactttgc      3720
ttacgaaagt ggagagaagg catgccgtat gcagtactgc acacgatggg gaatccgact      3780
accttctgga gtatggtttg aattagtgga caaagatctc ttccaggcgg caaaattgcc      3840
tgaatgtcct agaggatcca gtatctcagc tccttctcag acttctgtgg atgttagttt      3900
gatacaagac gtagagagga tcttagatta ctctctatgc caggagacgt ggagtaagat      3960
acgagccaag cttcctgtat ctccagtaga tctgagttat ctcgccccaa aaaatccagg      4020
gagcggaccg gccttcacta tcattaatgg cactttgaaa tatttcgaaa caagatacat      4080
cagagttgac ataagtaatc ccatcatccc tcacatggtg ggaacaatga gtggaaccac      4140
gactgagcgt gaattgtgga atgattggta tccatatgaa gacgtagaga ttggtccaaa      4200
tggggtgttg aaaactccca ctggtttcaa gtttccgctg tacatgattg ggcacggaat      4260
gttggattcc gatctccaca aatcctccca ggctcaagtc ttcgaacatc cacacgcaaa      4320
ggacgctgca tcacagcttc ctgatgatga gactttattt tttggtgaca caggactatc      4380
aaaaaaccca gtagagttag tagaaggctg gttcagtagc tggaagagca cattggcatc      4440
gttctttctg attataggct tggggttgc attaatcttc atcattcgaa ttattgttgc       4500
gattcgctat aaaatacaagg ggaggaagac ccaaaaaatt tacaatgatg tcgagatgag      4560
tcgattggga aataaataac agatgacgca tgagggtcag atcagattta cagcgtaagt      4620
gtgatattta ggattataaa ggttccttaa ttttaatttg ttacgcgttg tatgaaaaaa      4680
actcatcaac agccatcgcc accatgcagg ccgaggcag aggcacaggc ggatctacag       4740
gcgacgccga tggccctggc ggccctggaa ttcctgacgg acctggcggc aatgccggcg      4800
gacccggaga agctggcgcc acaggcgaa gaggacctag aggcgctggc gccgctagag       4860
cttctggacc aggcggaggc gcccctagag gacctcatgg cggagccgcc tccggcctga     4920
acggctgttg cagatgtgga gccagaggcc ccgagagccg gctgctgaa ttctacctgg       4980 ccatgccctt cgccaccccc atggaagccg agctggccag acggtccctg gcccaggatg     5040
ctcctcctct gcctgtgccc ggcgtgctgc tgaaagaatt caccgtgtcc ggcaacatcc      5100
tgaccatccg gctgactgcc gccgaccaca gacagctcca gctgtctatc agctcctgcc      5160
tgcagcagct gagcctgctg atgtggatca cccagtgctt tctgccgtg ttcctggctc       5220 agccccccag cggccagaga agatgagtcg acacgcgttg tatgaaaaaa actcatcaac      5280
agccatcatg gatgttaacg attttgagtt gcatgaggac tttgcattgt ctgaagatga      5340
```

```
ctttgtcact tcagaattttc tcaatccgga agaccaaatg acatacctga atcatgccga    5400
ttataaattg aattctccct taatcagcga tgatattgat ttcctgatca agaaatataa    5460
tcatgagcaa attccgaaaa tgtgggatgt caagaattgg gagggagtgt tagagatgtt    5520
gacagcctgt caagccagtc caattttatc tagcactatg cataagtggg tgggaaagtg    5580
gctcatgtct gatgatcatg acgcaagcca aggcttcagt tttcttcatg aagtggacaa    5640
agaagctgat ctgacgtttg aggtggtgga gacattcatt agaggatggg gaggtcgaga    5700
attgcagtac aagaggaaag acacatttcc ggactccttt agagttgcag cctcattgtg    5760
tcaaaaattc cttgatttgc acaaactcac tctgataatg aattcagtct ctgaagtcga    5820
acttaccaac ctagcaaaga atttttaaagg aaaaaacagg aaagcaaaaa gcggaaatct    5880
gataaccaga ttgagggttc ccagtttagg tcctgctttt gtgactcagg gatgggtgta    5940
catgaagaag ttggaaatga ttatggatcg gaattttttg ttgatgttga aagacgttat    6000
catcgggagg atgcagacga tcctgtccat gatctcaaga gatgataatc tcttctccga    6060
gtctgatatc tttactgtat taaagatata ccggataggg gataagatat tagaaaggca    6120
agggacaaag ggttacgact tgatcaaaat gattgagcct atttgtaact taaagatgat    6180
gaatctggca cgtaaatatc gtcctctcat ccctacattt cctcattttg aaaaacatat    6240
tgctgactct gttaaggaag gatcgaaaat agacaaaggg attgagttta tatatgatca    6300
cattatgtca atccctggtg tggacttgac cttagttatt tacgatcat ttcggcactg    6360 gggtcatcct tttatcaact actatgaggg cttagagaag ctacacaagc aggttacaat    6420
gcccaagact attgacagag aatatgcaga atgtcttgct agtgatctgg caagaatcgt    6480
tcttcagcaa caattcaatg aacataagaa atggtttgtt gatgtagata aagtcccaca    6540
atcccatcct ttcaaaagcc atatgaaaga gaatacttgg cctactgcag cccaagttca    6600
ggattacggc gatcgctggc atcagctccc actcatcaaa tgcttcgaaa tcccagattt    6660
gttagatcca tcgatcatct actcagacaa aagtcattcc atgaaccggt ctgaagtact    6720
acgacatgta agacttacac ctcatgtgcc cattccaagc aggaaagtat tgcagacaat    6780
gttggagact aaggcaacag actggaaaga gttttaaag aaaattgacg aagaggggtt    6840
agaggatgat gatcttgtca taggactcaa agggaaagag agagaattaa aaattgcggg    6900
aagattcttt tctttgatgt cctggaagct cagagagtat tttgtcatca ctgagtattt    6960
gattaagacg cactttgtcc cgatgtttaa agggttgacc atggcggatg acttgacagc    7020
ggtgataaag aagatgatgg acacatcttc aggacaaggc ttagataatt atgaatccat    7080
ttgtatagcc aaccatattg actatgagaa gtggaacaat catcaaagaa aagagtcgaa    7140
cgggcccgtg ttcaaggtga tgggtcaatt cttgggatat ccacgtctga ttgagagaac    7200
tcatgaattt tttgagaaga gtctgatata ttacaatgga cgaccagatc tgatgcgggt    7260
tcgaggaaat tctctagtca acgcctcatc tttaaatgtc tgctgggagg gtcaagctgg    7320
gggattagaa ggactgcgac agaagggatg gagtattcta aatttgcttg tcattcagag    7380
agaagcaaaa ataaggaaca ccgccgtgaa agtgctagct caaggtgaca atcaggtgat    7440
atgtactcag tataaaacga agaaatcccg gaatgatatt gagcttaagg cagctctaac    7500
acagatggta tctaataatg agatgattat gtctgcgatt aaatcaggca ccgagaaact    7560
gggtcttttg attaatgatg atgagacaat gcaatctgct gattacctca attacgggaa    7620
ggttcccatt ttcagaggag taatcagagg ccttgagaca aaaagatggt cacgcgtgac    7680
ctgtgtgaca aatgatcaga ttccaacgtg tgcgaacatt atgagctctg tgtcaactaa    7740
```

```
tgcattaact gtagcccatt ttgccgagaa tccagtcaat gccatcattc agtataacta    7800
ctttggaaca tttgcaaggc tactgctgat gatgcatgac cccgctctga ggatctctct    7860
gtatgaagtc caatcaaaaa ttccaggact tcacagtttg acatttaaat attctatgtt    7920
gtatctggat ccttcgatag gaggagtctc cggaatgtca ctctcgagat tcctcataag    7980
atcatttcca gatccagtga cagaaagttt ggcgttctgg aaatttatcc actctcatgc    8040
aagaagcgat tcattaaagg agatatgtgc agtttttgga aatcctgaaa ttgcaagatt    8100
tcggctaact catgtcgata aattggtgga agacccaacc tcattgaaca tagctatggg    8160
aatgagtcct gctaatctat aaagacaga ggtaaaaaaa tgtctactgg aatcaaggca    8220
gagcatcaag aaccagattg taagagatgc tactatttac ctacaccatg aggaagacaa    8280
acttcgtagt ttcttatggt ccataacacc actgttccct cggttcttga gtgaattcaa    8340
atctgggaca ttcatcggag tagcagatgg cctgatcagc ttatttcaga actctaggac    8400
tattcgaaat tcttttaaaa agcgttatca cagggaactt gatgatttaa taatcaagag    8460
cgaagtttcc tcacttatgc atttgggtaa gctacatttg aggcgaggct cagttcgtat    8520
gtggacttgc tcttctactc aggctgatct tctccgattc cggtcatggg gaagatctgt    8580
tataggaacc acagtccctc atcccttaga gatgttagga caacatttta aaaggagac    8640 tccttgcagt gcttgcaaca tatccggatt agactatgta tctgtccact gtccgaatgg    8700
gattcatgac gttttgaat cacgtggtcc actccctgca tatttgggtt ctaaaacatc    8760
cgaatcaact tcgatcttgc agccgtggga gagagagagt aaagtaccgt tgattaagcg    8820
tgccacaagg cttcgtgatg caatttcatg gtttgtgtct cccgactcta acttggcctc    8880
aactatcctt aagaacataa atgcattaac aggagaagaa tggtcaaaga agcagcatgg    8940
atttaaaagg acgggatcgg cgttacacag gttctccaca tccaggatga gtcatggtgg    9000
ttttgcttct cagagtacgg ctgccttgac tagattgatg gcaactactg acactatgag    9060
agatctggga gaacagaact atgatttcct gtttcaggcg acattattgt atgctcaaat    9120
aaccacaact gtagtcagga atggatcatt tcatagctgc acggaccatt accatataac    9180
ctgcaaatct tgtctgaggg ccattgatga gattaccttg gattcagcga tggaatatag    9240
ccctccagat gtatcatcag ttttacaatc ttggaggaat ggagaaggct cttggggaca    9300
tgaagtgaaa caaatatacc cagttgaagg tgactggagg ggactatctc tgttgaaca    9360 atcttatcaa gtcggacgct gtatcgggtt tctgttcggt gatctggcgt atagaaaatc    9420
atcccatgca gatgatagct ccatgttcc gttatctata caaaacaaag tcagaggaag    9480
aggcttttta aaagggctta tggatgggtt aatgagagcc agttgttgcc aggtgatcca    9540
tcgtcgaagc ttagcccatc tgaagagacc ggctaatgca gtctatggag ggctgattta    9600
tttgatagac aaattgagtg catctgcccc ttttctttca ctgacgagac atggacctt     9660 aagggaagaa ttagaaactg ttccacataa gataccgact tcttatccta cgagcaaccg    9720
agatatgggg gtgatagttc gtaattattt taaatatcag tgcagactgg tagaaaaagg    9780
tcggtacaag acacattatc ctcaattgtg gctttctca gatgtgctgt ccattgattt     9840
cttaggaccc ctgtctatat cttcaactct attgggtatt ctgtataaac agacgttatc    9900
ttctcgagac aaaaatgagt tgagagaact cgctaacttg tcttcattgt tgagatcagg    9960
agaaggatgg gaagatatcc atgtcaaatt ccctctaag gacactttac tctgccctga     10020
agagatccga catgcgtgca aatttgggat tgctaaggaa tccgctgttt taagctatta   10080
```

```
tcctccttgg tctcaagagt cttatggagg catcacctcg atccccgtat attttcgac    10140
caggaagtat cccaaaattt tagatgtccc tcctcgggtt caaaacccat tggtctcggg    10200
tctacgattg gggcaactcc ctactggagc acattataag attaggagca ttgtaaagaa    10260
caagaaccct cgttatagag atttccttag ttgtggggat ggatctgggg ggatgaccgc    10320
ggcactattg agagaaaaca gacaaagtag gggaatcttc aacagcctgt tagagttagc    10380
cggatctctt atgagaggag catctccaga gcctccaagt gcactggaga cgctcgggca    10440
agaacgatct aggtgtgtga atggaagcac atgttgggag tactcatctg acctaagcca    10500
aaaagagaca tgggattact tcttaagatt gaagagaggc ctgggtttga ccgtggactt    10560
aatcaccatg gacatggagg tcagagaccc taatacaagt ttgatgatag aaaagaacct    10620
caaagtttat ctgcatcaga tattagaacc aactggtgtc ttaatatata aaacatacgg    10680
gacccatatt gcgacacaaa cagataatat cctgacgata atcggtcctt tctttgagac    10740
ggttgaccta gtccagtccg aatacagcag ctcacaaacg tccgaggtct atttttgtagg    10800
acgaggcttg cgctctcatg ttgacgaacc ctgggtggac tggccatcct taatggacaa    10860
ttggagatcc atttatgctt ttcatgatcc tactacagaa tttatcagag caaaaaaagt    10920
ctgtgaaatt gacagtctta taggcattcc ggctcaattc attccagacc catttgtaaa    10980
tctcgagacc atgctacaga tagttggtgt tccaacagga gtttcgcatg ccgcagctct    11040
attatcatca caatatccaa atcaattggt cacaacgtca atattttata tgacactcgt    11100
gtcttattat aatgtaaacc atattcgaag aagccccaag cctttctctc ctccgtctga    11160
tggagtctca cagaacattg gttcagccat agtcggacta agttttttggg tgagtttgat    11220
ggagaatgat ctcggattat acaaacaggc tctaggtgca ataaagacgt cattccctat    11280
tagatggtcc tctgtccaga ccaaggatgg gtttacacaa gaatgcagaa ctaaaggaaa    11340
cggaattcct aaagattgtc gtctctcaga ctctttggct cagataggaa actggatcag    11400
agcgatggaa ttggttagga acaaaacgag gcaatcagga ttttctgaaa ccctatttga    11460
tcaattctgc ggacttgcag accatcacct caaatggcgg aagttgggaa acagaacagg    11520
aattattgat tggctaaata atagaatttc atccattgac aaatccatct tggtgaccaa    11580
aagtgatctg catgacgaga actcatggag ggagtgaaga tgtattcttc cacctctcat    11640
tgggtgatac ccatatatga aaaaaactat aagtacttta aactctcttt gttttttaat    11700
gtatatctgg ttttgttgtt tccgt                                         11725
```

<210> SEQ ID NO 16  
<211> LENGTH: 238  
<212> TYPE: PRT  
<213> ORGANISM: Homo sapiens

<400> SEQUENCE: 16

```
Met Pro Val Gly Gln Ala Asp Tyr Phe Glu Tyr His Gln Glu Gly Gly
1               5                   10                  15

Pro Asp Gly Glu Pro Asp Met Pro Gly Ala Ile Glu Gln Gly Pro
            20                  25                  30

Ala Asp Asp Pro Gly Glu Gly Pro Ser Thr Gly Pro Arg Gly Gln Gly
        35                  40                  45

Asp Gly Gly Arg Arg Lys Lys Gly Gly Trp Phe Gly Lys His Arg Gly
    50                  55                  60

Gln Gly Gly Ser Asn Gln Lys Phe Glu Asn Ile Ala Asp Gly Leu Arg
65                  70                  75                  80
```

```
Thr Leu Leu Ala Arg Cys His Val Glu Arg Thr Thr Asp Glu Gly Thr
                85                  90                  95

Trp Val Ala Gly Val Phe Val Tyr Gly Gly Ser Lys Thr Ser Leu Tyr
            100                 105                 110

Asn Leu Arg Arg Gly Ile Ser Leu Ala Ile Pro Gln Cys Arg Leu Thr
            115                 120                 125

Pro Leu Ser Arg Leu Pro Phe Gly Met Ala Pro Gly Pro Gly Pro Gln
        130                 135                 140

Pro Gly Pro Leu Arg Glu Ser Ile Val Cys Tyr Phe Ile Val Phe Leu
145                 150                 155                 160

Gln Thr His Ile Phe Ala Glu Gly Leu Lys Asp Ala Ile Lys Asp Leu
                165                 170                 175

Val Met Pro Lys Pro Ala Pro Thr Cys Asn Ile Lys Ala Thr Val Cys
            180                 185                 190

Ser Phe Asp Asp Gly Val Asp Leu Pro Pro Trp Phe Pro Pro Met Val
        195                 200                 205

Glu Gly Ala Ala Ala Glu Gly Asp Asp Gly Asp Gly Asp Gly Asp Gly
        210                 215                 220

Asp Glu Gly Gly Asp Gly Asp Glu Gly Glu Glu Gly Gln Glu
225                 230                 235

<210> SEQ ID NO 17
<211> LENGTH: 717
<212> TYPE: DNA
<213> ORGANISM: Homo sapiens

<400> SEQUENCE: 17
atgccagtcg gccaggctga ttactttgaa taccaccagg agggggggacc agacggagaa      60 ccagacatgc caccaggagc cattgaacag ggaccagcag acgatcctgg agagggacca     120
tcaactggac cccgaggaca ggggacggc ggaaggagaa agaaaggggg atggttcgga     180
aagcaccgag acagggagg gagcaaccag aaatttgaaa atatcgctga cggcctgcga     240
acactgctgg caaggtgcca tgtggagaga accacagatg aaggcacatg ggtcgccgga     300
gtgttcgtct acggcggaag caagacttcc ctgtataacc tgcggcgcgg catctctctg     360
gccattccac agtgccggct gacccctctg agtcgcctgc cattcgggat ggctcctgga     420
ccaggaccac agcctggacc actgagggag tccatcgtgt gctacttcat tgtctttctg     480
cagacacaca tctttgccga aggcctgaag gacgccatca ggacctggt catgcccaag     540 cctgcaccaa cttgcaatat caaggccacc gtgtgcagtt tcgacgatgg cgtggacctg     600 ccccccttggt ttccacctat ggtggaggga gccgctgcag aaggggacga tggcgatgac     660
ggggacgatg gggatgaagg cggggacggc gatgagggag aagagggca ggaataa         717

<210> SEQ ID NO 18
<211> LENGTH: 30
<212> TYPE: DNA
<213> ORGANISM: Artificial Sequence
<220> FEATURE:
<223> OTHER INFORMATION: synthesized primer

<400> SEQUENCE: 18
actggaattc atgcatcaga agcgaactgc                                       30

<210> SEQ ID NO 19
<211> LENGTH: 29
<212> TYPE: DNA
<213> ORGANISM: Artificial Sequence
```

```
<220> FEATURE:
<223> OTHER INFORMATION: synthesized primer

<400> SEQUENCE: 19
actgggatcc tcactgctgg gaggcacac                                    29

<210> SEQ ID NO 20
<211> LENGTH: 29
<212> TYPE: DNA
<213> ORGANISM: Artificial Sequence
<220> FEATURE:
<223> OTHER INFORMATION: synthesized primer

<400> SEQUENCE: 20
actgggatcc atgcaggccg agggcagag                                    29

<210> SEQ ID NO 21
<211> LENGTH: 30
<212> TYPE: DNA
<213> ORGANISM: Artificial Sequence
<220> FEATURE:
<223> OTHER INFORMATION: synthesized primer

<400> SEQUENCE: 21
actgggatcc tcatcttctc tggccgctgg                                   30

<210> SEQ ID NO 22
<211> LENGTH: 31
<212> TYPE: DNA
<213> ORGANISM: Artificial Sequence
<220> FEATURE:
<223> OTHER INFORMATION: synthesized primer

<400> SEQUENCE: 22
actggaattc atggaatcac ggaaggacat c                                 31

<210> SEQ ID NO 23
<211> LENGTH: 32
<212> TYPE: DNA
<213> ORGANISM: Artificial Sequence
<220> FEATURE:
<223> OTHER INFORMATION: synthesized primer

<400> SEQUENCE: 23
actgggatcc ttaaagcttc agctggctac ag                                32

<210> SEQ ID NO 24
<211> LENGTH: 29
<212> TYPE: DNA
<213> ORGANISM: Artificial Sequence
<220> FEATURE:
<223> OTHER INFORMATION: synthesized primer

<400> SEQUENCE: 24
actggaattc atgccagtcg gccaggctg                                    29

<210> SEQ ID NO 25
<211> LENGTH: 31
<212> TYPE: DNA
<213> ORGANISM: Artificial Sequence
<220> FEATURE:
<223> OTHER INFORMATION: synthesized primer

<400> SEQUENCE: 25
actgggatcc ttattcctgc ccctcttctc c                                 31
```

```
<210> SEQ ID NO 26
<211> LENGTH: 9
<212> TYPE: PRT
<213> ORGANISM: Artificial Sequence
<220> FEATURE:
<223> OTHER INFORMATION: antigenic epitope from human MAGEA3 protein

<400> SEQUENCE: 26

Glu Val Asp Pro Ile Gly His Leu Tyr
1               5

<210> SEQ ID NO 27
<211> LENGTH: 9
<212> TYPE: PRT
<213> ORGANISM: Artificial Sequence
<220> FEATURE:
<223> OTHER INFORMATION: antigenic epitope from human MAGEA3 protein

<400> SEQUENCE: 27

Phe Leu Trp Gly Pro Arg Ala Leu Val
1               5

<210> SEQ ID NO 28
<211> LENGTH: 9
<212> TYPE: PRT
<213> ORGANISM: Artificial Sequence
<220> FEATURE:
<223> OTHER INFORMATION: antigenic epitope from human MAGEA3 protein

<400> SEQUENCE: 28

Lys Val Ala Glu Leu Val His Phe Leu
1               5

<210> SEQ ID NO 29
<211> LENGTH: 9
<212> TYPE: PRT
<213> ORGANISM: Artificial Sequence
<220> FEATURE:
<223> OTHER INFORMATION: antigenic epitope from human MAGEA3 protein

<400> SEQUENCE: 29

Thr Phe Pro Asp Leu Glu Ser Glu Phe
1               5

<210> SEQ ID NO 30
<211> LENGTH: 9
<212> TYPE: PRT
<213> ORGANISM: Artificial Sequence
<220> FEATURE:
<223> OTHER INFORMATION: antigenic epitope from human MAGEA3 protein

<400> SEQUENCE: 30

Val Ala Glu Leu Val His Phe Leu Leu
1               5

<210> SEQ ID NO 31
<211> LENGTH: 10
<212> TYPE: PRT
<213> ORGANISM: Artificial Sequence
<220> FEATURE:
<223> OTHER INFORMATION: antigenic epitope from human MAGEA3 protein

<400> SEQUENCE: 31

Met Glu Val Asp Pro Ile Gly His Leu Tyr
1               5                   10
```

```
<210> SEQ ID NO 32
<211> LENGTH: 10
<212> TYPE: PRT
<213> ORGANISM: Artificial Sequence
<220> FEATURE:
<223> OTHER INFORMATION: antigenic epitope from human MAGEA3 protein

<400> SEQUENCE: 32

Arg Glu Pro Val Thr Lys Ala Glu Met Leu
1               5                   10

<210> SEQ ID NO 33
<211> LENGTH: 9
<212> TYPE: PRT
<213> ORGANISM: Artificial Sequence
<220> FEATURE:
<223> OTHER INFORMATION: antigenic epitope from human MAGEA3 protein

<400> SEQUENCE: 33

Ala Glu Leu Val His Phe Leu Leu Leu
1               5

<210> SEQ ID NO 34
<211> LENGTH: 9
<212> TYPE: PRT
<213> ORGANISM: Artificial Sequence
<220> FEATURE:
<223> OTHER INFORMATION: antigenic epitope from human MAGEA3 protein

<400> SEQUENCE: 34

Trp Gln Tyr Phe Phe Pro Val Ile Phe
1               5

<210> SEQ ID NO 35
<211> LENGTH: 9
<212> TYPE: PRT
<213> ORGANISM: Artificial Sequence
<220> FEATURE:
<223> OTHER INFORMATION: antigenic epitope from human MAGEA3 protein

<400> SEQUENCE: 35

Glu Gly Asp Cys Ala Pro Glu Glu Lys
1               5

<210> SEQ ID NO 36
<211> LENGTH: 16
<212> TYPE: PRT
<213> ORGANISM: Artificial Sequence
<220> FEATURE:
<223> OTHER INFORMATION: antigenic epitope from human MAGEA3 protein

<400> SEQUENCE: 36

Lys Lys Leu Leu Thr Gln His Phe Val Gln Glu Asn Tyr Leu Glu Tyr
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: antigenic epitope from human MAGEA3 protein

<400> SEQUENCE: 37

Arg Lys Val Ala Glu Leu Val His Phe Leu Leu Leu Lys Tyr Arg
1               5                   10                  15

<210> SEQ ID NO 38
```

```
<211> LENGTH: 16
<212> TYPE: PRT
<213> ORGANISM: Artificial Sequence
<220> FEATURE:
<223> OTHER INFORMATION: antigenic epitope from human MAGEA3 protein

<400> SEQUENCE: 38

Ala Cys Tyr Glu Phe Leu Trp Gly Pro Arg Ala Leu Val Glu Thr Ser
1               5                   10                  15

<210> SEQ ID NO 39
<211> LENGTH: 12
<212> TYPE: PRT
<213> ORGANISM: Artificial Sequence
<220> FEATURE:
<223> OTHER INFORMATION: antigenic epitope from human MAGEA3 protein

<400> SEQUENCE: 39

Val Ile Phe Ser Lys Ala Ser Ser Ser Leu Gln Leu
1               5                   10

<210> SEQ ID NO 40
<211> LENGTH: 15
<212> TYPE: PRT
<213> ORGANISM: Artificial Sequence
<220> FEATURE:
<223> OTHER INFORMATION: antigenic epitope from human MAGEA3 protein

<400> SEQUENCE: 40

Val Phe Gly Ile Glu Leu Met Glu Val Asp Pro Ile Gly His Leu
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: antigenic epitope from human MAGEA3 protein

<400> SEQUENCE: 41

Gly Asp Asn Gln Ile Met Pro Lys Ala Gly Leu Leu Ile Ile Val
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: antigenic epitope from human MAGEA3 protein

<400> SEQUENCE: 42

Thr Ser Tyr Val Lys Val Leu His His Met Val Lys Ile Ser Gly
1               5                   10                  15

<210> SEQ ID NO 43
<211> LENGTH: 16
<212> TYPE: PRT
<213> ORGANISM: Artificial Sequence
<220> FEATURE:
<223> OTHER INFORMATION: antigenic epitope from human MAGEA3 protein

<400> SEQUENCE: 43

Arg Lys Val Ala Glu Leu Val His Phe Leu Leu Leu Lys Tyr Arg Ala
1               5                   10                  15

<210> SEQ ID NO 44
<211> LENGTH: 16
```

```
<212> TYPE: PRT
<213> ORGANISM: Artificial Sequence
<220> FEATURE:
<223> OTHER INFORMATION: antigenic epitope from human MAGEA3 protein

<400> SEQUENCE: 44

Phe Leu Leu Leu Lys Tyr Arg Ala Arg Glu Pro Val Thr Lys Ala Glu
1               5                   10                  15

<210> SEQ ID NO 45
<211> LENGTH: 9
<212> TYPE: PRT
<213> ORGANISM: Artificial Sequence
<220> FEATURE:
<223> OTHER INFORMATION: MHC-I restricted immunodominant epitope from
      melanoma associated antigen dopachrome tautomerase

<400> SEQUENCE: 45

Ser Val Tyr Asp Phe Phe Val Trp Leu
1               5

<210> SEQ ID NO 46
<211> LENGTH: 14
<212> TYPE: PRT
<213> ORGANISM: Artificial Sequence
<220> FEATURE:
<223> OTHER INFORMATION: MHC-II restricted immunodominant epitope from
      melanoma associated antigen dopachrome tautomerase

<400> SEQUENCE: 46

Lys Phe Phe His Arg Thr Cys Lys Cys Thr Gly Asn Phe Ala
1               5                   10

<210> SEQ ID NO 47
<211> LENGTH: 9
<212> TYPE: PRT
<213> ORGANISM: Artificial Sequence
<220> FEATURE:
<223> OTHER INFORMATION: antigenic epitope

<400> SEQUENCE: 47

Arg Ala His Tyr Asn Ile Val Thr Phe
1               5

<210> SEQ ID NO 48
<211> LENGTH: 8
<212> TYPE: PRT
<213> ORGANISM: Artificial Sequence
<220> FEATURE:
<223> OTHER INFORMATION: antigenic epitope

<400> SEQUENCE: 48

Arg Gly Pro Glu Ser Arg Leu Leu
1               5

<210> SEQ ID NO 49
<211> LENGTH: 7
<212> TYPE: PRT
<213> ORGANISM: Artificial Sequence
<220> FEATURE:
<223> OTHER INFORMATION: antigenic epitope

<400> SEQUENCE: 49

Arg Ser Arg Tyr Lys Leu Leu
1               5

<210> SEQ ID NO 50
```

```
<211> LENGTH: 9
<212> TYPE: PRT
<213> ORGANISM: Artificial Sequence
<220> FEATURE:
<223> OTHER INFORMATION: antigenic epitope

<400> SEQUENCE: 50

Val Tyr Gly Gly Ser Lys Thr Ser Leu
1               5
```